(12) United States Patent
Islam

(10) Patent No.: US 10,271,904 B2
(45) Date of Patent: Apr. 30, 2019

(54) LASER-BASED METHOD AND SYSTEM FOR SELECTIVELY PROCESSING TARGET TISSUE MATERIAL IN A PATIENT AND OPTICAL CATHETER ASSEMBLY FOR USE THEREIN

(71) Applicant: OMNI MEDSCI, INC., Ann Arbor, MI (US)

(72) Inventor: Mohammed N. Islam, Ann Arbor, MI (US)

(73) Assignee: OMNI MEDSCI, INC., Ann Arbor, MI (US)

( * ) Notice: Subject to any disclaimer, the term of this patent is extended or adjusted under 35 U.S.C. 154(b) by 211 days.

(21) Appl. No.: 14/719,262

(22) Filed: May 21, 2015

(65) Prior Publication Data

US 2015/0250542 A1    Sep. 10, 2015

Related U.S. Application Data

(60) Division of application No. 13/215,837, filed on Aug. 23, 2011, now Pat. No. 9,066,736, which is a
(Continued)

(51) Int. Cl.
*A61B 18/20* (2006.01)
*A61F 9/008* (2006.01)
(Continued)

(52) U.S. Cl.
CPC .... *A61B 18/20* (2013.01); *A61B 2018/00464* (2013.01); *A61B 2018/2065* (2013.01);
(Continued)

(58) Field of Classification Search
CPC ............ A61B 18/20; A61B 2018/2065; A61B 2018/2244; A61F 9/008; A61F 9/00804;
(Continued)

(56) References Cited

U.S. PATENT DOCUMENTS

| 4,063,106 A | 12/1977 | Ashkin et al. |
| 4,158,750 A | 6/1979 | Sakoe et al. |

(Continued)

FOREIGN PATENT DOCUMENTS

| EP | 1148666 A2 | 10/2001 |
| WO | 9715240 A1 | 5/1997 |

(Continued)

OTHER PUBLICATIONS

Huang, et al., "Update on nonexcimer laser refractive surgery technique: conductive keratoplasty" Curr Opin Ophthalmol 14:203-206. (Aug. 2003).

(Continued)

*Primary Examiner* — Aaron F Roane
(74) *Attorney, Agent, or Firm* — Brooks Kushman P.C.

(57) ABSTRACT

A system and method for selectively processing target tissue material in a patient include a laser subsystem for generating an output laser beam and a catheter assembly including an optical fiber for guiding the output laser beam. The beam has a predetermined selected wavelength between 900 nm and 2600 nm. The catheter assembly is sized to extend through an opening in a first part of the patient to a tissue material processing site within the patient. A beam delivery and focusing subsystem includes a focal distance, which may be adjustable, that positions the beam into at least one focused spot on the target tissue material disposed within a second part of the patient for a duration sufficient to allow laser energy to be absorbed by the target tissue material and converted to heat to produce a desired physical change in the target tissue material without causing undesirable changes to adjacent non-target material.

20 Claims, 27 Drawing Sheets

Related U.S. Application Data continuation-in-part of application No. PCT/US2010/062467, filed on Dec. 30, 2010.

(60) Provisional application No. 61/335,456, filed on Jan. 7, 2010, provisional application No. 61/335,455, filed on Jan. 7, 2010, provisional application No. 61/335,440, filed on Jan. 7, 2010.

(51) Int. Cl.
| | |
|---|---|
| *A61B 18/22* | (2006.01) |
| *H01S 3/00* | (2006.01) |
| *H01S 3/067* | (2006.01) |
| *H01S 3/094* | (2006.01) |
| *H01S 3/16* | (2006.01) |
| *H01S 3/30* | (2006.01) |
| *A61B 18/00* | (2006.01) |

(52) U.S. Cl.
CPC ....... *A61B 2018/2244* (2013.01); *A61F 9/008* (2013.01); *A61F 9/00804* (2013.01); *A61F 9/00814* (2013.01); *H01S 3/0064* (2013.01); *H01S 3/0078* (2013.01); *H01S 3/0675* (2013.01); *H01S 3/06758* (2013.01); *H01S 3/094042* (2013.01); *H01S 3/1616* (2013.01); *H01S 3/1618* (2013.01); *H01S 3/302* (2013.01)

(58) Field of Classification Search
CPC .. A61F 9/00814; H01S 3/0064; H01S 3/0078; H01S 3/0675; H01S 3/06758; H01S 3/094042; H01S 3/1616; H01S 3/1618; H01S 3/302
USPC .............................................. 606/15; 607/88
See application file for complete search history.

(56) References Cited

U.S. PATENT DOCUMENTS

| | | |
|---|---|---|
| 4,221,997 A | 9/1980 | Flemming |
| 4,275,266 A | 6/1981 | Lasar |
| 4,318,058 A * | 3/1982 | Mito ................. H01S 5/1028 372/50.11 |
| 4,374,618 A | 2/1983 | Howard |
| 4,403,605 A | 9/1983 | Tanikawa |
| 4,445,892 A | 5/1984 | Hussein et al. |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,672,961 A | 6/1987 | Davies |
| 4,704,696 A | 11/1987 | Reimer et al. |
| 4,728,974 A | 3/1988 | Nio et al. |
| 47,622,455 | 8/1988 | Coughlan et al. |
| 4,776,016 A | 10/1988 | Hansen |
| 4,852,567 A | 8/1989 | Sinofsky |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,242,438 A | 9/1993 | Saadatmanesh et al. |
| 5,267,256 A | 11/1993 | Saruwatari et al. |
| 5,267,323 A | 11/1993 | Kimura |
| 5,300,097 A | 4/1994 | Lemer et al. |
| 5,303,148 A | 4/1994 | Mattson et al. |
| 5,304,169 A | 4/1994 | Sand |
| 5,305,427 A | 4/1994 | Nagata |
| 5,313,306 A | 5/1994 | Kuban et al. |
| 5,323,404 A | 6/1994 | Grubb |
| 5,334,190 A | 8/1994 | Seiler |
| 5,345,538 A | 9/1994 | Narayannan et al. |
| 5,400,165 A | 3/1995 | Gnauck et al. |
| 5,408,409 A | 4/1995 | Glassman et al. |
| 5,409,482 A | 4/1995 | Diamantopoulos |
| 5,433,739 A | 7/1995 | Sluijter et al. |
| 5,484,432 A | 1/1996 | Sand |
| 5,544,654 A | 8/1996 | Murphy et al. |
| 5,571,147 A | 11/1996 | Sluijter et al. |
| 5,572,999 A | 11/1996 | Funda et al. |
| 5,618,284 A | 4/1997 | Sand |
| 5,631,758 A | 5/1997 | Knox et al. |
| 5,695,493 A | 12/1997 | Nakajima et al. |
| 5,696,778 A | 12/1997 | McPherson |
| 5,779,696 A | 6/1998 | Berry et al. |
| 5,785,704 A | 7/1998 | Bille et al. |
| 5,792,204 A | 8/1998 | Snell |
| 5,812,978 A | 9/1998 | Nolan |
| 5,820,626 A | 10/1998 | Baumgardner |
| 5,867,305 A | 2/1999 | Waarts et al. |
| 5,885,274 A | 3/1999 | Fullmer et al. |
| 5,912,749 A | 6/1999 | Harstead et al. |
| 5,950,629 A | 9/1999 | Taylor et al. |
| 5,968,034 A | 10/1999 | Fullmer et al. |
| 5,970,457 A | 10/1999 | Brant et al. |
| 5,976,123 A | 11/1999 | Baumgardner |
| 6,014,249 A | 1/2000 | Fermann et al. |
| 6,043,927 A | 3/2000 | Islam |
| 6,095,982 A | 8/2000 | Richards-Kortum et al. |
| 6,159,205 A | 12/2000 | Hereaker et al. |
| 6,185,535 B1 | 2/2001 | Hedin et al. |
| 6,200,309 B1 | 3/2001 | Rice et al. |
| 6,224,542 B1 | 5/2001 | Chang et al. |
| 6,235,016 B1 | 5/2001 | Stewart |
| 6,246,707 B1 | 6/2001 | Yin et al. |
| 6,251,103 B1 | 6/2001 | Berlin |
| 6,273,858 B1 | 8/2001 | Fox et al. |
| 6,273,885 B1 | 8/2001 | Koop et al. |
| 6,278,975 B1 | 8/2001 | Brant et al. |
| 6,301,273 B1 | 10/2001 | Sanders et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,374,006 B1 | 4/2002 | Islam et al. |
| 6,381,391 B1 | 4/2002 | Islam et al. |
| 6,387,380 B1 | 5/2002 | Knowlton |
| 6,398,777 B1 | 6/2002 | Navarro et al. |
| 6,407,853 B1 | 6/2002 | Samson et al. |
| 6,413,253 B1 | 7/2002 | Koop et al. |
| 6,436,107 B1 | 8/2002 | Wang et al. |
| 6,442,430 B1 | 8/2002 | Ferek-Petric |
| 6,450,172 B1 | 9/2002 | Hartlaub et al. |
| 6,451,007 B1 | 9/2002 | Koop et al. |
| 6,453,201 B1 | 9/2002 | Daum et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,549,702 B2 | 4/2003 | Islam et al. |
| 6,567,431 B2 | 5/2003 | Tabirian et al. |
| 6,603,910 B2 | 8/2003 | Islam et al. |
| 6,605,080 B1 | 8/2003 | Altshuler et al. |
| 6,625,180 B2 | 9/2003 | Bufetov et al. |
| 6,626,898 B2 | 9/2003 | Frey et al. |
| 6,631,025 B2 | 10/2003 | Islam et al. |
| 6,659,999 B1 | 12/2003 | Anderson et al. |
| 6,760,148 B2 | 7/2004 | Islam |
| 6,885,498 B2 | 4/2005 | Islam |
| 6,885,683 B1 | 4/2005 | Fermann et al. |
| 6,943,936 B2 | 9/2005 | Islam et al. |
| 6,978,174 B2 | 12/2005 | Gelfand et al. |
| 6,986,764 B2 | 1/2006 | Davenport et al. |
| 6,991,927 B2 | 1/2006 | Mross et al. |
| 6,997,923 B2 | 2/2006 | Anderson et al. |
| 7,027,467 B2 | 4/2006 | Baev et al. |

(56) References Cited

U.S. PATENT DOCUMENTS

| | | |
|---|---|---|
| 7,044,945 B2 | 5/2006 | Sand |
| 7,060,061 B2 | 6/2006 | Altshuler et al. |
| 7,094,252 B2 | 8/2006 | Koop |
| 7,098,992 B2 | 8/2006 | Ohtsuki et al. |
| 7,122,029 B2 | 10/2006 | Koop et al. |
| 7,160,287 B1 * | 1/2007 | Siegel ............... A61B 18/203 606/3 |
| 7,162,303 B2 | 1/2007 | Levin et al. |
| 7,167,300 B2 | 1/2007 | Fermann et al. |
| 7,209,657 B1 | 4/2007 | Islam |
| 7,217,265 B2 | 5/2007 | Hennings et al. |
| 7,238,180 B2 | 7/2007 | Mester et al. |
| 7,259,906 B1 | 8/2007 | Islam |
| 7,263,288 B1 | 8/2007 | Islam |
| 7,288,756 B2 | 10/2007 | Sherrer et al. |
| 7,357,796 B2 | 4/2008 | Farr et al. |
| 7,433,116 B1 | 10/2008 | Islam |
| 7,468,062 B2 | 12/2008 | Oral et al. |
| 7,486,978 B2 | 2/2009 | Van Beek et al. |
| 7,519,253 B2 | 4/2009 | Islam |
| 7,524,316 B2 | 4/2009 | Hennings et al. |
| 7,617,005 B2 | 11/2009 | Demarais et al. |
| 7,620,451 B2 | 11/2009 | Demarais et al. |
| 7,633,673 B1 | 12/2009 | Islam |
| 7,647,115 B2 | 1/2010 | Levin et al. |
| 7,653,438 B2 | 1/2010 | Deem et al. |
| 7,717,948 B2 | 5/2010 | Demarais et al. |
| 7,756,583 B2 | 7/2010 | Demarais et al. |
| 7,853,333 B2 | 12/2010 | Demarais |
| 7,857,808 B2 | 12/2010 | Oral et al. |
| 7,873,417 B2 | 1/2011 | Demarais et al. |
| 7,937,143 B2 | 5/2011 | Demarais et al. |
| 9,066,736 B2 | 6/2015 | Islam |
| 2002/0032468 A1 | 3/2002 | Hill et al. |
| 2002/0082612 A1 | 6/2002 | Moll et al. |
| 2002/0128846 A1 | 9/2002 | Miller |
| 2002/0178003 A1 | 11/2002 | Gehrke et al. |
| 2003/0028228 A1 | 2/2003 | Sand |
| 2004/0034341 A1 | 2/2004 | Altshuler et al. |
| 2004/0174914 A1 | 9/2004 | Fukatsu |
| 2004/0240037 A1 | 12/2004 | Harter |
| 2005/0075704 A1 | 4/2005 | Tu et al. |
| 2005/0111500 A1 | 5/2005 | Harter et al. |
| 2005/0238070 A1 | 10/2005 | Imeshev et al. |
| 2006/0000988 A1 | 1/2006 | Stuart et al. |
| 2006/0013270 A1 | 1/2006 | Yumoto et al. |
| 2006/0245461 A1 | 11/2006 | Islam |
| 2007/0020181 A1 | 1/2007 | Workman et al. |
| 2007/0060984 A1 * | 3/2007 | Webb ............... A61N 5/0601 607/89 |
| 2007/0073280 A1 | 3/2007 | Johnson et al. |
| 2007/0078348 A1 | 4/2007 | Holman |
| 2007/0123846 A1 | 5/2007 | Hennings |
| 2007/0179481 A1 | 8/2007 | Fragineas et al. |
| 2007/0293849 A1 | 12/2007 | Hennings et al. |
| 2008/0015557 A1 | 1/2008 | Chan |
| 2008/0058783 A1 | 3/2008 | Altshuler et al. |
| 2008/0132886 A1 | 6/2008 | Cohen et al. |
| 2008/0215040 A1 | 9/2008 | Paithankar et al. |
| 2008/0269735 A1 | 10/2008 | Vila Echague et al. |
| 2009/0028193 A1 | 1/2009 | Islam |
| 2009/0054879 A1 | 2/2009 | Berry |
| 2009/0062873 A1 | 3/2009 | Wu et al. |
| 2009/0076409 A1 | 3/2009 | Wu et al. |
| 2009/0204110 A1 | 8/2009 | Islam |
| 2009/0263489 A1 | 10/2009 | Chun et al. |
| 2009/0296743 A1 | 12/2009 | Islam |
| 2009/0326617 A1 | 12/2009 | Asano |
| 2010/0069723 A1 | 3/2010 | Islam |
| 2010/0168731 A1 | 7/2010 | Wu et al. |
| 2010/0168739 A1 | 7/2010 | Wu et al. |
| 2011/0007315 A1 | 1/2011 | Petersen et al. |
| 2011/0060324 A1 | 3/2011 | Wu et al. |
| 2011/0257641 A1 | 10/2011 | Hastings et al. |

FOREIGN PATENT DOCUMENTS

| | | |
|---|---|---|
| WO | 9749340 A1 | 12/1997 |
| WO | 0150959 A1 | 7/2001 |
| WO | 2004004569 A1 | 1/2004 |

OTHER PUBLICATIONS

Husakou, Anton V., et al., "Supercontinuum generation, four-wave mixing, and fission of higher-order solitons in photonic-crystal fibers", J. Opt. Soc. Am. B, vol. 19, No. 9, pp. 2171-2182. (Sep. 2002).

Iatridis, James C., et al., "Is the Nucleus Pulposus a Solid or a Fluid? Mechanical Behaviors of the Nucleus Pulposus of the Human Intervertebral Disc", Spine, vol. 21 (10), pp. 1174-1184. (May 15, 1996).

Inoue, H., et al., "Computer simulation of the vibrational spectra and properties of fluoride glasses based on $ZrF4$", Journal of Non-Crystalline Solids, vol. 161, pp. 118-122. (1993).

Islam, M.N., "Broad bandwidths from frequency-shifting solitons in fibers", Optics Letters, vol. 14, No. 7, pp. 370-372. (Apr. 1, 1989).

Islam, M.N., "Femtosecond distributed soliton spectrum in fibers", J. Opt. Soc. Am. B, vol. 6, No. 6, pp. 1149-1158. (Jun. 1989).

Kondepati, et al., "Near-infrared fiber optic spectroscopy as a novel diagnostic tool for the detection of pancreatic cancer" Journal of Biomedical Optics 10 (5). (Oct. 13, 2005).

Islam, Mohammed N., U.S. Appl. No. 10/812,608, entitled "System and Method for Voice Control of Medical Devices". (Mar. 30, 2004).

Jackson, Stuart D., et al., "Theory and numerical simulation of nth-order cascaded Raman fiber lasers", J. Opt. Soc. Am. B, vol. 18, No. 9, pp. 1297-1306. (Sep. 2001).

Karimpour, et al., "Molecular Analysis of Aggressive Microdermabrasion in Photoaged Skin." Arch Dermatol/vol. 145 (No. 10). (Oct. 1, 2009).

Kobtsev, Serguei M., et al, Modelling of high-power supercontinuum generation in highly nonlinear, dispersion shifted fibers at CW pump, Optics Express, vol. 13, No. 18, pp. 6912-6918. (Sep. 5, 2005).

Kowalevicz, Andrew M., "Ultrahigh resolution optical coherence tomography using a superluminescent light source", Optics Express 349, vol. 10, No. 7, pp. 349-353. (Apr. 8, 2002).

Kumar, V.V. Raavi Kanth, et al., "Extruded soft glass photonic crystal fiber for ultrabroad supercontinuum generation", Optics Express, vol. 10, No. 25, pp. 1520-1525. ( Dec. 16, 2002).

Kutz, J. Nathan, et al, "Enhanced Supercontinuum Generation through Dispersion-Management", Optics Express, vol. 13, No. 11, pp. 3989-3998. (May 30, 2005).

Lee, Ju Han, et al., "Continuous-wave supercontinuum laser based on an erbium-doped fiber ring cavity incorporating a highly nonlinear optical fiber", Optics Letters, vol. 30, No. 19, pp. 2599-2601. ( Oct. 1, 2005).

Lee, Ju Han, et al., "Experimental performance comparison for various continuous-wave supercontinuum schemes: ring cavity and single pass structures", Optics Express, vol. 13, No. 13, pp. 4848-4853. (Jun. 27, 2005).

Leon-Saval, S.G., et al., "Supercontinuum generation in submicron fibre waveguides", Optics Express, vol. 12, No. 13, pp. 2864-2869. ( Jun. 28, 2004).

Li, Xingde, et al., "Imaging needle for optical coherence tomography", Optics Letters, vol. 25, No. 20, pp. 1520-1522. (Oct. 15, 2000).

Lucas, Jacques, "Infrared glasses", Current Opinion in Solid State & Materials Science 4, pp. 181-187. (1999).

Mizunami, Toru, et al., "Gain saturation characteristics of Raman amplification in silica and fluoride glass optical fibers", Optics Communications 97, pp. 74-78. (1993).

Moon, Sucbei, et al., "Generation of octave-spanning supercontinuum with 1550-nm amplified diode-laser pulses and a dispersion-shifted fiber", Optics Express, vol. 14, No. 1, pp. 270-278. ( Jan. 9, 2006).

(56) References Cited

OTHER PUBLICATIONS

Mussot, Arnaud, et al., "Generation of a broadband single-mode supercontinuum in a conventional dispersion-shifted fiber by use of a subnanosecond microchip laser", Optics Letters, vol. 28, No. 19, pp. 1820-1822. (Oct. 1, 2003).

Nassif, N.A., et al., "In vivo high-resolution video-rate spectral-domain optical coherence tomography of the human retina and optic nerve", Optics Express, vol. 12, No. 3, pp. 367-376. (Feb. 9, 2004).

Nazarian, S., et al., 2005, "Direct visualization of coronary sinus ostium and branches with a flexible steerable fiberoptic infrared endoscope," Heart Rhythm 2: 844-848. (2005).

New and Emerging Techniques—Surgical, Rapid Review, Laser Discectomy, Australian Safety and Efficacy Register of New Interventional Procedures—Surgical, 12 pages. (Jun. 2003).

Nicholson, J.W., et al., "All-fiber, octave-spanning supercontinuum", Optics Letters, vol. 28, No. 8, pp. 643-645. (Apr. 15, 2003).

Nicholson, J.W., et al., "High power, single mode, all-fiber source of femtosecond pulses at 1550 nm and its use in supercontinuum generation", Optics Express, vol. 12, No. 13, pp. 3025-3034. (Jun. 28, 2004).

Nicholson, J.W., et al, "Pulsed and continuous-wave supercontinuum generation in highly nonlinear, dispersion-shifted fibers", Applied Physics B 77, pp. 211-218. ( 2003).

Nicholson, J.W., "Supercontinuum generation in ultraviolet-irradiated fibers", Optics Letters, vol. 29, No. 20, pp. 2363-2365. (Oct. 15, 2004).

Nishida, Yoshiki, et al., "Reliability of Fluoride Fiber Module for Optical Amplifier Use", IEEE Photonics Technology Letters, vol. 11, No. 12, pp. 1596-1598. (Dec. 1999).

Nowak, G.A., et al., "Low-power high-efficiency wavelength conversion based on modulational instability in high-nonlinearity fiber," Optics Letters, vol. 23, No. 12, pp. 936-938. (Jun. 15, 1998).

Nowak, George A., et al., "Stable supercontinuum generation in short lengths of conventional dispersion-shifted fiber", Applied Optics, vol. 38, No. 36, pp. 7364-7369. (Dec. 20, 1999).

Orringer, et al., "Dermal matrix remodeling after nonablative laser therapy." J am Acad Dermatol vol. 53. No. 5. (2005).

Oughstun, Kurt E., "Influence of precursor fields on ultrashort pulse autocorrelation measurements and pulse width evolution", Optics Express, vol. 8, No. 8, pp. 481-491. ( Apr. 9, 2001).

Pan, Yingtian, et al., "Hand-held arthroscopic optical coherence tomography for in vivo high-resolution imaging of articular cartilage", Journal of Biomedical Optics 8(4), pp. 648-654. (Oct. 2003).

Papernyi, S.B., et al., "Sixth-Order Cascaded Raman Amplification", OFC/NFOEC, 3 pages. (2005).

Park, Jesung, et al., "Analysis of birefringent image in the retinal nerve fiber layer by polarization sensitive optical coherence tomography", Ophthalmic Technologies XIV, Proceedings of SPIE, vol. 5314, pp. 188-194. (2004).

Patent Application entitled, "System and Method for Generating Supercontinuum Light", 34 pages specification, claims and abstract, 15 pages of drawings, inventor Mohammed N. Islam, (Nov. 18, 2005).

PCT/US06/44451, International Search Report and the Written Opinion of the International Searching Authority, 9 pages (Nov. 29, 2007).

Pierce, Mark C., "Advances in Optical Coherence Tomography Imaging for Dermatology", Optical Coherence Tomography Advances, The Journal of Investigative Dermatology, pp. 458-463. (Sep. 3, 2004).

Wadsworth, W.J., et al., "Supercontinuum and four-wave mixing with Q-switched pulses in endlessly single-mode photonic crystal fibres", Optics Express, vol. 12, No. 2, pp. 299-309. (Jan. 26, 2004).

Ranka, Jinendra K., et al., "Visible continuum generation in air-silica microstructure optical fibers with anomalous dispersion at 800 nm", Optics Letters, vol. 25, No. 1, pp. 25-27. (Jan. 1, 2000).

"Renal Artery" Wikipedia, the free encyclopedia. <http://en.wikipedia.org/wiki/Renal_artery>. (2011).

Roggan, Andre, et al., "Optical Properties of Circulating Human Blood in the Wavelength Range 400-2500 NM", Journal of Biomedical Optics, vol. 4, No. 1, pp. 36-46. (Jan. 1999).

Rollins, Andrew M., et al., "Real-time in vivo imaging of human gastrointestinal ultrastructure by use of endoscopic optical coherence tomography with a novel efficient interferometer design", Optics Letters, vol. 24, No. 19, pp. 1358-1360. (Oct. 1, 1999).

Saliminia, A., et al., Ultra-broad and coherent white light generation in silica glass by focused femtosecond pulses at 1.5 µm, Optics Express, vol. 13, No. 15, pp. 5731-5738. (Jul. 25, 2005).

Sanghera, J.S., et al., "Active and passive chalcogenide glass optical fibers for IR applications: a review", Journal of Non-Crystalline Solids 256 & 257, pp. 6-16. (1999).

Schmitt, Joseph, et al., "Intravascular Optical Coherence Tomography Opens a Window Onto Coronary Artery Disease", Optics & Photonics News, pp. 20-25. (Feb. 2004).

Schreiber, T., et al., "Supercontinuum generation by femtosecond single and dual wavelength pumping in photonic crystal fibers with two zero dispersion wavelengths", Optics Express, vol. 13, No. 23, pp. 9556-9569. (Nov. 14, 2005).

Seefeldt, Michael, et al., "Compact white-light source with an average output power of 2.4 W and 900 nm spectral bandwidth", Optics Communications 216, pp. 199-202. (2003).

Shaw, et al, IR Supercontinuum Generation in As-Se Photonic Crystal Fiber, Optical Society of America, 3 pages. (2005).

Wadsworth, William J., et al, "Supercontinuum generation in photonic crystal fibers and optical fiber tapers: a novel light source", J. Opt. Soc. Am. B, vol. 19, No. 9, pp. 2148-2155. (Sep. 2002).

Slusher, Richard E., et al., "Large Raman gain and nonlinear phase shifts in high-purity As2Se3 chalcogenide fibers", J. Opt. Soc. Am. B, vol. 21, No. 6, pp. 1146-1155. (Jun. 2004).

Smektala, F., et al., "Chalcogenide glasses with large non-linear refractive indices", Journal of Non-Crystalline Solids 239, pp. 139-142. (1998).

Sobol, Emil, et al., "Time-resolved, light scattering measurements of cartilage and cornea denaturation due to free electron laser radiation", Journal of biomedical Optics, vol. 8, No. 2, pp. 216-222. (Apr. 2003).

Venugopalan, V., "Optical Society of American BIOMED Topical Meeting Tutorial on Tissue Optics", pp. 1-32. (Apr. 27, 2004).

Takushima, Yuichi, High average power, depolarized supercontinuum generation using a 1.55µm ASE noise source, Optics Express, vol. 13, No. 15, pp. 5871-5877. (Jul. 25, 2005).

Tanaka, Keiji, "Optical nonlinearity in photonic glasses", Journal of Materials Science: Materials in Electronics 16, pp. 633-643. (2005).

Tearney, Guillermo J., et al., "In vivo Endoscopic Optical Biopsy with Optical Coherence Tomography", Science, New Series, vol. 276, pp. 2037-2039. (Jun. 27, 1997).

Thielen, P.A., et al, "Small-core As—Se fiber for Raman amplification", Optics Letters, vol. 28, No. 16, pp. 1406-1408. (2003).

Thongtrangan, Issada, et al., "Minimally invasive spinal surgery: a historical perspective", Neurosurg. Focus, vol. 16, Article 13, pp. 1-10. (Jan. 2004).

Thorne, A., et al., 2002. "A pilot study of long-term effects of a novel obesity treatment: omentectomy in connection with adjustable gastric banding," Intl. J. Obesity 26: 193-9. (2002).

Tittel, et al., "Mid-Infrared Laser Applications in Spectroscopy" pp. 445-463. (2003).

Tombelaine, Vincent, et al., "Ultra wide band supercontinuum generation in air-silica holey fibers by SHG-induced modulation instabilities", Optics Express, vol. 13, No. 19, pp. 7399-7404. (Sep. 19, 2005).

Travers, J.C., "Extended blue supercontinuum generation in cascaded holey fibers", Optics Letters, vol. 30, No. 23, pp. 3132-3134. (Dec. 1, 2005).

Travers, J.C., et al., "Extended continuous-wave supercontinuum generation in a low-water-loss holey fiber", Optics Letters, vol. 30, No. 15, pp. 1938-1940. (Aug. 1, 2005).

Unterhuber, A., et al., "Advances in broad bandwidth light sources for ultrahigh resolution optical coherence tomography", Physics in Medicine and Biology, Phys. Med. Biol. 49, pp. 1235-1246. (2004).

(56) References Cited

OTHER PUBLICATIONS

Urban, J.P.G., et al., "The Nucleus of the Intervertebral Disc from Development to Degeneration", Amer. Zool., vol. 40, pp. 53-61. (2000).

Wang, Yimin, et al., "Ultrahigh-resolution optical coherence tomography by broadband continuum generation from a photonic crystal fiber", Optics Letters, vol. 28, No. 3, pp. 182-184. (Feb. 1, 2003).

Werle, Peter, et al., "Near- and mid-infrared laser-optical sensors for gas analysis", Optics and Lasers in Engineering 37, pp. 101-114. (2002).

Westbrook, Paul S., "Improved Supercontinuum Generation Through UV processing of Highly Nonlinear Fibers", Journal of Lightwave Technology, vol. 23, No. 1, pp. 13-18. (Jan. 2005).

Wuthrich, Stefan, et al., "Optical damage thresholds at 2.94 μm in fluoride glass fibers", Applied Optics, vol. 31, No. 27, pp. 5833-5837.(Sep. 20, 1992).

Xie, T.Q., et al., "Detection of tumorigenesis in urinary bladder with optical coherence tomography: optical characterization of morphologial changes", Optics Express, vol. 10, No. 24, pp. 1431-1443. (Dec. 2, 2002).

Xie, Tuqiang, et al., "Endoscopic optical coherence tomography with a modified microelectromechanical systems mirror for detection of bladder cancers", Applied Optics, vol. 42, No. 31, pp. 6422-6426. (Nov. 1, 2003).

Povazay, B., et al., "Supermicrometer axial resolution optical coherence tomography," Optics Letters, vol. 27, No. 20, pp. 1800-1802. (Oct. 15, 2002).

Pitombo, C., et al., 2006. "Amelioration of diet-induced diabetes mellitus by removal of visceral fat" J. Endocrinol. 191: 699-706.

Poulos, S.P., et al., 2010. "The development and endocrine functions of adipose tissue" Molec. Cell. Endocr 323: 20-34.

Ramesh, et al., "FTIR Microscopic Studies on Normal, Polyp, and Malignant Human Colonic Tissues" Subsurface Sensin technologies and Applications vol. 2, No. 2, 2001.

Ruiz-Esparza, et al., "Near Painless, Nonablative, Immediate Skin contraction Induced by Low-Fluence irradiation with New Infrared Device: A Report of 25 Patients." Dermatol Surg 2006; 32: pp. 601-610.

Schwarzmaier, et al., . "MR-Guided Laser Irradiation of Recurrent Glioblastomas." J. Magn. Reson. Imaging 2005;22:799-803.

Schwarzmaier, et al., "MR-guided laser-induced interstitial thermotherapy of recurrent glioblastoma multiforme: Preliminary results in 16 patients." European Journal of Radiology 59 (2006) pp. 208-215.

Shen, et al., 2006. "Waist circumference correlates with metabolic syndrome indicators better than percentage fat." Obesity 14: 727-36.

Shi, H., et al., 2007. "The effect of fat removal on glucose tolerance is depot specific in male and female mice" Am. J. Physiol. Endocrinol. Metab. 293: E1012-20.

Sjöstrand, M., et al., 2009. "Neuroendocrine mechanisms in insulin resistance." Molec. Cell. Endocr. 297: 104-11.

Taub, et al., "Multicenter Clinical Perspectives on a Broadband Infrared Light Device for Skin Tightening." Journal of Drugs in Dermatology. Sep. 2006. vol. 5, Issue 8.

Tearney, G.J., et al., "Scanning single-mode fiber optic catheter-endoscope for optical coherence tomography"; Apr. 1, 1996; vol. 21, No. 7; Optics Letters.

Office Action for European Patent Application No. 10798941.0 dated Apr. 6, 2016.

Aaviksoo, J., et al., "Observation of optical precursors at pulse propagation in GaAs", Physical Review A, vol. 44, No. 9, pp. R5353-R5356. (May 21, 1991).

Abeeluck, Akheelesh K., et al., "Continuous-wave pumping in the anomalous-and normal-dispersion regimes of nonlinear fibers for supercontinuum generation", Optics Letters, vol. 30, No. 1, pp. 61-63. (Jan. 1, 2005).

Asobe, Masaki, "Nonlinear Optical Properties of Chalcogenide Glass Fibers and Their Application to All-Optical Switching", Optical Fiber Technology, vol. 3, Article No. OF970214, pp. 142-148. (1997).

Asobe, Masaki, et al., "Third-order nonlinear spectroscopy in As2S3 chalcogenide glass fibers", J. Appl. Phys. 77 (11), pp. 5518-5523. (Jun. 1, 1995).

Avdokhin, A. V., et al., "Continuous-wave, high-power, Raman continuum generation in holey fibers", Optics Letters, vol. 28, No. 15, pp. 1353-1355. (Aug. 1, 2003).

Baruch, "What every kertoconus (KC) patient should know about KC and New Laser Treatments for KC" (2004).

Beck, Mattias, et al., "Continuous Wave Operation of a Mid-Infrared Semiconductor Laser at Room Temperature," Science, vol. 295, www.sciencemag.org, pp. 301-305. (Jan. 11, 2002).

Bizheva, K., et al., Compact, broad-bandwidth fiber laser for sub-2-μm axial resolution optical coherence tomography in the 1300-nm wavelength region, Optics Letters, vol. 28, No. 9, pp. 707-709. (May 1, 2003).

Boppart, Stephen A., et al., "Imaging developing neural morphology using optical coherence tomography", Journal of Neuroscience Methods 70, pp. 65-72. (1996).

Boppart, Stephen A., et al., "Noninvasive assessment of the developing Xenopus cardiovascular system using optical coherence tomography" Proc. Natl. Acad. Sci. USA, vol. 94, pp. 4256-4261. ( Apr. 1997).

Borrelli, N. F., et al., "Resonant and non-resonant effects in photonic glasses", Journal of Non-Crystalline Solids 185, pp. 109-122. (1995).

Boult, Maggi, et al., "Percutaneous Endoscopic Laser Discectomy", Systematic Review, Aust. N.Z.J. Surg., vol. 70, pp. 475-479. (Apr. 7, 2000).

Boult, Maggi, et al., "Systematic Review of Percutaneous Endoscopic Laser Discectomy: Update and Re-appraisal", Australian Safety and Efficacy Register of New Interventional Procedures—Surgical Report No. 5, 49 pages. ( Feb. 2000).

Bowler, "Collagen and Fat Injections for Smoother Skin" <http://www.docstoc.com/docs/5459100/Collagen-And-Fat-Injections-For-Smoother-Skin-This-E-Book> (2006).

Busse, Lynda E., et al., "Design Parameters for Fluoride Multimode Fibers", Journal of Lightwave Technology, vol. 9, No. 7, pp. 828-831 (Jul. 1991).

Camacho, Nancy P., et al., "FTIR Microscopic Imaging of Collagen and Proteoglycan in Bovine Cartilage," Biopolymers (Biospectroscopy), vol. 62, pp. 1-8. (2001).

Caplan, et al., "Near-Infrared Spectroscopy for the detection of Vulnerable coronary Artery Plaques." JACC vol. 47, No. 8 Suppl C Apr. 18, 2006: C92-6.

Cardinal, T., et al., "Non-linear optical properties of chalcogenide glasses in the system As—S—Se", Journal of Non-Crystalline Solids 256 & 257, pp. 353-360. ( 1999).

Champert, Pierre-Alain, et al., "White-light supercontinuum generation in normally dispersive optical fiber using original multi-wavelength pumping system", Optics Express, vol. 12, No. 19, pp. 4366-4371. (Sep. 20, 2004).

Choi, Joon Y., et al., "Thermal, Mechanical, Optical, and Morphologic Changes in Bovine Nucleus Pulposus Induced by Nd:YAG ( a = 1.32 μm) Laser Irradiation", Lasers in Surgery and Medicine, vol. 28, pp. 248-254. ( 2001).

Choi, Seung-Ho., et al., "Observation of Optical Precursors in Water", Physical Review Letters, vol. 92, No. 19, pp. 193903-1-193903-3. ( May 14, 2004).

"Ciliary muscle" Wikipedia,the free encyclopedia <http://en.wikipedia.org/wiki/Ciliary_muscle.> (2009).

Coen, Stephane, et al., "Supercontinuum generation by stimulated Raman scattering and parametric four-wave mixing photonic crystal fibers", J. Opt. Soc. Am. B, vol. 19, No. 4, pp. 753-764. ( Apr. 2002).

D'Amico, Anthony V., et al., "Optical Coherence Tomography As a Method for Identifying Benign and Malignant Microscopic Structures in The Prostate Gland", Basic Science, Urology 55 (5), pp. 783-787. (2000).

De Boer, Johannes F., et al., "Determination of the depth-resolved Stokes parameters of light backscattered from turbid media by use

(56) References Cited

OTHER PUBLICATIONS of polarization-sensitive optical coherence tomography", Optics Letters, vol. 24, No. 5, pp. 300-302. (Mar. 1, 1999).
De Boer, Johannes F., et al., "Imaging thermally damaged tissue by polarization sensitive optical coherence tomography", Optics Express 212, vol. 3, No. 6, pp. 212-218. (Sep. 14, 1998).
Demerican, Ayhan, et al., "Supercontinuum generation by the modulation instability", Optics Communications 244, pp. 181-185. (2005).
Desthieux, B., et al., "111 kW (0.5 mJ) pulse amplification at 1.5 μm using a gated cascade of three erbium-doped fiber amplifiers," Appl. Phys. Lett. vol. 63, pp. 586-588. ( Aug. 2, 1993).
Drexler, Wolfgang, "Ultrahigh-resolution optical coherence tomography", Journal of Biomedical Optics, vol. 9, No. 1, pp. 47-74. (Jan./Feb. 2004).
Dubois, A., "Three-dimensional cellular-level imaging using full-field optical coherence tomography", Physics in Medicine and Biology, Phys. Med. Biol. 49, pp. 1227-1234. (2004).
Dudley, John M., et al., "Supercontinuum generation in air-silica microstructured fibers with nanosecond and femtosecond pulse pumping", J. Opt. Soc. Am. B, vol. 19, No. 4, pp. 765-771 (Apr. 2002).
Edwards, Glenn, et al., "Tissue ablation by a free-electron laser tuned to the amide II band", Nature, vol. 371, pp. 416-419 (Sep. 29, 1994).
Edwards, Glenn S., et al., "Advantage of the Mark-III FEL for biophysical research and biomedical applications", J. Synchrotron Rad. vol. 10, pp. 354-357. (2003).
Edwards, G. S., et al., Review Article, "Free-electron-laser-based biophysical and biomedical instrumentation", Review of Scientific Instruments, vol. 74, No. 7, pp. 3207-3245. (Jul. 2003).
Falk, Peter, et al., "Supercontinuum generation in a photonic crystal fiber with two zero-dispersion wavelengths tapered to normal dispersion at all wavelengths", Optics Express, vol. 13, No. 19, pp. 7535-7540. (Sep. 19, 2005).
Faralli, S., et al., "Impact of Double Rayleigh Scattering Noise in Distributed Higher Order Raman Pumping Schemes", IEEE Photonics Technology Letters, vol. 15, No. 6, pp. 804-806. (Jun. 2003).
Fedotova, O., et al., "Supercontinnum generation in planar rib waveguides enabled by anomalous dispersion", Optics Express, vol. 14, No. 4, pp. 1512-1517. ( Feb. 20, 2006).
Genty, G., et al., "Enhanced bandwidth of supercontinuum generated in microstructured fibers", Optics Express, vol. 12, No. 15, pp. 3471-3480. (Jul. 26, 2004).
Genty, G., et al., "Supercontinuum generation in large mode-area microstructured fibers", Optics Express, vol. 13, No. 21, pp. 8625-8633. (Oct. 17, 2005).
Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, pp. 33-37. (2001).
Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, pp. 91-93.(Jan. 1, 2006).
Hamilton, James D., et al., "High Frequency Optoacoustic Arrays Using Etalon Detection", IEEE Transactions on Ultrasonics, Ferroelectrics, and Frequency Control, vol. 47, No. 1, pp. 160-169. (Jan. 2000).
Hamilton, James D., et al., "High Frequency Ultrasound Imaging Using an Active Optical Detector", IEEE Transactions on Ultrasonics, Ferroelectrics, and Frequency Control, vol. 45, No. 3, pp. 719-727. (May 1998).
Hamilton, James D., et al., "High Frequency Ultrasound Imaging with Optical Arrays", IEEE Transactions on Ultrasonics, Ferroelectrics, and Frequency Control, vol. 45, No. 1, pp. 216-235. ( Jan. 1998).
Harbold, J. M., "Highly nonlinear As—S—Se glasses for all-optical switching", Optics Letters, vol. 27, No. 2, pp. 119-121. (Jan. 15, 2002).
Harbold, Jeffrey M., et al., "Highly Nonlinear Ge—As—Se and Ge—As—S—Se Glasses for All-Optical Switching", IEEE Photonics Technology Letters, vol. 14, No. 6, pp. 822-824. ( Jun. 2002).
Harrington, James A., "Infrared Fiber Optics", OSA Handbook, vol. III, to be published by McGraw Hill. (Jan. 22, 2004).
Hilligsoe, Karen Marie, et al., "Supercontinuum generation in a photonic crystal fiber with two zero dispersion wavelengths", Optics Express, vol. 12, No. 6, pp. 1045-1054. ( Mar. 22, 2004).
Hori, Takashi, et al., Experimental and numerical analysis of widely broadened supercontinuum generation in highly nonlinear dispersion-shifted fiber with a femtosecond pulse, J. Opt. Soc. Am. B, vol. 21, No. 11, pp. 1969-1980. (Nov. 2004).
Hori, Takashi, et al., "Flatly broadened, wideband and low noise supercontinuum generation in highly nonlinear hybrid fiber", Optics Express, vol. 12, No. 2, pp. 317-324.(Jan. 2004).
Carr, C. et al., "Strategic plan for minimally invasive fiber laser device applied to refractory type 2 diabetes. Research project of Team 14 of the Executive Multidisciplinary Action Projects, Executive Masters of Business degree program, University of Michigan Ross School of Business" (Aug. 2010), pp. 124.
Couillard, C., et al., 1999. "Gender difference in postprandial lipemia: importance of visceral adipose tissue" accumulation. Arteriosci. Thromb. Vasc Biol. 19: 2448-55.
Couillard, C., et al., 1997. "Plasma leptin concentrations: gender differences and associations with metabolic risk factors for cardiovascular disease" Diabetologia 40: 1178-84.
Deckelbaum, Lawrence, System Design Considerations for Lase Angioplasty; Texas Heart Institute Journal; 1989; 16: 150-7.
Despres, J.P., et al., 2006. "Abdominal obesity and metabolic syndrome" Nature 444: 881-7.
Dos Santos, et al., 2005. "Relationship of body fat distribution by waist circumference, dual-energy X-ray absorptiometry and ultrasonography to insulin resistance by homeostasis model assessment and lipid profile in obese and non-obese postmenopausal women" Gynecol. Endocrin 21: 295-301.
Fabbrini, et al., 2010. "Surgical removal of omental fat does not improve insulin sensitivity and cardiovascular risk factors in obese adults." Gastroenterology 139: 448-55.
Frayn, K.N. 2000. "Visceral fat and insulin resistance—causative or correlative." Brit. J. Nutrition 83: S71-7.
Fu, Henry L., et al., "Flexible miniature compound lens design for high-resolution optical coherence tomography balloon imaging catheter", Journal of Biomedical Optics; Nov./Dec. 2008; vol. 13(6).
Gabriely, I., et al., 2003. "Surgical removal of visceral adipose tissue: effects on insulin action" Pathogen. Type 2 Diabetes Mellitus 3: 201-6.
Galic, S., et al., 2010. "Adipose tissue as an endocrine organ" Molec. Cell. Endocr. 316: 129-39.
Gibson, et al., "Endovenous Laser Treatment of Varicose Veins." Surg Clin N Am 87 (2007) 1253-1265.
GLASER pediatric research network obesity study group. 2010. "Intraperitoneal fat and insulin resistance in obese adolescents" Obesity 18: 402-9.
George, et al., "Ablative fractional photothermolysis—A novel step in skin resurfacing" Medical laser Application 23 (2008) 93-98.
Herrera, M. F., et al., 2010. "Potential additional effect of omentectomy on metabolic syndrome, acute-phase reactants, and inflammatory mediators in grade III obese patients undergoing lapasoscopis roux-en-Y gastric bypass." Diabetes Care 33: 1413-8.
http://www.vanderbilt.edu/New/research/ravf96/ravf98_7html. FEL reaches brain tumors too risky for traditional surgery. Retrieved Oct. 6, 2010.
Huang, et al., "Plasma leptin is associated with insulin resistance independent of age, body mass index, fat mass, lipids, and pubertal development in nondiabetic adolescents." International Journal of Obesity (2004) 28, 470-475.
Islam, M.N. "Raman amplifiers for telecommunications 1: Physical principles" Springer-Verlag New York Inc. 2003. pp. 298.
Jarman, Richard H., "Novel optical fiber lasers", Current Opinion in Solid State and Materials Science 1996, pp. 199-203.
Ke, et al., "Mid-infrared absorption spectroscopy and differential damage in vitro between lipids and proteins by an all-fiber-

(56) References Cited

OTHER PUBLICATIONS integrated supercontinuum laser," Optics Express, Jul. 20, 2009, vol. 17, No. 15 pp. 12627-12640.
"KERATOCONUS" Wikipedia, the free encyclopedia. Web Oct. 26, 2008 http://en.wikipedia.org/wiki/Keratoconus.
Klein, S. 2010 "Is visceral fat responsible for the metabolic abnormalities associated with obesity?: implications of omentectomy" Diabetes Care 33: 1693-4.
Koh, et al., "Visible and near infrared autofluorescence and hyperspectral imaging spectroscopy for the investigation of colorectal lesions and detection of exogenous fluorophores." Proc. of SPIE (2009) vol. 7169 7169E-1.
Kohler, et al., "Characterization of lipid extracts from brain tissue and tumors using Ramana spectroscopy and mass spectrometry." Anal Bioanal Chem (2009) 393: 1513-1520.
Kompanowska-Jezierska, et al., "Early effects of renal denervation in the anaesthetised rat: natriuresis and increased cortical blood flow" Journal of Physiology 2001, 531 2: 527-534.
Kondepati, et al., "Application of near-infrared spectroscopy for diagnosis of colorectal cancer in resected human tissue specimens." Vibrational Spectroscopy 44 (2007) pp. 236-242.
Kondepati, et al., "CH-overtone regions as diagnostic markers for near-infrared spectroscopic diagnosis of primary cancers in human pancreas and colorectal tissue." Anal Bioanal Chem (2007) 387: 1633-641.
Kondepati, et al., "Near-infrared spectroscopic detection of human colon diverticulitis: A pilot study" Vibrational/Spectroscopy 44 (2007) 56-61.
Kondepati, et al., "Recent applications of near-infrared spectroscopy in cancer diagnosis and therapy." Anal bioanal Chem (2008) 390: 125-139.
Kopczynski, et al., "Miniature, "eye-safe" solid-state lasers." SPIE (1997) vol. 3186, pp. 292-295.
Krum, et al., Catheter-based renal sympathetic denervation for resistant hypertensions: a multicentre safety and proof-of-principle cohort study: Lancet 2009; 373: 1275-81.
Kumar, et al., 2008. "Power adjustable visible supercontinuum generation using amplified nanosecond gain-switched laser dioide" Opt. exp. 16: 6194-6201.
Kux, E. "The Endoscopic approach to the vegetative nervous system and its therapeutic possibilities: especially in duodenal ulcer, angina pectoris, hypertension and diabetes" Dis Chest 1951, 20: 139-147.
LaRosa, J., 2007 "US weight loss & diet control market (9th edition)." Market Data Enterprises, Tampa, FL pp. 393.
Lebovitz, H.E., et al, 2005. "Point: Visceral adiposity is causally related to insulin resistance" Diabetes Care 28: 2322-5.
Lee, et al., "Waist cirumference, dual-energy X-ray absortiometrically measured abdominal adiposity, and computed tomographically derived intra-abdominal fat area on detecting metabolic risk factors in obese women." Applied nutritional investigation. Nutrition 24 (2008) pp. 625-631.
Lee, Kye-Sung, et al., "2mm Catheter Design for Endoscopic Optical Coherence Tomography"; International Optical Design Conference 2006; SPIE-OSA/vol. 6342 63420E-1.
Leertouwer, et al., "In-vitro validation, with histology, of intravascular ultrasound in renal arteries" Journal of Hypertension 1999, 17:271-277.
Li, et al., "Use of Fourier-transform infrared spectroscopy to rapidly diagnose gastric endoscopic biopsies." World J Gastroenterol 2005;11(25):3842-3845. ISSN 1007-9327.
Lottati, M., et al., 2009. "Greater omentectomy improves insulin sensitivity in non-obese dogs." Obesity 17: 674-80.
Lyra, et al., "Outcomes of radio frequency in advanced keratoconus." J Cataract Refract Surg 2007; 33: pp. 1288-1295.
McCartney, "Heat Contraction of Elastic Tissue" 1913. <ep.physoc.org>.
Meemon, Panomsak, et al., "Optical design of a dynamic focus catheter for high-resolution endoscopic optical coherence tomography"; Applied Optics; vol. 47, No. 13; May 1, 2008.
Miles, J.M., et al., 2005. "Counterpoint: Visceral adiposity is not causally related to insulin resistance," Diabetes Care 28: 2326-8.
Misra, A., et al., 2004. "High prevalence of insulin resistance in postpubertal Asian Indian children is associated with adverse truncal body fat patterning, abdominal adiposity and excess body fat" Int. J. Obesity 28: 1217-26.
Mu, Xiaojing, et al., "MEMS micromirror integrated endoscopic probe for optical coherence tomography bioimaging"; Sensors and Actuators A 168 (2011) 202-212.
Muller, et al., "IR-Spectroscopy for Tissue Differentiation in the Medical Field." Laser Physics, vol. 9, No. 1, 1999, pp. 348-356.
"MYELIN", Wikipedia, the Free Encyclopedia. Web. Oct. 4, 2010. <http://en.wikipedia.org/wiki/Myelin>.
Nilsson, et al., "Near infrared Spectrochimica diffuse reflection and laser-induced fluorescence spectroscopy for mycardial tissue characterization." Acta Part A 53 (1997) 1901-1912.
Orringer, et al., "Connective Tissue Remodeling Induced by Carbon Dioxide Laser Resurfacing of Photodamaged Human Skin." Arch Dermatol. 2004;140:1326-1332.
Agger, et al., "Emission and absorption cross section of thulium doped silica fibers." Jan. 9, 2006/vol. 14, No. 1/OPTICS express.
Agger, et al., "Single-frequency thulium-doped distributed feedback fiber laser" Jul. 1, 2004/vol. 29, 13/Optics Letters.
Agger, et al., "Single frequency thulium doped silica DBF fiber laser at 1735 nm," Proc of SPIE (2004) vol. 5335:277-284.
Alhalabi, et al., "Nonablative Skin tightening: A Review of the Literature." Elixir Institute of Regenerative Medicine, San Jose, CA Clinical Medicine: Dermatology 2009: 2 pp. 5-21.
Almedia, "Endovenous Ablation Without Anesthesia? Early experience with a new laser wavelength that is highly absorbable by water." Apr. 2009.
Anderson, et al., 2006. "Selective photothermolysis of lipid-rich tissues: a free electron laser study," Lasers Surg. Med. 38: 913-919.
Atzmon, G., et al., 2002. "Differential gene expression between visceral and subcutaneous fat depots." Horm. Metab. Res. 34: 622-8.
Bo, et al., "Body fat is the Main Predictor of Fibrinogen Levels in Healthy Non-obese Men." Metabolism, vol. 53, No. 8 Aug. 2004: pp. 984-988.
Bogle, "Fractionated Mid-Infrared Resurfacing" Semin Cutan Med Surg 27 (2008) pp. 252-258.
Boyko, E. J., et al., 2000. "Visceral adiposity and risk of type 2 diabetes: A prospective study among Japanese Americans." Diabetes Care 23: 1260-4.
"Cardiac Muscle" Wikipedia, the free encyclopedia. Web Nov. 30, 2009 en.wikipedia.org/wiki/Cardiac_muscle.
Examination Report for European Application No. 10 798 941.0 dated Feb. 25, 2015.
Canadian Office Action and Search Report for Canadian Application No. 2,786,262 dated Jul. 17, 2017.

\* cited by examiner

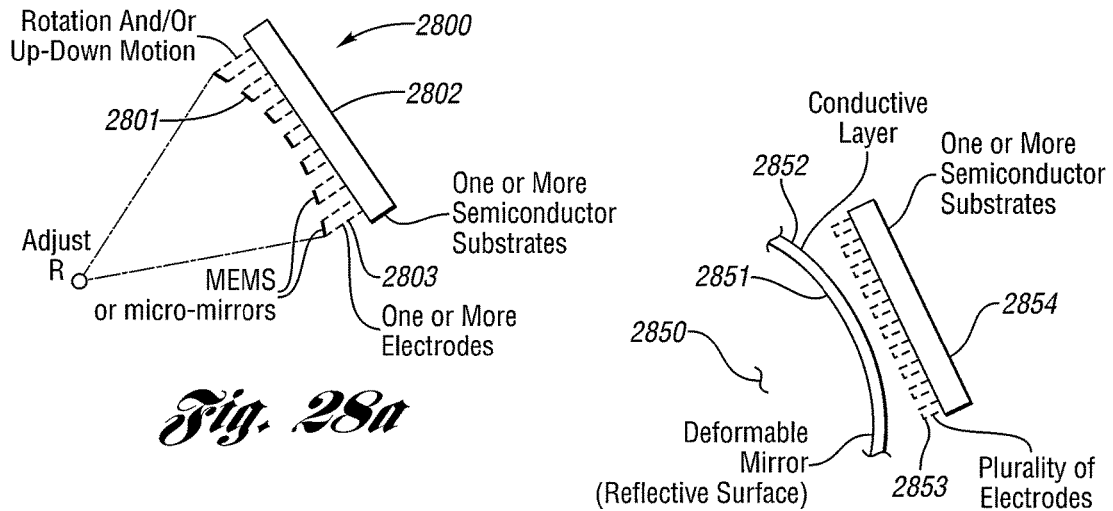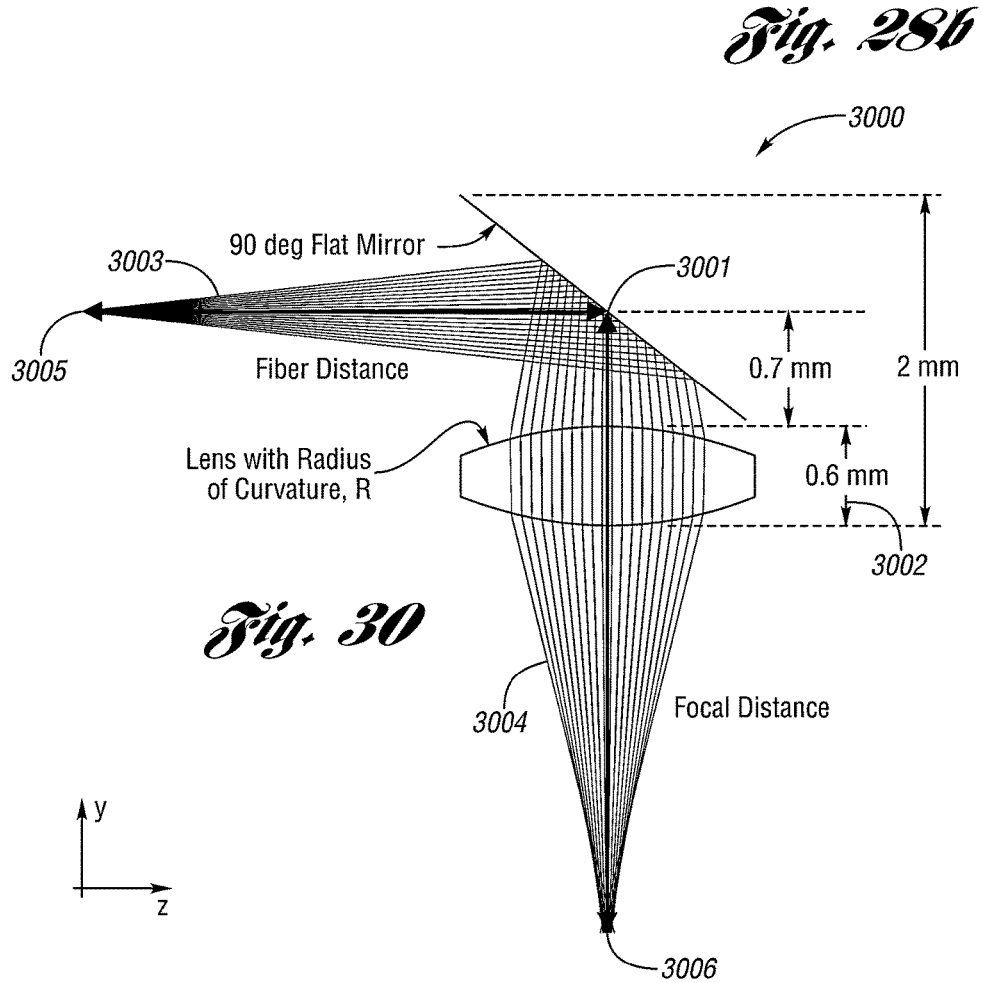

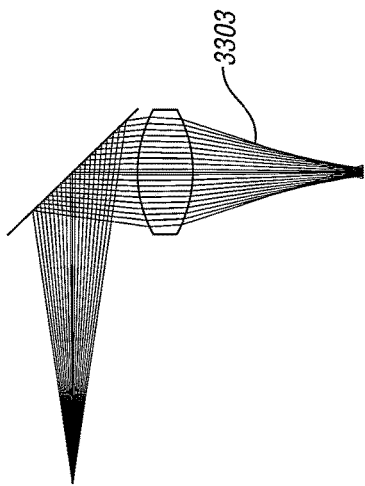
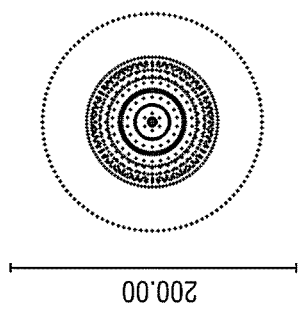
Fiber Distance = 3.5mm
Focal Distance = 3.1mm
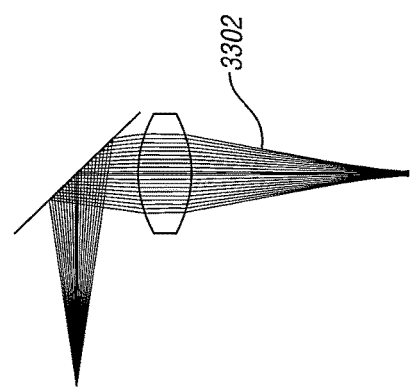
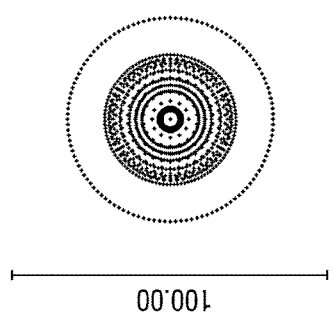
Fiber Distance = 2.5mm
Focal Distance = 3.8mm
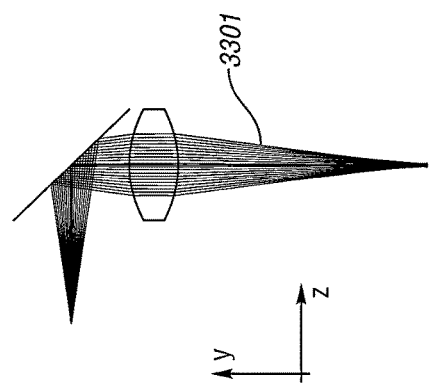
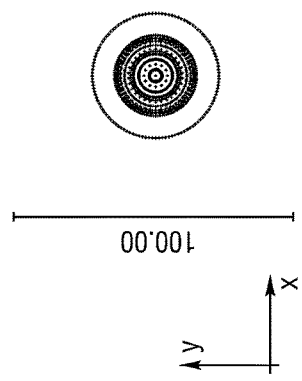
Fiber Distance = 2mm
Focal Distance = 4.3mm
Fig. 33

Balloon Head Deflated

Balloon Head Inflated

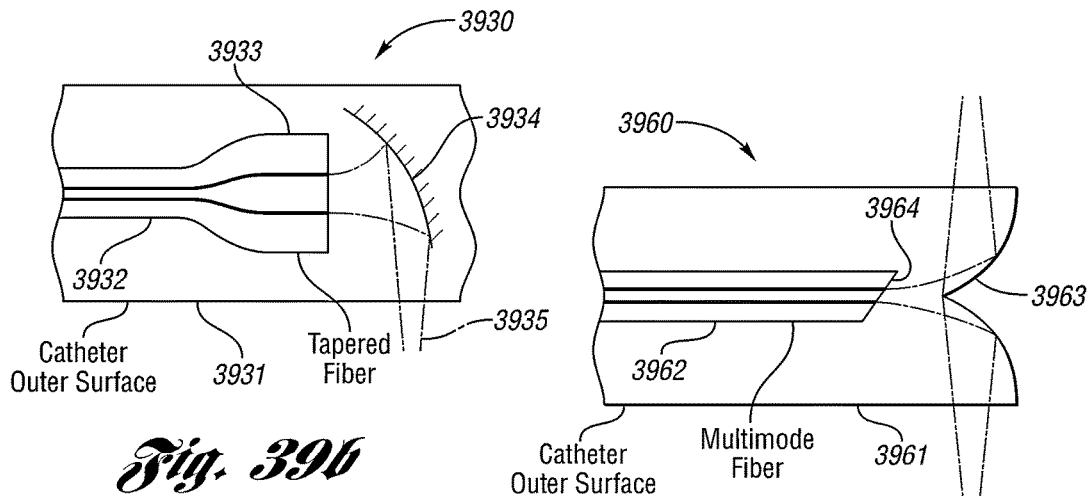
Fig. 39b
Fig. 39c
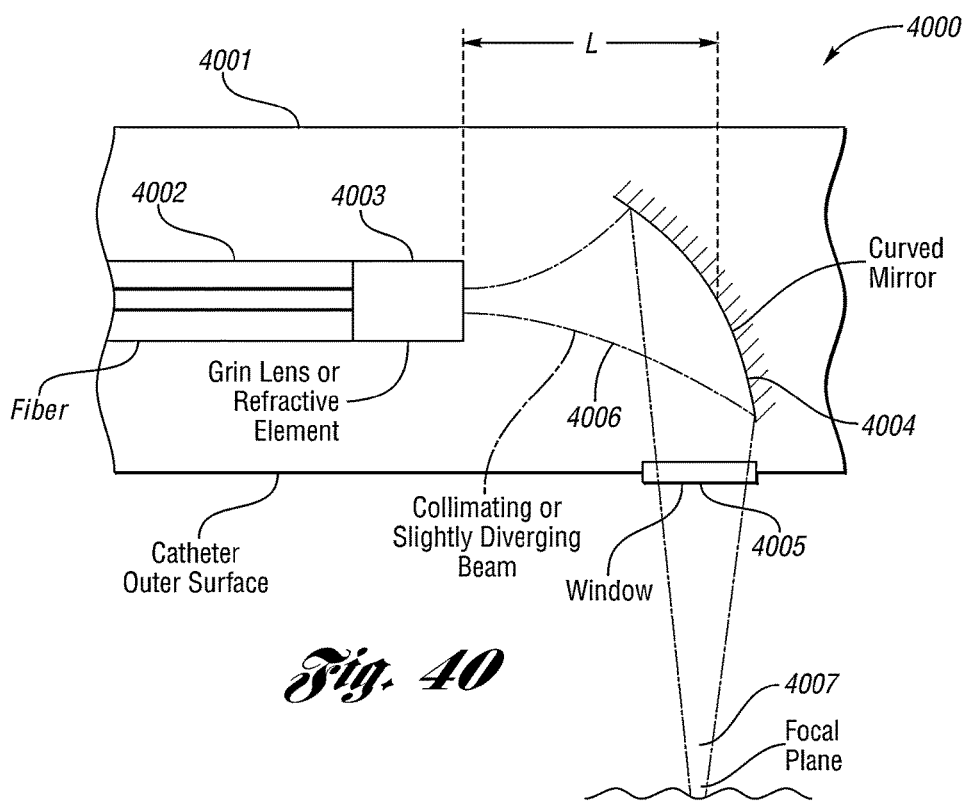
Fig. 40

LASER-BASED METHOD AND SYSTEM FOR SELECTIVELY PROCESSING TARGET TISSUE MATERIAL IN A PATIENT AND OPTICAL CATHETER ASSEMBLY FOR USE THEREIN

CROSS-REFERENCE TO RELATED APPLICATIONS

This application is a divisional of U.S. Ser. No. 13/215,837 filed Aug. 23, 2011, which is a continuation-in-part of PCT App. No. PCT/US2010/062467 filed Dec. 30, 2010, which claims the benefit of U.S. provisional patent application Ser. Nos. 61/335,456, 61/335,455, and 61/335,440 all filed Jan. 7, 2010, the disclosures of which are incorporated in their entirety by reference herein.

TECHNICAL FIELD

This invention relates in general to lasers and light sources for healthcare, medical, or bio-technology applications, and more particularly to systems, methods and optical catheters for therapeutically, selectively damaging or processing biological material associated with certain tissue types.

BACKGROUND

Many of the lasers that are used in healthcare, medical or bio-technology applications operated on the basis of absorption of the light in water. However, since water pervades most biological tissue, the medical lasers tend not to be selective to a particular tissue type. During medical procedures using such non-selective lasers, there can be additional risk and complications from unwanted collateral damage. Also, for laser wavelengths that are significantly absorbed by water, the light may not penetrate very far into the tissue. Consequently, lasers tend to treat only the surface of the tissue exposed to the light. Therefore, there exists a need for lasers and procedures based on light sources or lasers that can be selective and that can penetrate deeper into tissue.

Mid-infrared lasers, such as lasers that operate between approximately 1 and 10 microns, preferably between 1.2 and 4.5 microns, can be implemented that operate near absorption peaks of various tissues, such as adipose (e.g., fat, cholesterol, lipids), collagen and elastin. Moreover, the wavelength of the lasers can be selected to minimize water absorption and scattering through tissue. Thus, mid-infrared lasers tuned to optical absorption in particular tissue constituents can be used in one embodiment for selective damage in therapeutic procedures. In another embodiment, the optical absorption or reflection spectroscopy can be used as a diagnostic technique to differentiate between different tissue types. Moreover, by operating at mid-infrared wavelengths with less water absorption and tissue scattering, the penetration depth for the light can be increased to several millimeters, as an example. These features of mid-infrared light can be beneficial in a number of medical fields, including but not limited to ophthalmology, dermatology, cardiology and neurology as well as treatment of type 2 diabetes and other ailments associated with obesity.

The following U.S. patent references are related to at least one example embodiment of the present invention: U.S. Pat. Nos. 5,618,284; 5,779,696; 6,159,205; 6,251,103; 6,605,080; 6,986,764; 7,060,061; 7,633,673; 2008/0015557; 2009/0028193; and 2009/0054879.

SUMMARY

In a system embodiment, a system for selectively processing target tissue material in a patient includes a laser subsystem for generating an output laser beam. The system further includes a catheter assembly including at least one optical fiber having a proximal end coupled to the laser subsystem for guiding the output laser beam along a propagation path. The beam has optical and temporal properties and a predetermined selected wavelength between 900 nm and 2600 nm. The catheter assembly is sized to extend through an opening in a first part of the patient and to a tissue material processing site within the patient. The catheter assembly further includes a beam delivery and focusing subsystem having a focal distance and disposed in the propagation path and that accepts the output laser beam and positions the beam into at least one focused spot on the target tissue material disposed within a second part of the patient at the site based on distance to the target tissue material from a predetermined point on the propagation path at the site for a duration sufficient to allow laser energy to be absorbed by the target tissue material and converted to heat to produce a desired physical change in the target tissue material without causing undesirable changes to adjacent non-target material disposed within the second part of the patient. The target tissue material is characterized by an absorptive coefficient. The predetermined wavelength is selected to achieve a penetration depth into the second part of the patient of approximately one millimeter or more.

In an optical catheter assembly embodiment, an optical catheter assembly for use in a system for selectively processing target tissue material in a patient is provided. The assembly includes an elongated flexible housing. The assembly further includes an optical fiber disposed in the housing for guiding an output laser beam along a propagation path. The beam has optical and temporal properties and a predetermined selected wavelength between 900 nm and 2600 nm. The housing is sized to extend through an opening in a first part of the patient and to a tissue material processing site within the patient. The assembly still further includes a beam delivery and focusing subsystem having a focal distance and disposed in the propagation path that accepts the output laser beam and positions the beam into at least one focused spot on the target tissue material disposed within a second part of the patient at the site based on distance to the target tissue material from a predetermined point on the propagation path at the site for a duration sufficient to allow laser energy to be absorbed by the target tissue material and converted to heat to produce a desired physical change in the target tissue material without causing undesirable changes to adjacent non-target material disposed within the second part of the patient. The target tissue material is characterized by an absorptive coefficient. The predetermined wavelength is based on the absorptive coefficient of the target tissue material. The adjacent non-target material has an absorptive coefficient different from the absorptive coefficient of the target tissue material at the predetermined wavelength.

In a method embodiment, a laser-based method of selectively processing target tissue material in a patient is provided. The method includes generating and guiding an output laser beam along a propagation path. The beam has optical and temporal properties and a predetermined selected wavelength between 900 nm and 2600 nm. The path extends through an opening in a first part of the patient and to a tissue material processing site within the patient. The method further includes delivering and focusing the output laser beam into at least one focused spot on the target tissue material disposed within a second part of the patient at the site based on distance to the target tissue material from a predetermined point on the propagation path at the site for a duration sufficient to allow laser energy to be absorbed by the target tissue material and converted to heat to produce a desired physical change in the target tissue material without causing undesirable changes to adjacent non-target material disposed within the second part of the patient. The target tissue material is characterized by an absorptive coefficient. The predetermined wavelength is based on the absorptive coefficient of the target tissue material. The adjacent non-target material has an absorptive coefficient different from the absorptive coefficient of the target tissue material at the predetermined wavelength and the predetermined wavelength is selected to achieve a penetration depth into the second part of the patient of approximately one millimeter or more.

Depending on the specific features implemented, particular embodiments of the present invention may exhibit some, none, or all of the following technical advantages. Various embodiments may be capable of penetration deep into tissue. Some embodiments may be capable of penetrating several millimeters into such tissue.

Other technical advantages will be readily apparent to one skilled in the art from the following figures, description and claims. Moreover, while specific advantages have been enumerated, various embodiments may include all, some or none of the enumerated advantages.

BRIEF DESCRIPTION OF THE DRAWINGS

For a more complete understanding of the present invention, and for further features and advantages thereof, reference is now made to the following description taken in conjunction with the accompanying drawings, in which:

FIG. 5 adds the two curves of FIG. 4 to provide the resulting water absorption and scattering loss;

FIG. 27 are spot diagrams for corresponding different focal distances noted in FIG. 26a;

FIG. 28a is a side schematic view of an adaptive curved mirror comprising a plurality of controlled MEMS micromirrors;

FIG. 28b is a side schematic view of an adaptive curved mirror having a deformable reflective surface;

FIG. 30 is a side schematic view of a flat mirror with an associated focusing lens;

FIG. 33 are spot diagrams from corresponding different focal distances noted in FIG. 32;

FIG. 39b is a side schematic view, partially broken away, of a catheter having a tapered fiber;

FIG. 39c is a side schematic view, partially broken away, of a catheter having a multimode fiber;

FIG. 40 is a side schematic view, partially broken away, of a catheter with a grin lens or refractive element-tipped fiber;

DETAILED DESCRIPTION

Figure 1:
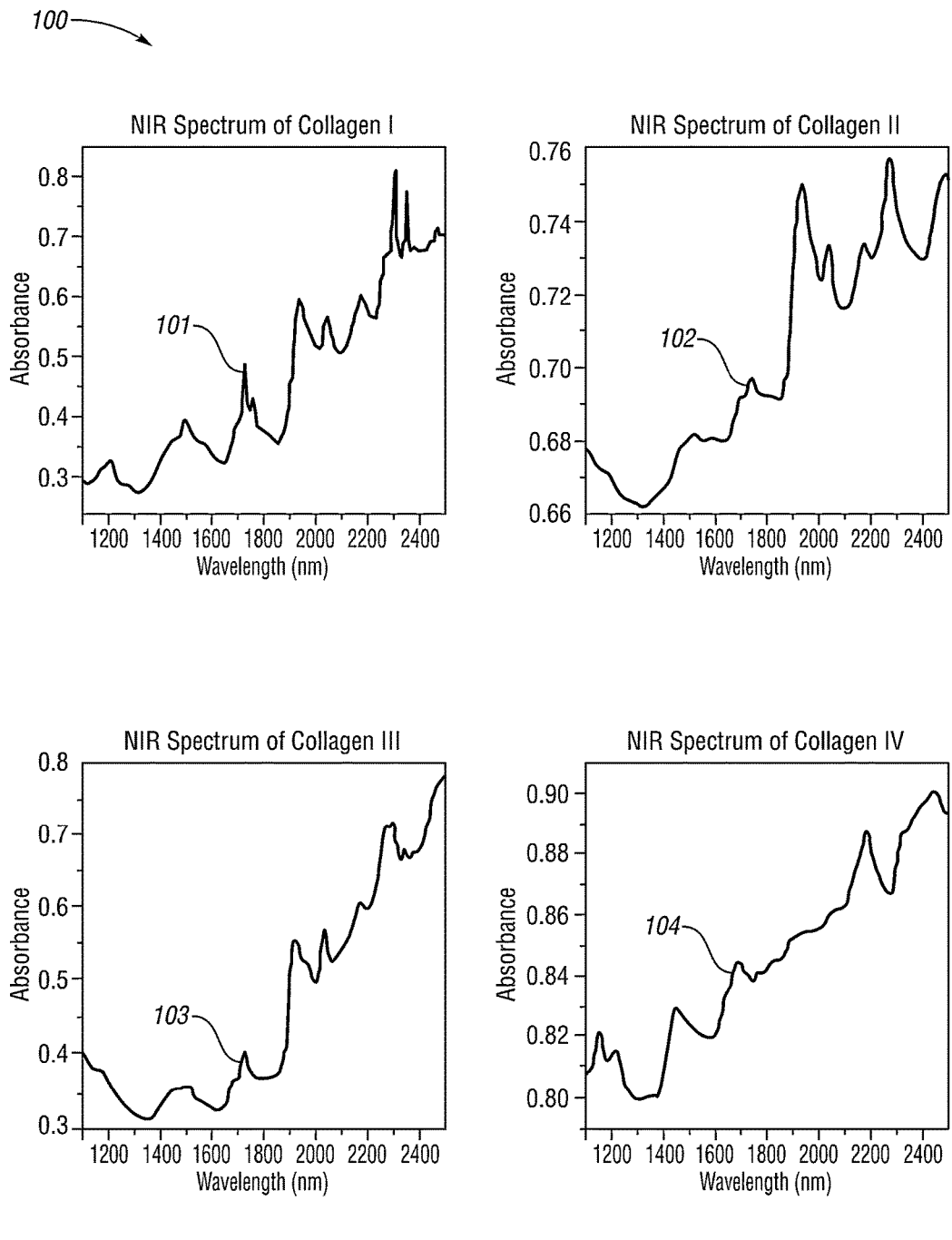
FIG. 1 illustrates the optical absorbance spectrum for four types of collagen in the mid-infrared wavelength range between 1200 nm (1.2 microns) and 2400 nm (2.4 microns); the upper left curve corresponds to the absorbance for collagen I, the upper right curve corresponds to the absorbance for collagen II, the lower left curve corresponds to the absorbance for collagen III, and the lower right curve corresponds to the absorbance for collagen IV.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Mid-infrared light sources can be used for diagnostics and therapeutics in a number of medical applications. For example, broadband light sources can advantageously be used for diagnostics, while narrower band light sources can advantageously be used for therapeutics. In one embodiment, selective absorption or damage can be achieved by choosing the laser wavelength to lie approximately at an absorption peak of particular tissue types. Also, by using mid-infrared wavelengths that minimize water absorption peaks and longer wavelengths that have lower tissue scattering, larger penetration depths into the biological tissue can be obtained. As an example, tissues such as adipose, collagen and elastin have absorption peaks in the mid-infrared wavelengths. In this disclosure, we define mid-infrared wavelengths as wavelengths in the range of 1 to 10 microns, more preferably wavelengths between about 1.2 and 4.5 microns.

As used throughout this document, the term "couple" and or "coupled" refers to any direct or indirect communication between two or more elements, whether or not those elements are physically connected to one another. In this disclosure, the term "damage" refers to affecting a tissue or sample so as to render the tissue or sample inoperable. For instance, if a particular tissue normally emits certain signaling chemicals, then by "damaging" the tissue is meant that the tissue reduces or no longer emits that certain signaling chemical. The term "damage" and or "damaged" may include ablation, melting, charring, killing, or simply incapacitating the chemical emissions from the particular tissue or sample. In one embodiment, histology or histochemical analysis may be used to inspect if a tissue or sample has been damaged.

As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or lightpipe. In one embodiment, the gain fiber may be doped with rare earth material, such as ytterbium, erbium, thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth or at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this document, the term "near 1720 nm" refers to one or more wavelengths of light with a wavelength value anywhere between approximately 1680 nm and 1760 nm. In a preferred embodiment, the term "near 1720 nm" refers to one or more wavelengths of light with a wavelength value anywhere between approximately 1700 nm and 1740 nm. Similarly, as used throughout this document, the term "near 1210 nm" refers to one or wavelengths of light with a wavelength value anywhere between approximately 1170 nm and 1250 nm. In a preferred embodiment, the term "near 1210 nm" refers to one or wavelengths of light with a wavelength value anywhere between approximately 1190 nm and 1230 nm.

To better understand the diagnostic and therapeutic applications, the optical spectra of a number of tissue types or tissue constituents are first reviewed.

Optical Spectra For Different Tissue Constituents

FIG. 1 illustrates the optical absorbance for different types of collagen 100 in the mid-infrared wavelength range between approximately 1200 and 2400 nm, which also corresponds to 1.2 to 2.4 microns. The upper left curve 101 is exemplary the absorption spectrum for collagen I, which can be one of the main constituents in the dermis of the skin as well as the cornea of the eye. Curve 102 corresponds to the absorbance for collagen II, curve 103 corresponds to the absorbance for collagen III, and curve 104 to the absorbance for collagen IV. In cardiology, the aorta comprises mostly type I and type III collagen. To be specific when discussing collagen spectra in this disclosure, the spectra for collagen I 101 will be used, unless stated otherwise. In the particular case of collagen I, there are local absorbance peaks near 1210 nm and 1720 nm. As further discussed below, these wavelength windows can be particularly interesting because of lower water absorption at these wavelengths.

Figure 2:
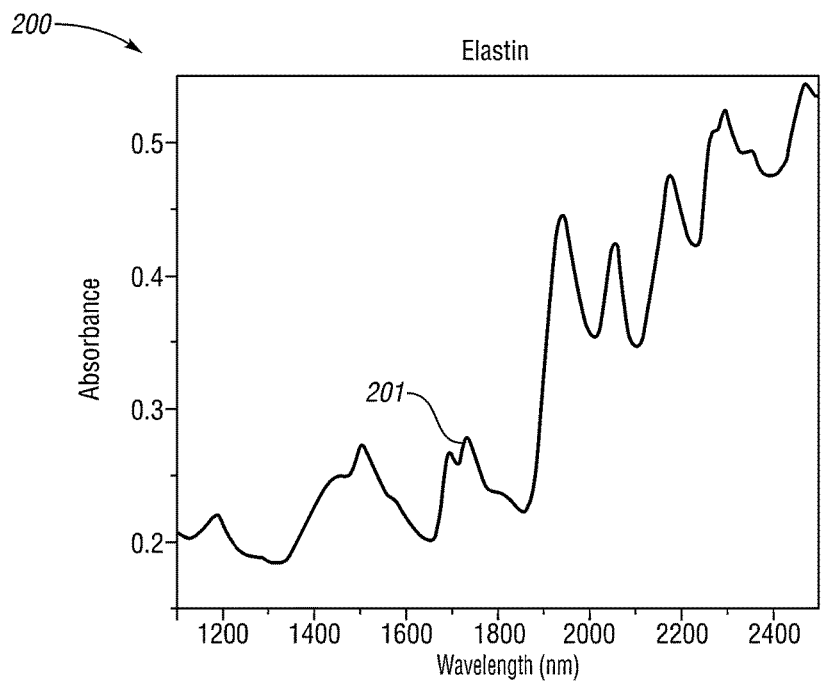
FIG. 2 illustrates the optical absorbance of elastin in the mid-infrared wavelength range between approximately 1200 nm and 2400 nm.

FIG. 2 illustrates the optical absorbance of elastin 201 in the mid-infrared wavelength range between approximately 1200 nm and 2400 nm. Elastin can be one of the main constituents of the dermis, and it gives the skin some of the elasticity and springy properties. Elastin can have a unique optical spectrum 200 that differentiates it from collagens 100. Despite the difference in absorbance shape from collagen I, there is also a local absorbance peak near 1720 nm.

Figure 3:
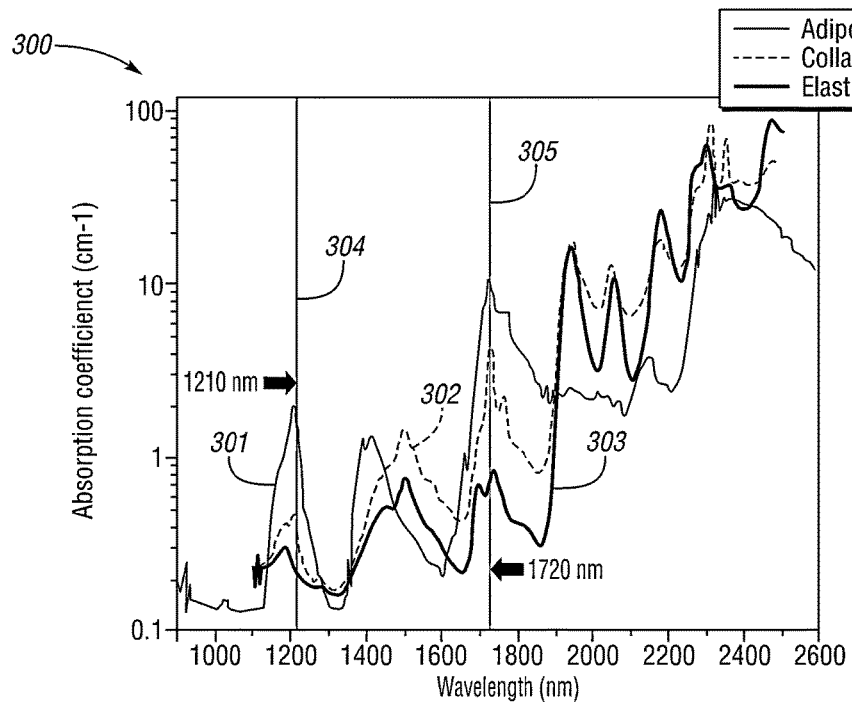
FIG. 3 overlaps the absorption coefficient of adipose tissue with collagen I and elastin; vertical lines are also drawn to highlight the wavelengths near 1210 nm and 1720 nm; the adipose absorption coefficient is shown on a calibrated scale, while the collagen and elastin are in arbitrary units.

FIG. 3 better illustrates similarities and differences in the mid-infrared spectra for collagen I 302 and elastin 303. The two absorbance curves are in arbitrary units, so the shapes and peaks in absorption can be compared, but the amplitudes of the absorption coefficient are arbitrary. Also shown are vertical lines demarking the wavelengths of approximately 1210 nm 304 and 1720 nm 305. Near 1720 nm, both the elastin and collagen have local absorption peaks that nearly coincide in wavelength. Whereas collagen has another local absorption peak near 1210 nm, the elastin local peak is about 25 nm shorter at approximately 1185 nm.

Another tissue type of interest is adipose, which includes fatty tissue and acids, lipids, and cholesterol. FIG. 3 overlaps the absorption coefficient of adipose tissue 301 with collagen 302 and elastin 303. It can be noted that adipose, collagen and elastin all show a local absorption peak near 1720 nm. Also, adipose and collagen have a local absorption peak near 1210 nm, although elastin has the local absorption peak closer to 1185 nm.

Blood is prevalent throughout the body, and it may be desirable to avoid absorption in blood to achieve selective absorption in certain tissue types. Most of the absorption in blood can be in the visible and ultraviolet wavelengths, and the absorption in hemoglobin is approximately transparent by approximately 1200 nm. Beyond this wavelength range in the mid-infrared, the absorption coefficient of blood closely resembles the absorption coefficient of water.

Figure 4:
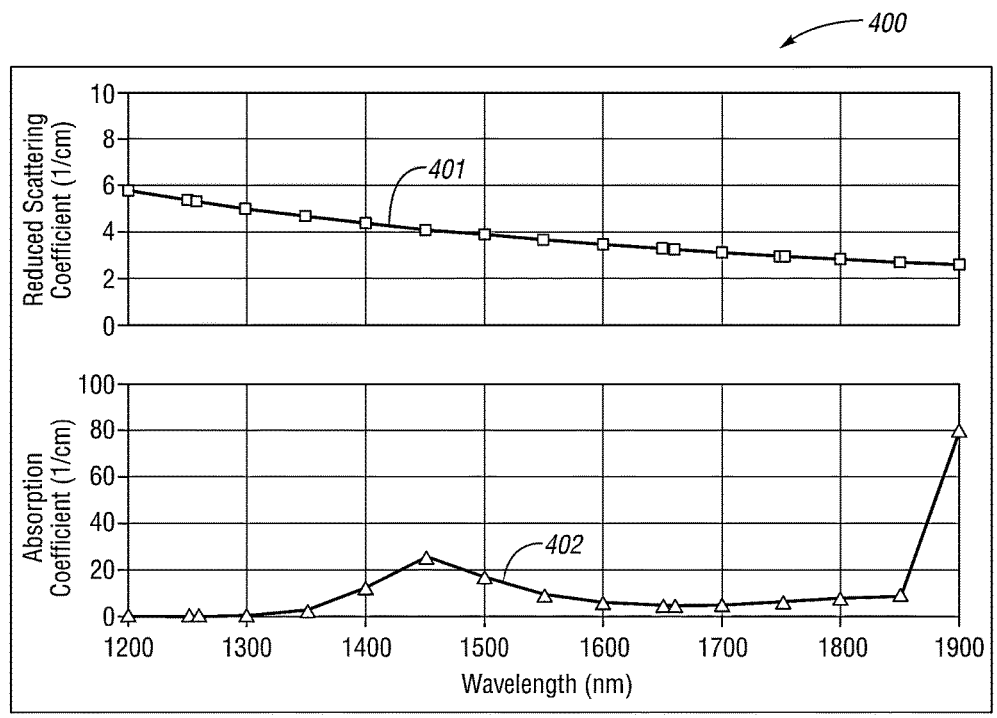
FIG. 4 illustrates separately the exemplary water absorption and scattering loss; the top of FIG. 4 is the reduced scattering coefficient through tissue such as dermis, while the bottom of FIG. 4 is the absorption coefficient of water.
Figure 5:
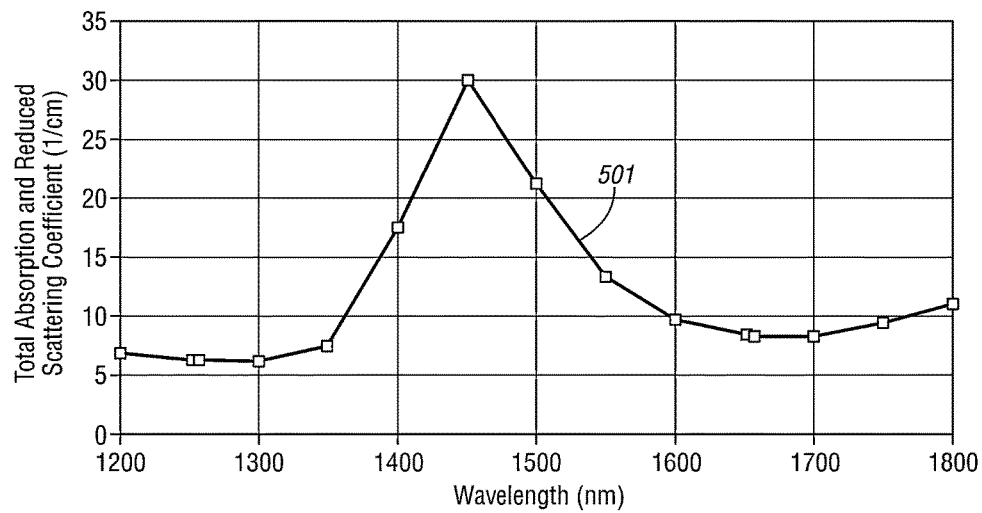
FIG. 5 illustrates exemplary the combined water absorption and scattering loss curves.

In general, to understand the propagation through and penetration into biological tissue, water absorption 402 and scattering loss 401 should be considered. FIG. 4 illustrates these two contributions to light attenuation separately, and then FIG. 5 adds the two curves to provide the resulting total absorption and reduced scattering coefficient 501. The bottom of FIG. 4 plots the absorption coefficient of water 402 in the mid-infrared wavelength range between 1200 and 1900 nm, and local peaks in water absorption are seen exemplary near 1450 nm and 1940 nm. In addition, the top of FIG. 4 plots the reduced scattering coefficient 401 as measured propagating through the dermis. In accordance with scattering theory, the scattering loss follows an approximate scaling law of the inverse of the square of the wavelength. Therefore, one advantage of using longer wavelengths can be that the scattering loss is reduced. FIG. 5, which is the sum of the two curves in FIG. 4, shows that there are relative minima in the total absorption and scattering 501 near 1210 nm (approximately 6.8 cm$^{-1}$) and 1720 nm (approximately 8.25 cm$^{-1}$).

Figure 6:
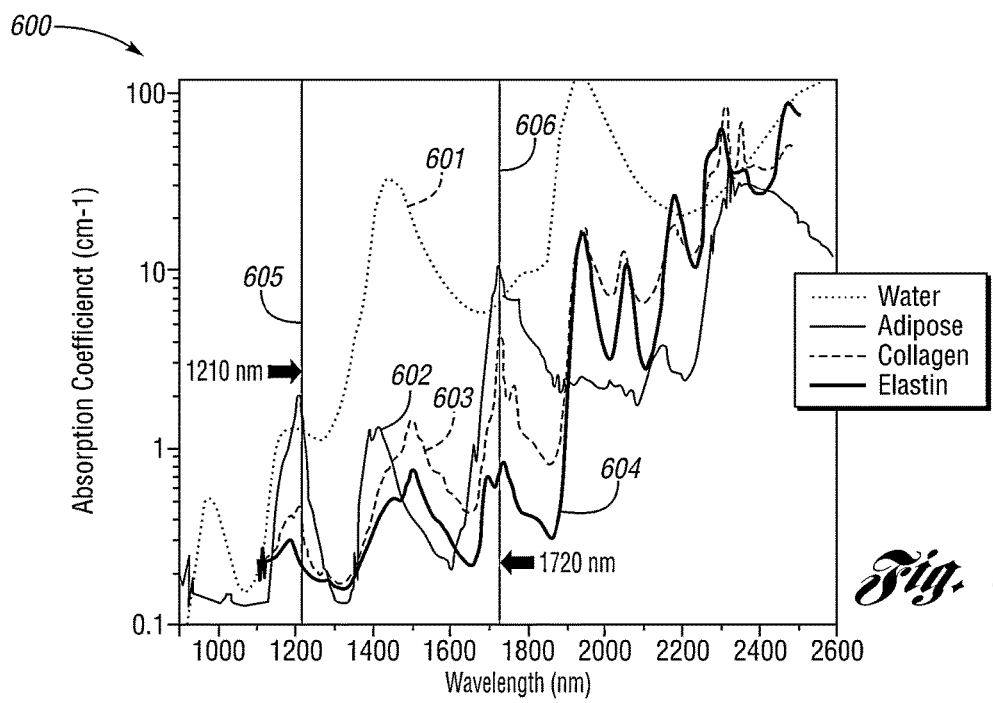
FIG. 6 illustrates the overlap of the absorption coefficients for water, adipose, collagen and elastin; vertical lines are also drawn to highlight the wavelengths near 1210 nm and 1720 nm; the adipose and water absorption coefficients are shown on a calibrated scale, while the collagen and elastin are in arbitrary units.

FIG. 6 illustrates the overlap of the absorption coefficients for water 601, adipose 602, collagen 603 and elastin 604. Note that the absorption curves for water 601 and adipose 602 are calibrated, whereas the absorption curves for collagen 603 and elastin 604 are in arbitrary units. Also shown are vertical lines demarcating the wavelengths near 1210 nm 605 and 1720 nm 606. As an example, the absorption coefficient for adipose 602 exceeds the water absorption 601 in the wavelength windows near 1210 nm and 1720 nm. However, near 1210 nm there is a local maximum in water absorption, while near 1720 nm the wavelength is in the vicinity of a minimum in water absorption. There are peaks in water absorption near 970 nm, 1190 nm, 1450 nm and 1940 nm, and there is also a large water peak near 3000 nm. Also, in general, the water absorption increases with increasing wavelength. With the increasing absorption beyond about 2000 nm, it may be difficult to achieve deeper penetration into biological tissue in the mid-infrared wavelengths beyond 2000 nm.

Although FIG. 6 can be useful for determining the material in which light of a certain mid-infrared wavelength will be absorbed, to determine the penetration depth of the light of a certain wavelength may also require the addition of scattering loss to the curves. For example, FIG. 7 modifies the figure by also including the scattering loss curve to the water absorption 701 (i.e., uses FIG. 5 rather than just the water absorption in the bottom of FIG. 4). Since the scattering loss can be significantly higher at shorter wavelengths, the comparison of adipose absorption 702 to loss propagating through water and tissue scattering 701 can be altered, particularly for wavelengths below approximately 1400 nm. In one embodiment, near the wavelength of 1720 nm (vertical line 706 shown in FIG. 7), the adipose absorption 702 can still be higher than the water plus scattering loss 701. For tissue that contains adipose, collagen and elastin, such as the dermis of the skin, the total absorption can exceed the light energy lost to water absorption and light scattering at 1720 nm. On the other hand, at 1210 nm the adipose absorption 702 can be considerably lower than the water plus scattering loss 701, particularly since the scattering loss can be dominant at these shorter wavelengths. As in FIG. 6, in FIG. 7 the absorption curves for water, scattering and adipose are calibrated, whereas the absorption curves for collagen and elastin are in arbitrary units.

One further consideration in choosing the laser wavelength is known as the "eye safe" window. In particular, wavelengths in the eye safe window may not transmit down to the retina of the eye, and therefore, these wavelengths may be less likely to create permanent eye damage. The mid-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering some surface. Hence, it can always be a good practice to use eye protection when working around lasers.

Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation. Thus, for example, wavelengths near 1210 nm do not fall in the eye safe window, while wavelengths near 1720 nm are within the eye safe window. Although the pump lasers or intermediate orders in the laser system may not fall within the eye safe wavelength range, these wavelengths may be substantially blocked or filtered within the laser unit. Consequently, to achieve an eye safe laser even operating at a wavelength such as 1720 nm, the residual intermediate and pump wavelengths should be substantially filtered before the fiber or free space output.

Mid-Infrared Fiber Lasers

Figure 7:
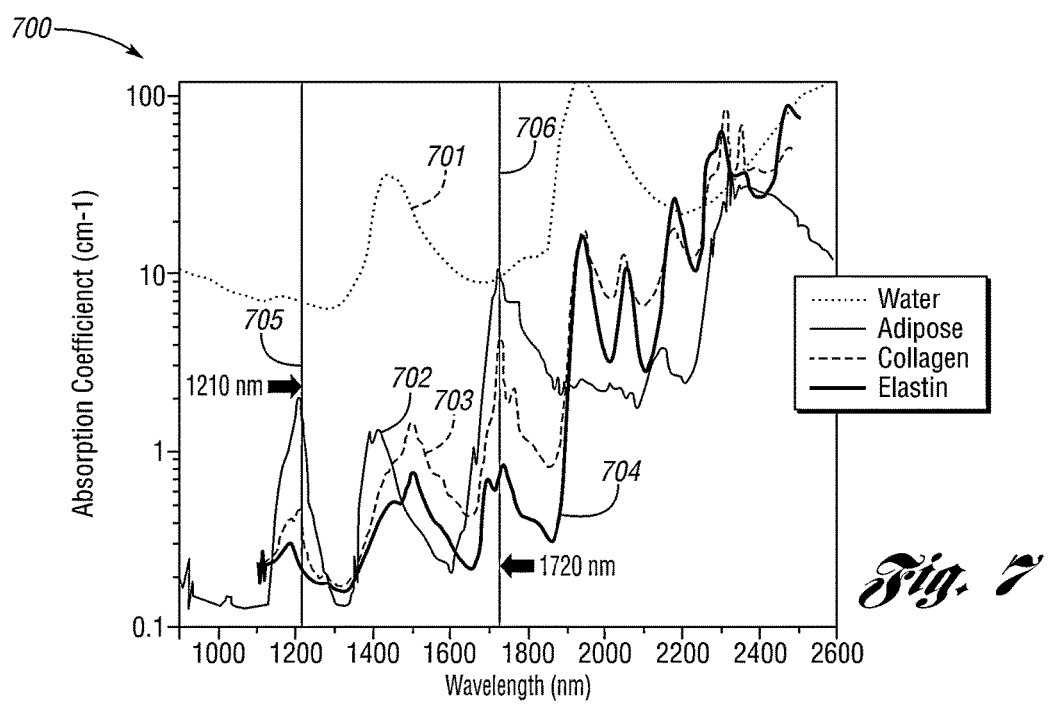
FIG. 7 illustrates the overlap of the absorption coefficients for water and tissue scattering, adipose, collagen and elastin; vertical lines are also drawn to highlight the wavelengths near 1210 nm and 1720 nm; the adipose and water absorption coefficients as well as the scattering loss are shown on a calibrated scale, while the collagen and elastin are in arbitrary units.

As an example, FIGS. 6 and 7 illustrate that there could be novel selective damage to tissue constituents or spectroscopy to detect particular tissue constituents, which could lead to novel medical diagnostics or therapeutics. In one embodiment, relatively narrow band lasers can be constructed near 1210 nm or 1720 nm by using cascaded Raman oscillators. These lasers could be beneficial for therapeutic medical procedures and can generate relatively high spectral density at wavelengths of interest. In another embodiment, super-continuum (SC) light sources or lasers can be implemented that can be broadband in the mid-infrared wavelength range and that could be beneficial for diagnostic medical procedures. The broadband light can be helpful for procedures based on spectroscopy, which, for example, can rely on the wavelength characteristics of different constituents to identify the constituents' presence through an algorithm such as spectral fingerprinting. Below some examples of cascaded Raman oscillators and super-continuum light sources are provided, along with examples of fiber lasers based on single-mode or double-clad fibers. These are exemplary mid-infrared fiber lasers, but other mid-infrared lasers, such as solid state lasers or semiconductor lasers, can also be used consistent with this disclosure.

In one embodiment, a mid-infrared laser can be constructed by using a pump fiber laser to generate a pump signal, and then to wavelength shift the pump signal to a longer wavelength using a cascaded Raman oscillator. In a preferred embodiment, the cascaded Raman oscillator can be a fiber surrounded by a plurality of gratings. As an example, the fiber laser can be a ring laser cavity or a linear laser cavity. For example, a ring laser cavity can be made with couplers surrounding a gain fiber. In another example, a linear laser cavity can comprise one or more optical gratings surrounding a gain fiber. In a preferred embodiment, the gain fiber can be a doped fiber, such as a ytterbium-doped fiber, an erbium-doped fiber, an erbium/ytterbium doped fiber, or a thulium doped fiber. Also, higher powers can be generated by using a gain fiber that is a cladding pumped fiber or a double clad fiber. Alternatively, the gain fiber could potentially be a photonic crystal fiber. Although particular examples are provided for doping and fiber types, different combinations or alternatives can be used consistent with this disclosure.

Figure 8:
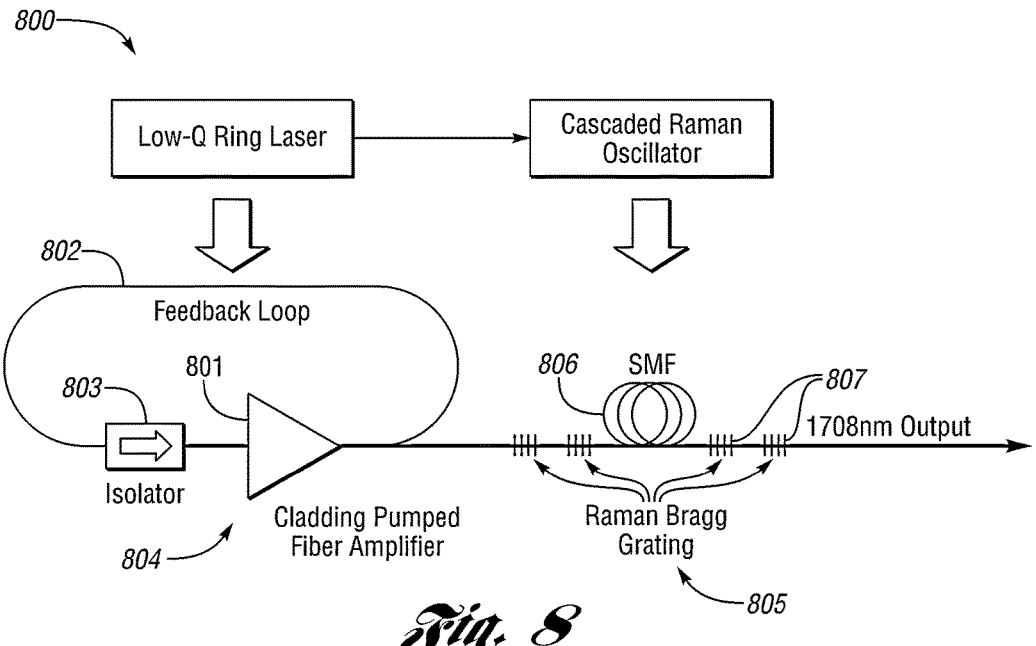
FIG. 8 illustrates a block diagram of one embodiment of a mid-infrared fiber laser operating near 1720 nm.

FIG. 8 illustrates a block diagram of one embodiment of a mid-infrared fiber laser 800 operating near 1720 nm. One advantage of such a configuration can be that all of the fiber parts can be spliced together to result in an all-fiber, monolithically integrated, no moving parts light source. In this particular example, the pump fiber laser 804 can be a cladding pumped fiber amplifier 801 with a feedback loop 802 around the amplifier to cause lasing. In one non-limiting example, an isolator 803 can be placed in the ring cavity of the pump laser to cause the lasing to be unidirectional. In this case, the cladding pumped fiber amplifier 801 can be an erbium/ytterbium doped amplifier operating near 1550 nm. The pump laser light can then be coupled to a cascaded Raman oscillator 805, where the fiber 806 can be a single-mode fiber and two sets of Bragg gratings 807 can be used to wavelength shift out to near 1720 nm.

Figure 9:
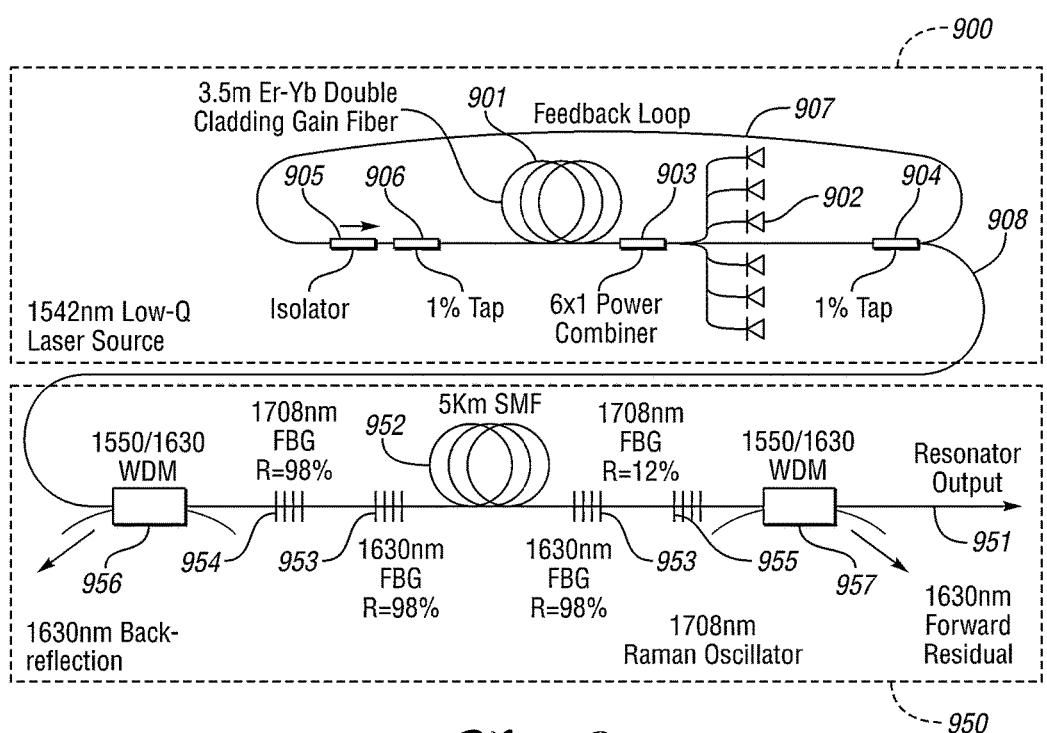
FIG. 9 shows details of one specific example of a mid-infrared fiber laser operating at approximately 1708 nm; the top part of the figure illustrates one embodiment of the pump fiber laser, and the bottom part of the figure illustrates one embodiment of the cascaded Raman oscillator or cascaded Raman wavelength shifter.

In one embodiment, a specific example of the mid-infrared fiber laser operating at approximately 1708 nm is shown in detail in FIG. 9. The top part of the figure illustrates one embodiment of the pump fiber laser 900 details, while the bottom part of the figure illustrates one embodiment of the cascaded Raman oscillator 950 details. In the pump fiber laser, the gain fiber 901 can exemplary be an erbium-ytterbium doped, double clad fiber. In one embodiment, the length of the gain fiber can be between 3 and 6 meters. One or more pump laser diodes 902 can be used to excite the gain fiber 901. In one embodiment, the pump lasers 902 can operate at wavelengths between approximately 935 nm and 980 nm, and between 2 and 18 pump laser diodes may be used. The one or more pump laser diodes 902 can be combined using a power combiner 903, and then the combined pump laser diode power can be coupled to the gain fiber 901. In this particular example, the pump laser diodes 902 can be coupled into the gain fiber 901 in a counter-propagating direction to the signal in the oscillator. However, the pump laser diodes could also co-propagate with the direction of the signal in the oscillator. After the pump combiner 903, a part of the output of the gain fiber can be separated at a power tap 904 and then feed back to the input using a feedback loop fiber 907. In the loop, an isolator 905 can also be inserted to permit unidirectional operation and lasing (in this particular example, the pump fiber laser 900 resonates in a counter-clockwise direction). Other elements may also be inserted into the ring cavity, such as additional taps 906. Although one particular example of a pump fiber laser 900 is described, any number of changes in elements or their positions can be made consistent with this disclosure. For example, the pump laser can be a high powered semiconductor laser, a solid state laser, a nonlinear crystal laser, or any combination of these.

The bottom of FIG. 9 illustrates one embodiment of a cascaded Raman oscillator 950 for shifting the pump fiber laser output wavelength to a longer signal wavelength 951. The center of the oscillator is a Raman gain fiber 952, which in this particular embodiment can be a standard single mode fiber SMF. The length of the SMF can be in the range of 300 m to 10 km, and as an example in this embodiment may be closer to approximately 5 km. Any number of fiber types, including high nonlinearity fibers, mid-infrared fibers, high numerical aperture fibers, or photonic crystal fibers, can be used consistent with this disclosure. The Raman gain fiber 952 can be surrounded by a plurality of fiber Bragg gratings FBG, 953, 954 and 955. In this particular embodiment, two cascaded Raman orders are used to transfer the pump output wavelength 908 near 1550 nm to the longer signal wavelength near 1708 nm. Hence, in FIG. 9 there can be two sets of fiber Bragg gratings.

As an example, the inner grating set 953 can be designed to provide high reflectivity near 1630 nm. The reflectivity can be in the range of 70 to 90 percent, and in this particular embodiment can be closer to 98%. The outer grating set 954 and 955 can be designed to reflect light near 1708 nm (i.e., the desired longer signal wavelength). The first fiber Bragg grating 954 can have high reflectivity, for example in the range of 70 to 90 percent, more preferably closer to 98%. The second fiber Bragg grating 955 also serves as the output coupler, and hence should have a lower reflectivity value. As an example, the reflectivity of grating 955 can be in the range of 8 to 50 percent, more preferably closer to 12%.

Moreover, to remove the residual shifted pump light from the first or intermediate orders of Raman shifting, WDM couplers can be used surrounding the oscillator, such as 956 and 957. In this particular embodiment, the WDM couplers 956 and 957 are 1550/1630 couplers (i.e., couplers that pass light near 1550 nm but that couple across or out wavelengths near 1630 nm). Such couplers can help to avoid feedback into the pump fiber laser 900 as well as minimize the residual intermediate orders in the longer signal wavelength 951. It may also be beneficial to add an isolator between the pump fiber laser 900 and the cascaded Raman oscillator 950 to minimize the effects of feedback. Although one specific example is provided for the cascaded Raman oscillator 950, any number of changes in the components or values or additional components can be made and are intended to be covered in this disclosure.

Figure 10A:
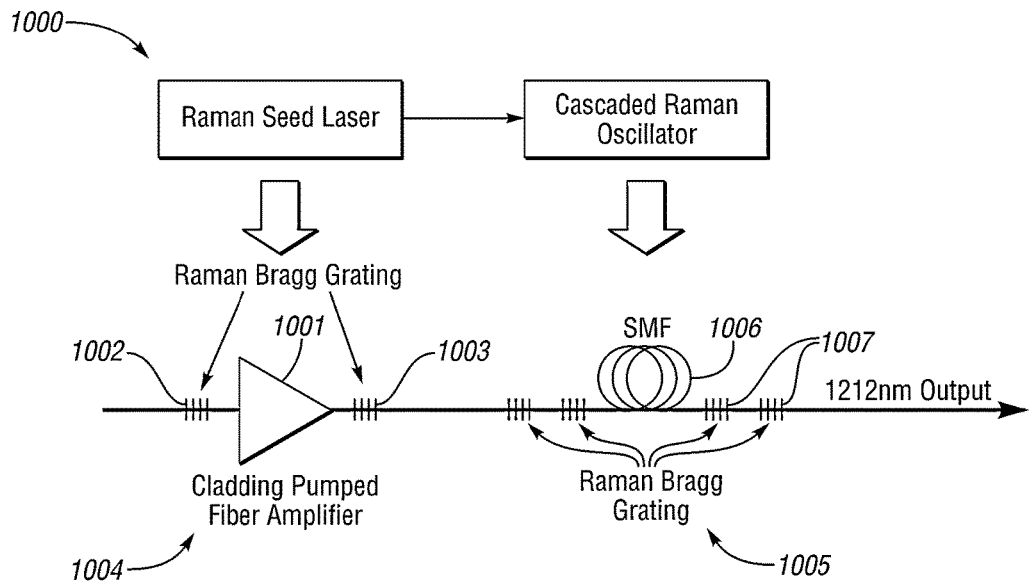
FIG. 10A illustrates a block diagram yet another embodiment of a mid-infrared fiber laser operating near 1210 nm.

FIG. 10A illustrates a block diagram of yet another embodiment of a mid-infrared fiber laser 1000 that operates near 1212 nm. Whereas FIGS. 8 and 9 use a ring cavity pump fiber laser, FIG. 10 uses a linear cavity pump fiber laser. Either of these configurations or other versions of the pump fiber laser can be used consistent with this disclosure. In this particular example, the pump fiber laser 1004 can be a cladding pumped fiber amplifier 1001 surrounded by fiber Bragg gratings 1002 and 1003 around the amplifier to cause lasing. In this case, the cladding pumped fiber amplifier 1001 can be a ytterbium doped amplifier operating approximately in the wavelength range between 1050 and 1120 nm. The pump laser light can then be coupled to a cascaded Raman oscillator 1005, where the fiber 1006 can be a single-mode fiber and two sets of Bragg gratings 1007 are used to wavelength shift out to near 1212 nm.

Figure 10B:
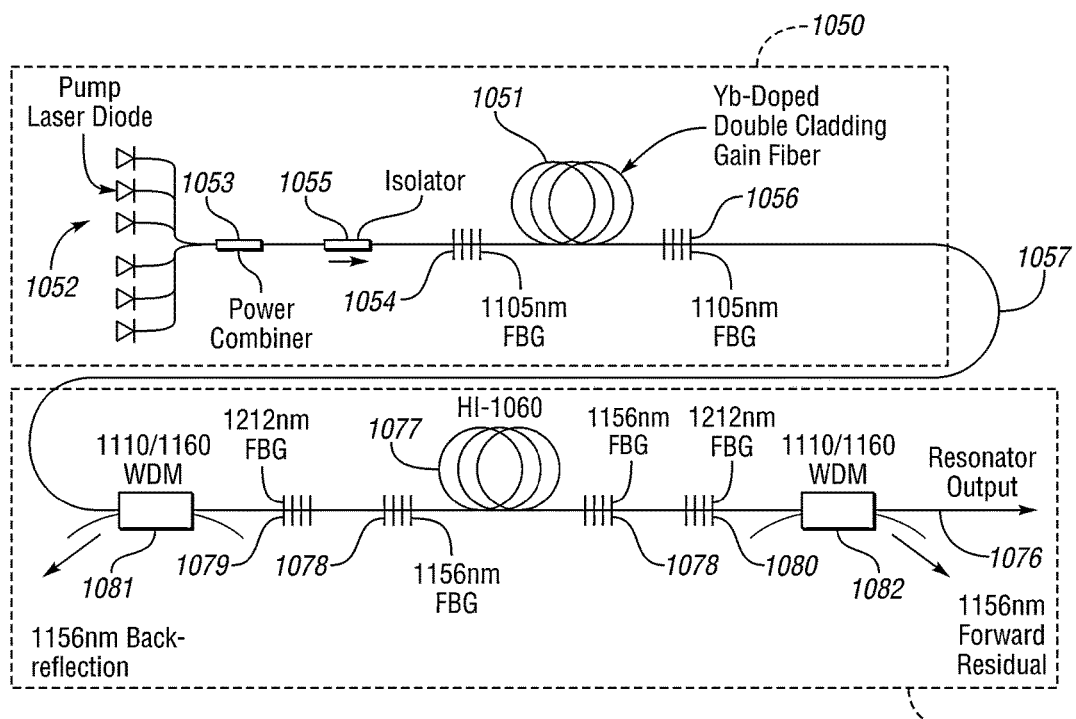
FIG. 10B shows details of one specific example of a mid-infrared fiber laser operating at approximately 1212 nm; the top part of the figure illustrates one embodiment of the pump fiber laser, and the bottom part of the figure illustrates one embodiment of the cascaded Raman oscillator or cascaded Raman wavelength shifter.

In yet another embodiment, a specific example of the mid-infrared fiber laser operating at approximately 1212 nm is shown in detail in FIG. 10B. The top part of the figure illustrates one embodiment of the pump fiber laser 1050 details, while the bottom part of the figure illustrates one embodiment of the cascaded Raman oscillator 1075 details. In the pump fiber laser, the gain fiber 1051 can exemplary be a ytterbium doped, double clad fiber. In one embodiment, the length of the gain fiber can be between 3 and 10 meters. One or more pump laser diodes 1052 can be used to excite the gain fiber 1051. In one embodiment, the pump lasers 1052 can operate at wavelengths between approximately 850 nm and 980 nm, and between 2 and 18 pump laser diodes may be used. The one or more pump laser diodes 1052 can be combined using a power combiner 1053, and then the combined pump laser diode power can be coupled to the gain fiber 1051. After the pump combiner 1053, it may be beneficial to use one or more isolators 1055 to avoid feedback into the pump laser diodes 1052.

The pump fiber laser can be formed by using a set of gratings 1054 and 1056 around the gain fiber 1051. In one embodiment, the fiber Bragg gratings 1054 and 1056 can have reflecting at a wavelength near 1105 nm. The reflectivity of 1054 can be in the range of 70 to 90 percent, and in this particular embodiment can be closer to 98%. The second fiber Bragg grating 1056 can also serve as the output coupler, and hence may have a lower reflectivity value. As an example, the reflectivity of grating 1056 can be in the range of 5 to 50 percent, more preferably closer to 10%. Other elements may also be inserted into the linear resonator cavity, such as additional taps. Although one particular example of a pump fiber laser 1050 is described, any number of changes in elements or their positions can be made consistent with this disclosure.

The bottom of FIG. 10B illustrates one embodiment of a cascaded Raman oscillator 1075 for shifting the pump fiber laser output wavelength to a longer signal wavelength 1076. The center of the oscillator is a Raman gain fiber 1077, which in this particular embodiment can be a HI-1060 fiber, which operates at a single spatial mode at the wavelengths of the ytterbium amplifier. The length of the Raman gain fiber 1077 can be in the range of 300 m to 10 km, and as an example in this embodiment may be closer to approximately 1 km. Any number of fiber types, including high nonlinearity fibers, mid-infrared fibers, high numerical aperture fibers, or photonic crystal fibers, can be used consistent with this disclosure. The Raman gain fiber 1077 can be surrounded by a plurality of fiber Bragg gratings FBG, 1078, 1079 and 1080. In this particular embodiment, two cascaded Raman orders are used to transfer the pump output wavelength 1057 near 1105 nm to the longer signal wavelength near 1212 nm. Hence, in FIG. 10B there can be two sets of fiber Bragg gratings.

As an example, the inner grating set 1078 can be designed to provide high reflectivity near 1156 nm. The reflectivity can be in the range of 70 to 90 percent, and in this particular embodiment can be closer to 99%. The outer grating set 1079 and 1080 can be designed to reflect light near 1212 nm (i.e., the desired longer signal wavelength). The first fiber Bragg grating 1079 can have high reflectivity, for example in the range of 70 to 90 percent, more preferably closer to 99%. The second fiber Bragg grating 1080 can also serve as the output coupler, and hence may have a lower reflectivity value. As an example, the reflectivity of grating 1080 can be in the range of 8 to 50 percent, more preferably closer to 25%.

Moreover, to remove the residual shifted pump light from the first or intermediate orders of Raman shifting, WDM couplers can be used surrounding the oscillator, such as 1081 and 1082. In this particular embodiment, the WDM couplers 1081 and 1082 are 1100/1160 couplers (i.e., couplers that pass light near 1100 nm but that couple across or out wavelengths near 1160 nm). Such couplers can help to avoid feedback into the pump fiber laser 1050 as well as minimize the residual intermediate orders in the longer signal wavelength 1076. It may also be beneficial to add an isolator between the pump fiber laser 1050 and the cascaded Raman oscillator 1075 to minimize the effects of feedback. Although one specific example is provided for the cascaded Raman oscillator 1075, any number of changes in the components or values or additional components can be made and are intended to be covered in this disclosure.

Super-Continuum Light Sources or Lasers

The cascaded Raman oscillators, such as in FIGS. 8-10, can be particularly useful when significant power is desired in a relatively narrow bandwidth, such as for use in a therapeutic procedure. On the other hand, it can be valuable to have a broadband source or a tunable source to observe either through absorption or reflection the spectral features associated with a particular type of tissue, such as might be done in a diagnostic procedure. A super-continuum (SC) light source or laser can be used for generating broadband light. In an SC laser, a MOPA (master oscillator optical amplifier) type configuration can be used for pumping, which can comprise a seed laser followed by optical amplifiers to boost the power. Then, the broadband light can be generated in an optical fiber using the nonlinear mechanisms in the fiber. For wavelengths shorter than about 2.6 microns, fused silica fibers can be used for SC generation, such as standard single-mode fiber, high-nonlinearity fiber, high-NA fiber, dispersion shifted or dispersion compensating fiber. For wavelengths extending beyond 2.6 microns, the SC generation can be achieved in a mid-infrared fiber, such as fluorides, chalcogenides, ZBLAN, tellurite or germanium oxides.

Figure 11A:
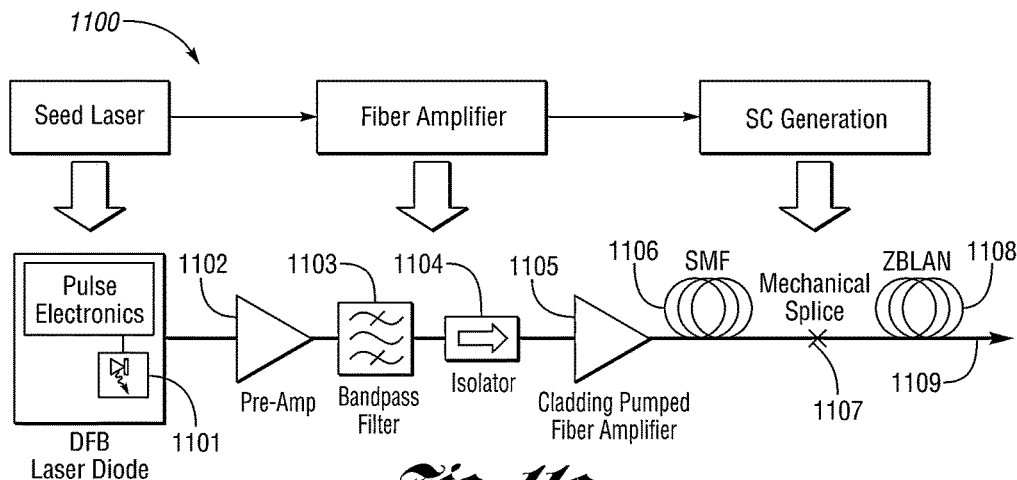
FIG. 11A illustrates a block diagram of one embodiment of a mid-infrared super-continuum fiber laser.

FIG. 11A illustrates a block diagram of one embodiment of a mid-infrared SC fiber laser 1100. In this example, the pump laser comprises a seed laser diode 1101 followed by several stages of amplification in fiber amplifiers 1102 and 1105. Then, the SC can be generated in this embodiment in a standard single-mode fiber 1106 followed by a mid-infrared ZBLAN fiber 1108. The output 1109 from this source can range in power up to about 10 W or 40 W time averaged power, and the spectral width at the output can range between approximately 800 nm and 4500 nm. As another example, if the super-continuum fiber 1108 is instead a fused silica fiber, then the range of the super-continuum can range from approximately 1600 to 1800 nm in one embodiment. The seed laser diode 1101 can be a telecom-grade, distributed feedback laser diode operating in the telecom band, which can span for instance 1500 to 1600 nm. The pre-amplifier 1102 can be made in a single-mode erbium-doped fiber amplifier. The power amplifier 1105 can generate relatively high powers by using a doped cladding-pumped or double clad amplifier fiber, doped for example with erbium/ytterbium. Although two stages of amplification are shown in FIG. 11A, any number of stages can be used, including adding one or more stages of intermediate amplifiers. Also, it can be advantageous to place band-pass filters 1103 and isolators 1104 between amplifier stages to control the background noise level and to avoid feedback into the amplifiers.

Figure 11B:
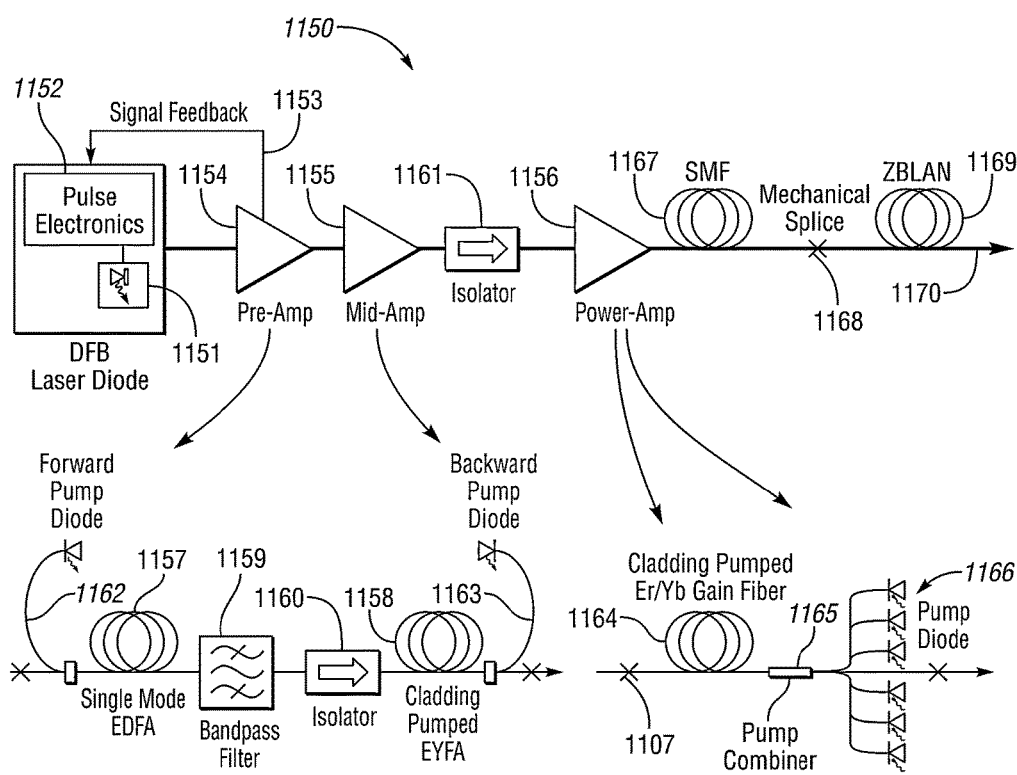
FIG. 11B shows a particular example of a mid-infrared super-continuum laser that can generate relatively high powers.

A particular example of a mid-infrared SC laser 1150 that can generate relatively high powers is illustrated in FIG. 11B. In one embodiment, a 10 mW distributed feedback (DFB) laser diode 1151 emitting at 1542 nm can be driven by electronic circuits 1152 to provide 400 ps to 2 ns pulses at variable repetition rates. The electronic circuits 1152 can also drive the laser diode to output a pre-programmed pulse pattern instead of fixed repetitive pulses. Also, in this example the optical pulses can be amplified by three stages of fiber amplifiers—an erbium-doped fiber amplifier (EDFA) pre-amplifier 1154 followed by erbium/ytterbium doped fiber amplifier (EYFA) mid-stage 1155 and power amplifiers 1156. In one embodiment, the pre-amplifier can use a length of single mode erbium doped gain fiber 1157, where the length may be between 0.5 m and 5 m, preferably close to 1 m in length. In this embodiment, the mid-stage amplifier 1155 can employ a length of larger core cladding-pumped gain fiber 1158, where the length can be between 0.5 and 5 m, preferably close to 1.5 m in length. The EDFA 1157 can be co-propagation or forward pumped using a pump laser diode 1162, preferably operating around 980 nm. The cladding pumped EYFA 1158 can also be counter-propagation or backward pumped with a laser diode 1163, preferably operating between 935 nm and 980 nm.

In a multi-stage amplifier such as 1155, the noise performance, i.e. amplified spontaneous emission (ASE), can be determined by the upstream stages before the power amplifier. To lower the ASE, it can be advantageous to separate the amplifier into a pre-amplifier 1157 and a mid-stage amplifier 1158. Therefore, the ASE after the first stage can be filtered by a bandpass filter 1159, such as a 100 GHz filter, and the signal gain in each amplifier stage can be reduced. Optical isolators 1160 and 1161 are also advantageously placed between the stages to protect the system from back-reflection damage as well as reduce the noise figure and improve the efficiency of the combined amplifier system. In one preferred embodiment, a ~20 dB gain can be obtained in both the pre- and mid-amplifier for the optical signal while the ASE-to-signal ratio can be measured to be less than 1%. The nonlinear broadening of the optical pulses before the power amplifier can also be negligible. In addition, an optical tap may be used to sample the output power of the pre-amplifier and to enable the signal feedback control 1153.

In one particular embodiment, the power from the mid-amplifier 1155 is boosted in an all-fiber-spliced, cladding-pumped, EYFA 1156 or 1164 before coupling into the SC fiber 1167 and 1169. A cladding-pumped fiber amplifier 1164 can be advantageously used to increase the gain volume and enable the coupling of multiple pump diodes 1166. In addition, to minimize the nonlinear effects in the amplifier, a short length of gain fiber with a large core diameter and a high doping concentration can be used.

In one embodiment of a 10 W SC generation experiment, the gain fiber 1164 is designed with a core diameter of between 8 to 25 microns, preferably around 15 µm, and an effective NA in the range of 0.1 to 0.2, preferably closer to 0.15; thus, the mode field size can be close to that of the SMF fiber. The EYFA 1164 can be several meters in length, as an example ~5 m in length. In one embodiment, ten 8 W 976 nm and two 8 W 940 nm uncooled multimode pump diodes 1166 can be coupled into the gain fiber through an 18×1 pump combiner 1165. Single spatial mode operation can be maintained in the EYFA by carefully splicing the gain fiber to the signal-input SMF fiber and the pump combiner. In this example, the output spectrum after the SMF fiber can be broadened and red-shifted to ~2.2 µm primarily due to the break-up of the nanosecond pulses through modulation instability (MI) followed by soliton self-frequency shifting. In another embodiment, a 12/130 µm core/cladding diameter erbium/ytterbium co-doped fiber with a 0.20 NA can be used as the gain fiber 1164 in the final stage power amplifier 1156.

As a particular example, the SC output 1170 can be generated in a two-stage process. In the first stage SMF fiber 1167, modulation instability (MI) can be utilized to break up the nanosecond pulses into femtosecond pulse trains to enhance the nonlinear optical effects and red-shift the optical spectrum to beyond 2 µm. The SC spectrum can then be broadened in the following ZBLAN fiber 1169 through the interplay of self-phase modulation, Raman scattering and parametric four-wave mixing.

In one embodiment, the SC can be generated by butt coupling 1168 the light from the 2 m length of SMF fiber 1167 after the EYFA into a piece of ZBLAN fluoride fiber 1169. Two ZBLAN fluoride fibers have been used exemplary in the experiments. In the 10.5 W high power SC experiment, the ZBLAN fiber 1169 can be 7 m long and can have a core diameter of 8.9 µm, a cladding diameter of 125 µm and an NA of 0.21. In another example, the ZBLAN fiber 1169 can have a length of ~15 m with a core diameter of 10.6 µm, a cladding diameter of 125 µm and an NA of 0.2. Advantageously, all ends of SMF 1167 and ZBLAN 1169 fibers can be angle-cleaved to avoid light back reflected into the pump system. Although one particular example of mid-infrared SC generation has been shown in FIG. 11, any number of elements can be added or positions changed or parameter values changed consistent with this disclosure.

Figure 12A:
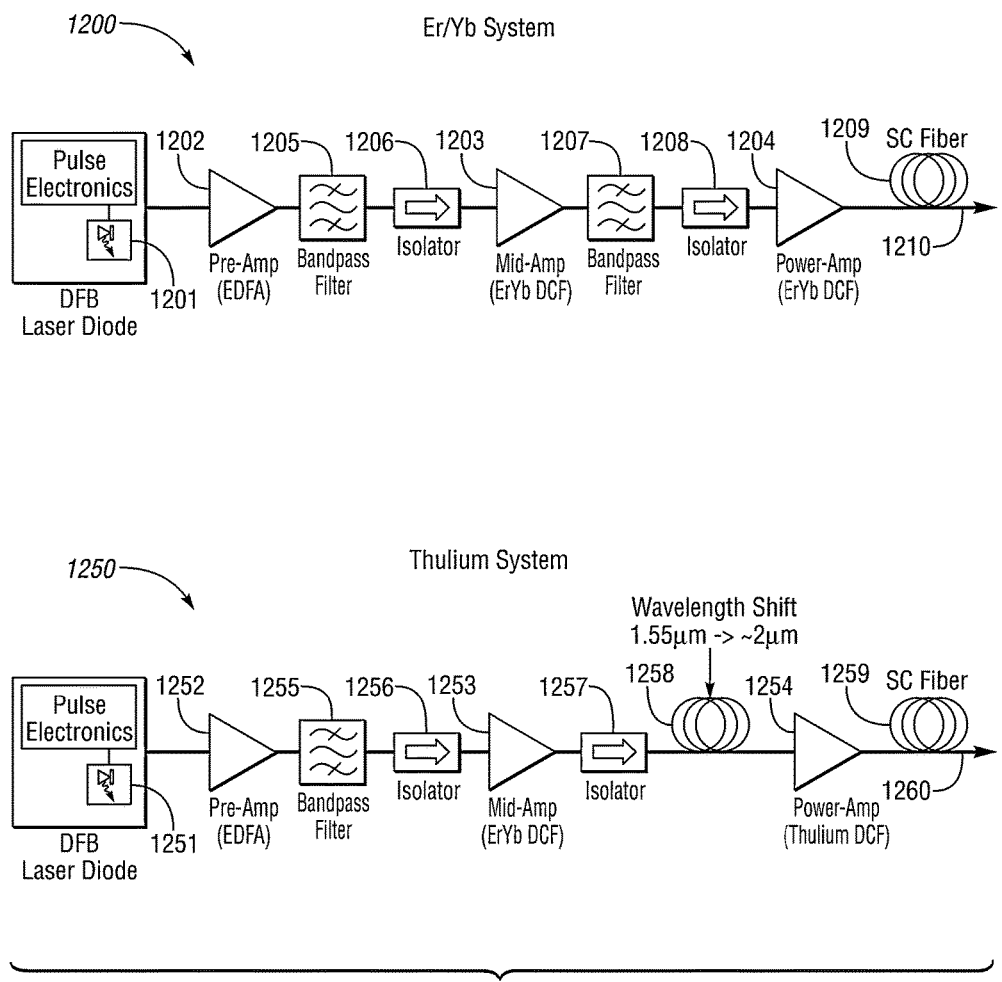
FIG. 12A illustrates details of different exemplary super-continuum lasers; the top of the figure provides details of an SC source that can provide light from approximately 1400 nm to 1800 nm or broader, while the bottom of the figure provides details of an SC source that can provide light from about 1900 nm to 2500 nm or broader.

The configuration of FIG. 11 can lead to broadband light covering several octaves, exemplary from about 800 nm to approximately 4500 nm. However, narrower bandwidth SC may in some cases be desired at wavelengths shorter than about 2.5 microns. Several examples of SC sources are illustrated in FIG. 12A. The top SC source of FIG. 12A can lead to bandwidths ranging from about 1400 nm to 1800 nm or broader, while the lower SC source of FIG. 12A can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber SMF, high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

In one embodiment, the top of FIG. 12A illustrates a block diagram for an SC source 1200 capable of generating light exemplary between approximately 1400 and 1800 nm or broader. As an example, a pump fiber laser similar to FIG. 11 can be used as the input to a SC fiber 1209. The seed laser diode 1201 can comprise a DFB laser that generates, exemplary, several milli-watts of power around 1553 nm. The fiber pre-amplifier 1202 can comprise an erbium-doped fiber amplifier. In this example a mid-stage amplifier 1203 can be used, which can comprise an erbium/ytterbium doped double-clad fiber. A bandpass filter 1205 and isolator 1206 may be used between the pre-amplifier 1202 and mid-stage amplifier 1203. The power amplifier stage 1204 can comprise a larger core size erbium/ytterbium doped double-clad fiber, and another bandpass filter 1207 and isolator 1208 can be used before the power amplifier 1204. The output of the power amplifier can be coupled to the SC fiber 1209 to generate the SC output 1210. This is just one exemplary configuration for an SC source, and other configurations or elements can be used consistent with this disclosure.

In yet another embodiment, the bottom of FIG. 12A illustrates a block diagram for an SC source 1250 capable of generating light exemplary between approximately 1900 and 2500 nm or broader. As an example, the seed laser diode 1251 can comprise a DFB or DBR laser that generates, exemplary, several milli-watts of power around 1553 nm. The fiber pre-amplifier 1252 can comprise an erbium-doped fiber amplifier. In this example a mid-stage amplifier 1253 can be used, which can comprise an erbium/ytterbium doped double-clad fiber. A bandpass filter 1255 and isolator 1256 may be used between the pre-amplifier 1252 and mid-stage amplifier 1253. The power amplifier stage 1254 can comprise a thulium doped double-clad fiber, and another isolator 1257 can be used before the power amplifier 1254. Note that the output of the mid-stage amplifier 1253 can be approximately near 1553 nm, while the thulium-doped fiber amplifier 1254 can amplify wavelengths longer than approximately 1900 nm and out to about 2100 nm. Therefore, for this configuration wavelength shifting may be required between 1253 and 1254. In one embodiment, the wavelength shifting can be accomplished using a length of standard single-mode fiber 1258, which can exemplary have a length between approximately 5 and 50 meters. The output of the power amplifier 1254 can be coupled to the SC fiber 1259 to generate the SC output 1260. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 11 and 12 are that they may use all-fiber components, so that the SC laser can be all-fiber, monolithically integrated with no moving parts. The all-integrated configuration can consequently be robust and reliable.

Figure 12B:
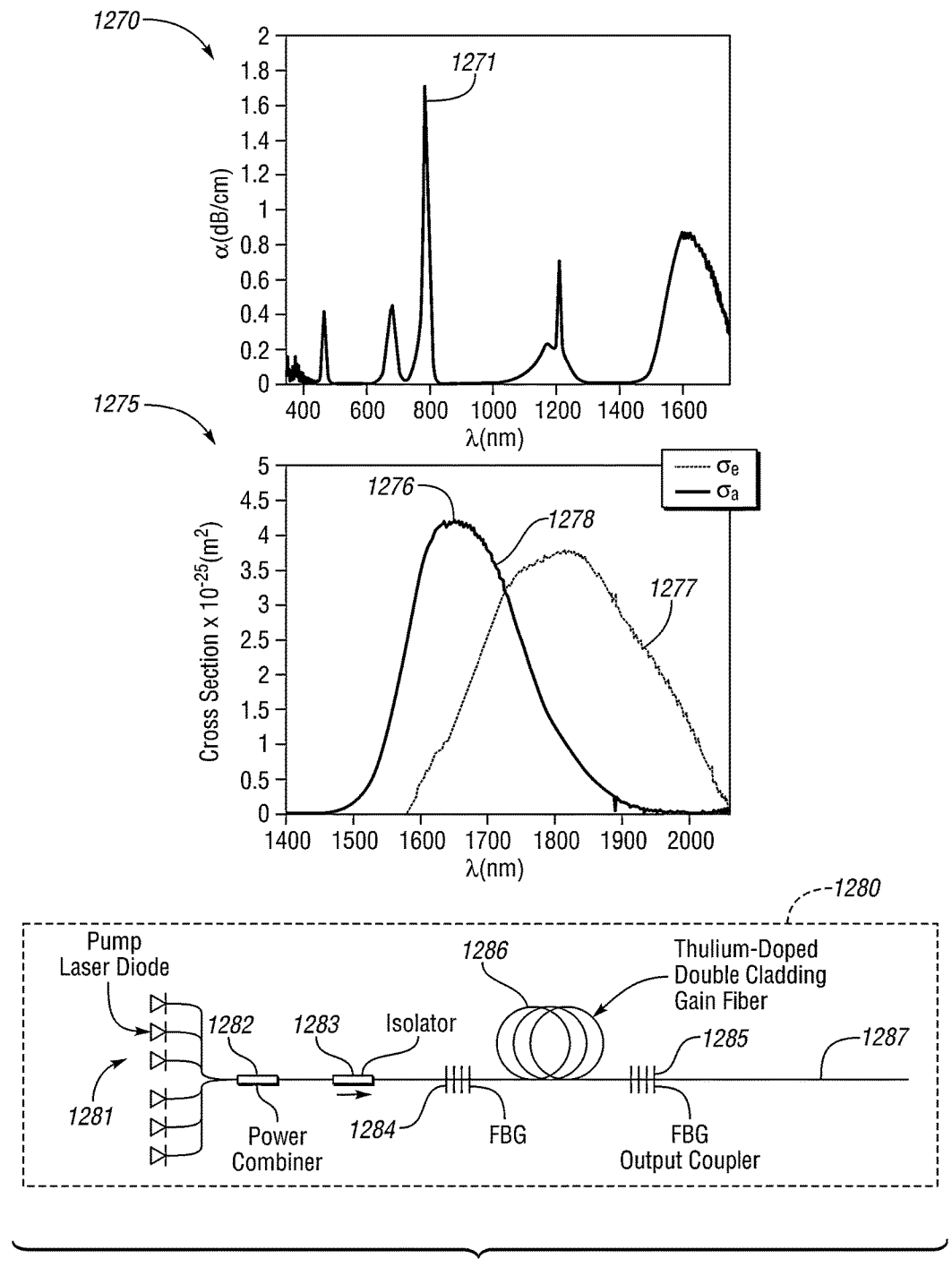
FIG. 12B illustrates one embodiment of a thulium-doped fiber laser operating near a center wavelength around 1720 to 1750 nm or longer; the top left curve shows exemplary absorption bands for thulium in fused silica fiber, and the top right curve shows exemplary absorption and emission bands for thulium in the wavelength range between approximately 1400 and 2100 nm; the bottom configuration illustrates one embodiment of the thulium-doped fiber laser operating in the mid-infrared wavelength range.

As yet another example of a mid-infrared light source that can generate light around 1720 nm to 1800 nm, FIG. 12B illustrates a thulium doped cladding-pumped fiber laser, along with the absorption and emission bands for thulium-doped fibers. The top left side of FIG. 12B shows and exemplary absorption spectrum 1270 for thulium doping in a single-mode silica fiber. As an example, one efficient band 1271 to pump the fiber can be around 790 nm, where high-power semiconductor pump lasers are available. The top right side 1275 of FIG. 12B illustrates the absorption cross-section 1276 and emission cross-section 1277 for a typical thulium doped fiber in the wavelength range between 1400 nm and 2000 nm. As 1275 shows, the cross-over wavelength where the absorption and emission intersect 1278 can be approximately 1720 nm, and this can mean that a thulium-doped fiber laser could potentially be made between approximately 1720 nm and 2100 nm.

In a preferred embodiment, a thulium-doped fiber laser 1280 can be implemented as illustrated in the bottom of FIG. 12B for mid-infrared selective damage. One or more pump laser diodes 1281 can be used, where the pump laser diode wavelengths can be near the absorption band 1271 around 790 nm. The pump lasers can be combined using a pump combiner 1282, and then the combined light can be coupled to the gain fiber 1286. Optionally, one or more isolators or spectral filters 1283 can be used to minimize feedback into the pump laser diodes 1281. The gain fiber 1286 can be a thulium-doped fiber amplifier, and in one preferred embodiment the gain fiber 1286 can be a double-clad fiber or a cladding-pumped fiber. The resonator 1280 can be formed by placing reflectors surrounding the gain fiber 1286, where the reflector on the left (e.g., 1284) can transmit the pump wavelengths but reflect the lasing output wavelength 1287. The reflector on the right (e.g., 1285) can also serve as the output coupler and should be at least partially transmitting and partially reflecting at the lasing output wavelength 1287. In the particular embodiment to FIG. 12B, a fiber Bragg grating 1284 can be used on the left side, and another fiber Bragg grating 1285 that also serves as the output coupler can be used on the right side of the cavity surrounding the gain fiber 1286. Although one embodiment of a thulium-doped fiber laser 1280 is illustrated in FIG. 12B, the various elements in the configuration can be placed at alternative locations, and other elements may also be added or removed from this configuration consistent with this disclosure.

In one particular example, it may be advantageous to have the thulium-doped fiber laser 1280 operate at wavelengths near 1720 nm or out to 1750 nm, such as when the absorption in adipose, collagen and/or elastin have a local maximum. Since these wavelengths are close to the cross-over 1278 between absorption and emission in thulium, several additional procedures or elements may be considered for the laser 1280 so as to push the wavelengths to shorter than approximately 1750 nm. In one embodiment, a shorter gain fiber may be used, and the pump power can be maintained fairly high through the gain fiber to nearly fully invert the gain fiber. For example, a nearly fully inverted gain fiber will have more emission than absorption. In another embodiment, the fiber Bragg grating 1284 and 1285 reflecting wavelengths can be selected at the shorter wavelengths desired. Moreover, the output coupling ratio for the output coupler 1285 may be selected to optimize lasing at the shorter wavelengths. In yet another embodiment, a lossy element may be introduced into the laser cavity 1280, wherein the lossy element has a higher loss at the longer wavelengths such as 1750-2100 nm and lower loss at the shorter wavelengths such as 1700-1750 nm. In a further embodiment, bends may be introduced on sections of the fiber in the laser cavity 1280 to introduce bend-induced loss, since it is known that bend-induced loss usually increases with increasing wavelength. In an alternative embodiment, a seed laser signal may be introduced toward the shorter wavelengths around 1720-1750 nm, thereby effectively decreasing the loss at these wavelengths. Any one of these or combinations of these techniques may be used to cause the thulium-doped fiber oscillator 1280 to operate in the wavelengths closer to 1720 to 1750 nm.

Figure 13:
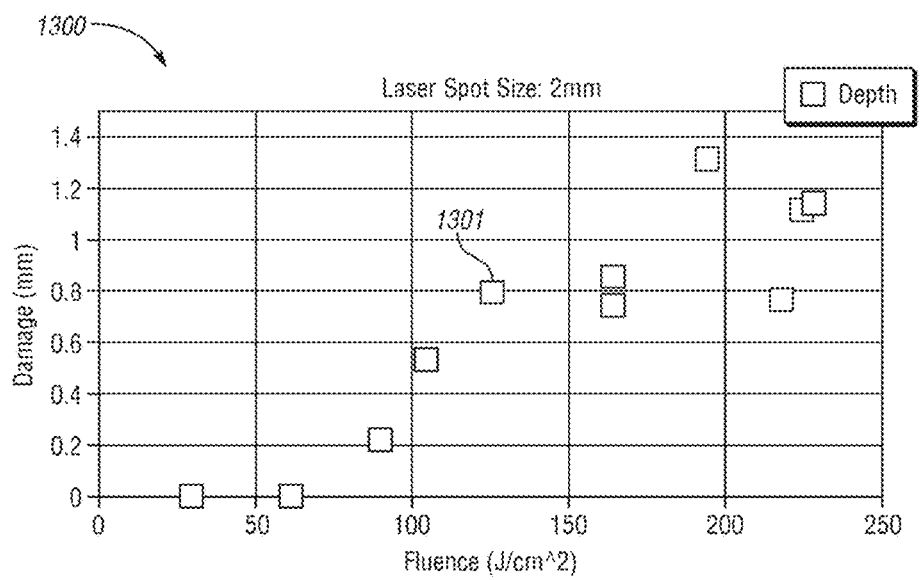
FIG. 13 illustrates experimental results for the depth of damage obtained in an in-vitro human skin sample plotted as a function of laser fluence at about 1708 nm incident on the skin sample.

Based on the scattering through tissue and water absorption shown for example in FIGS. 4 and 5, one advantage of using wavelengths near 1210 nm or 1720 nm can be the deeper penetration depths that can be achieved. To explore this advantage, the fiber laser configuration of FIG. 9 was exemplary used on in vitro human skin tissue samples. In one embodiment, FIG. 13 illustrates the depth of damage 1301 obtained in the in-vitro human skin samples plotted as a function of laser fluence at 1708 nm incident on the skin sample. The curve 1301 shows that the damage depth can increase with increased fluence at 1708 nm, and that the penetration depth can approach approximately 1.4 mm in the skin sample. Thus, some of the advantages of using mid-infrared wavelengths can be demonstrated using the various laser configurations of FIGS. 8 through 12.

Although cascaded Raman wavelength shifters, fiber lasers, and super-continuum lasers have been described as some exemplary lasers for generating mid-infrared light between approximately 1 and 10 microns, a myriad of other laser systems exist and are intended to be included within the scope of this disclosure. In one embodiment, different combinations of the laser such as described in FIGS. 8 through 12 can be used beneficially. For instance, the output from a cascaded Raman wavelength shifter operating near 1210 nm can be combined with the output from a cascaded Raman wavelength shifter operating near 1720 nm. One benefit of such a combination might be that different penetration depths into a biological tissue can be obtained using the different wavelengths. In another embodiment, it may be advantageous to combine one or more cascaded Raman wavelength shifters with one or more super-continuum lasers. For example, one advantage of such a configuration may be the ability for the laser system to perform both diagnostics and therapeutic procedures. In addition, different types of optical amplifiers and fibers can be used in the different configurations such as shown in FIGS. 8-12. Optical amplifier materials include fibers doped with different constituents, such as erbium, ytterbium, and thulium or co-doped materials such as erbium/ytterbium. Also, different kinds of fibers can be used in any of these configurations, and exemplary fibers can be made at least in part from fused silica, chalcogenides, fluorides, telluride, ZBLAN, photonic crystal fibers, etc.

Alternative laser systems can also be used for mid-infrared light generation. For example, other types of fiber lasers can be used, including modelocked lasers, MOPA or master oscillator followed by amplifiers, and fiber oscillators. In one embodiment, solid state lasers can be used that comprise materials including thulium, holmium, erbium, prysadinium, ytterbium, and chromium. In another embodiment, different types of semiconductor lasers can be used, including optically pumped semiconductor lasers, lead-salt diode lasers, antimonide diode lasers, lasers based on III-IV and II-VI semiconductor materials, as well as intra-band lasers, such as quantum cascade lasers. In yet another embodiment, gas lasers may be used, including carbon dioxide and carbon monoxide lasers. In a further embodiment, mid-infrared light sources can be based on nonlinear frequency conversion, such as optical parametric oscillators and amplifiers, difference frequency generation and parametric frequency conversion. As an example, such nonlinear frequency conversion techniques can use quasi-phase matched materials, including periodically-poled lithium niobate PPLN, gallium arsenide GaAs, lithium tantalite, and ferroelectric crystals of the potassium titanyl phosphate family. These mid-infrared lasers as well as any combinations of these can be used in the exemplary medical procedures described below.

Laser Beam Output Parameters

The laser beam output that may be used in the healthcare, medical or bio-technology applications can have a number of parameters, including wavelength, energy or fluence, spatial spot size, and pulse temporal shape and repetition rate. Some exemplary ranges for these parameters and some of the criteria for selecting the ranges are discussed below. These are only meant to be exemplary ranges and considerations, and the particular combination used may depend on the details and goals of the desired procedure.

Whereas it may be advantageous in a diagnostic procedure to use a broadband laser such as a super-continuum source, for various therapeutic procedures the wavelength for the laser may be selected on the basis of a number of considerations. In one embodiment, for selective damage it may be advantageous to reduce or minimize the absorption due to water and blood as well as scattering through tissue. As an example, from FIG. 5 advantageous windows can be from 1200 to 1350 nm or 1600 to 1800 nm.

In another embodiment, it may be advantageous to tune the wavelength to near an absorption peak in a particular type of tissue. For example, FIGS. 6 and 7 illustrate that wavelengths near 1210 nm or 1720 nm can coincide with local absorption maxima for adipose, collagen and elastin. Also, from FIGS. 6 and 7 it can be seen that the wavelength window near 1720 nm falls near a local minimum in water absorption and scattering loss. In one embodiment, having lower water absorption and scattering loss, such as near 1720 nm, can advantageously permit deeper penetration of the laser light into the tissue. For example, near 1720 nm the penetration depth into skin or typical tissue may be in the range between 0.5 mm to several millimeters, up to perhaps 3 to 4 millimeters. As one example, FIG. 13 illustrates that light near 1708 nm can penetrate approximately 1.4 mm in skin tissue.

In yet another embodiment, it may be advantageous to have the laser wavelength fall in the so-called eye-safe wavelength range. For instance, wavelengths longer than approximately 1400 nm can fall within the eye safe window. So, from an eye safety consideration there may be an advantage of using the wavelength window near 1720 nm rather than the window near 1210 nm. Thus, some of the considerations in selecting the laser wavelength range from selective tissue absorption, water absorption and scattering loss, penetration depth into tissue and eye safe operation. From a combination of these criteria, the wavelength near 1720 nm may be particularly advantageous for selectively damaging adipose, collagen and elastin. However, other criteria or considerations may also be used in selecting the particular wavelength, and in this disclosure the wavelengths near 1720 nm are merely selected as a non-limiting example. For instance, a combination of 1210 nm and 1720 nm may be used to obtain different penetration depths or to control the power density profile into the dermis or other tissue.

Another parameter for the laser can be the energy, fluence, or pulse power density. The fluence is the energy per unit area, so it can have the units of Joules/cm$^2$. As an example, in dermatological applications it can be advantageous to use fluences less than approximately 250 J/cm$^2$ to avoid burning or charring the epidermis layer. As illustrated in FIG. 13, diagnostic procedures may benefit from having fluences less than about 50 J/cm$^2$, while therapeutic procedures may benefit from having fluences in the range of approximately 30 to 250 J/cm$^2$, preferably in the range of 50 to 200 J/cm$^2$. In another embodiment, it may even be advantageous to use lower fluence levels for therapeutic procedures to impart less pain to patients, for example in the range of approximately 30 J/cm$^2$ or less. These types of fluence levels may typically correspond to time averaged powers from the laser exceeding approximately 10 W, preferably in the power range of 10 to 30 W, perhaps as high as 50 W or more. Although particular fluence and power ranges are provided by way of example, other powers and fluences can be used consistent with this disclosure.

Although the output from a fiber laser may be from a single or multi-mode fiber, different spatial spot sizes or spatial profiles may be beneficial for different applications. For example, for applications where adipose tissue may be damaged around an organ, it may be advantageous to either collimate or focus the laser light onto the adipose. In one embodiment, it may also be beneficial to have a line scan rather than individual laser spots exposing the adipose tissue. On the other hand, for applications such as dermatology or where light may be exposed onto an external part of the body, it may be desirable to have a collimated or expanded beam size. To expand and/or collimate the beam, one or more lenses or curved mirrors may be used after the delivery fiber. In one example, the beam waist or spot size can be 3 mm or more, preferably 1 cm or even larger. The larger spot sizes can permit faster procedure times. For example, a spot size with a diameter in the range of 3 mm to 1 cm can lead to scanning over a patients face within 15 minutes by a dermatologist. In yet another embodiment, although the output from a fiber is typically a Gaussianshaped profile, it may be advantageous to have a spatial beam shape that is more square-like. As an example, the square-like spatial mode can be achieved by using an aperture at the output of the fiber and blocking the wings of the Gaussian-like beam. One reason that the square-like beam shape may be desirable is that it can have a more uniform light intensity across the beam. Another advantage of the square-like beam may be that the area of the body that is to be treated can be set up or marked as a grid, and then the laser beam can be moved from one grid location to another. Although particular spatial mode shapes and sizes have been described, any number of other shapes and sizes may be used consistent with this disclosure.

Various types of damage mechanisms are possible in biological tissue. In one embodiment, the damage may be due to multi-photon absorption, in which case the damage can be proportional to the intensity or peak power of the laser. For this embodiment, lasers that produce short pulses with high intensity may be desirable, such as the output from mode locked lasers. Alternative laser approaches also exist, such as Q-switched lasers, cavity dumped lasers, and active or passive mode locking.

In another embodiment, the damage may be related to the optical absorption in the material, such as the optical absorption curves illustrated in FIGS. 1 through 7. For this embodiment, the damage can be proportional to the fluence or energy of the pulses, perhaps also the time-averaged power from the laser. The laser power may be absorbed in the particular tissue types, such as adipose, collagen and elastin, and the absorbed energy may then lead to heating within the tissue. For this example, continuous wave, pulsed, or externally modulated lasers may be used, such as those exemplified in FIGS. 8 through 12. In one embodiment, laser pulses that are longer than approximately 100 nanoseconds to as long as 10 seconds or longer may be employed.

Particularly in the example when the damage may be related to the optical absorption, it may be beneficial to also consider the thermal diffusion into the surrounding tissue. As an example, the thermal diffusion time into tissue may be in the millisecond to second time range. Therefore, for pulses shorter than about several milliseconds, the heat may be generated locally and the temperature rise can be calculated based on the energy deposited. On the other hand, when longer pulses that may be several seconds long are used, there can be adequate time for thermal diffusion into the surrounding tissue. In this example, the diffusion into the surrounding tissue should be considered to properly calculate the temperature rise in the tissue. For these longer pulses, the particular spot exposed to laser energy will reach closer to thermal equilibrium with its surroundings. In one embodiment corresponding to the data in FIG. 13, pulse widths of approximately 3 sec to 10 sec have been used. The local temperature achieved can also be affected by cooling. As described in the next section, when a cold window or cryo-spray is used, the cooling can remove heat from the top surface of the exposed tissue. Even with surface cooling, the laser power level may be adjusted so the heating depth reaches the area of interest while the cooling protects the regions above this area. Moreover, another adjustable parameter for the laser pulses may be the rise and fall times of the pulses. However, these may be less important when longer pulses are used and the damage is related to the energy or fluence of the pulses.

Beyond having a pulse width, the laser output can also have a preferred repetition rate. For pulse repetition rates above around 10 MHz, where multiple pulses fall within a thermal diffusion time, the tissue response may be more related to the energy deposited or the fluence of the laser beam. The separation between pulses or a sub-group of pulses may also be selected so that the tissue sample can reach thermal equilibrium between pulses. Also, the pulse pattern may or may not be periodic. In one embodiment, there may be several pulses used per spot, where the pulse pattern is selected to obtain a desired thermal profile. The laser beam may then be moved to a new spot and then another pulse train delivered to that spot. In one embodiment, there can be several seconds of pre-cooling, the laser can be exposed on the tissue for several seconds, and then there may also be post-cooling. Although particular examples of laser duration and repetition rate are described, other values may also be used consistent with this disclosure.

Laser Beam Delivery, Cooling and Fractionated Beam

A laser beam delivery assembly can advantageously be coupled to the mid-infrared laser, such as those shown in FIGS. 8-12. The design of the laser beam delivery system can be tailored to the ergonomic and comfortable usage by a medical practitioner. For example, there can be handles for easy gripping, switches or triggers that can be controlled by foot or fingers, and a flexible cord connecting the delivery head to the laser system. In one embodiment, the flexible cord can comprise a single-mode or multi-mode fiber, which may be used to couple the laser output to the delivery head or output port of the delivery assembly. The fiber in the flexible cord may be coupled using a connector to the laser output, and this can have the advantage that any damage in the delivery fiber may not require replacing the fiber in the laser system. Also, by using such a flexible cord and fiber assembly, the laser system can be located remotely from the delivery arm, such as under a table or on the floor, perhaps even in a different room than where the procedure is performed. In one preferred embodiment, a visible wavelength beam, such as from a helium neon laser, a light emitting diode or a semiconductor laser diode, may also be coupled to the delivery fiber. Since the mid-infrared wavelengths are not easily viewed by the medical practitioner, the visible beam can serve as a tracer beam, permitting the medical practitioner to observe where the laser beam may be incident on the tissue sample.

The laser beam delivery assembly may be non-invasive (e.g., applied externally to the body, such as in dermatology or ophthalmology) or minimally invasive (e.g., percutaneous or inserted into the body, such as to reach an organ or cardiology applications). In one embodiment, a non-invasive delivery arm may have light guided through a fiber in the flexible arm, and then the delivery head may have mirrors or lenses at the end to collimate or focus the light beam from the fiber onto the sample of interest. In a particular embodiment relating to dermatology, it may be desirable to have a spot size onto the tissue ranging in diameter from approximately 3 mm to 1 cm or more. In another embodiment relating to ophthalmology, it may be desirable to have a focusing arrangement at the delivery head. For example, the delivery head may have a tip that can be placed on the surface of the eyeball, and the focusing arrangement may be adjusted to focus the light from the mid-infrared laser into the cornea in a controlled manner such that the focus of the radiation can be at a predetermined depth. As one non-limiting example, the focusing elements may focus the laser to a depth of less than about 450 microns in the corneal tissue. In another preferred embodiment, the focusing element may create a beam waist at a depth of about 300 to 400 microns below the anterior of the corneal surface.

In one embodiment where the laser beam delivery assembly is used for applying light to the skin, eyeballs or externally to other organs, it may be advantageous to also have a cooling mechanism at the delivery head. For example, the cooling can protect the top layer of the skin, eyeball or organ and can remove heat from the top layers as light penetrates into the sample. In the dermatology example, the cooling can be used to protect the epidermis and the top layer of the dermis. For instance, the mid-infrared light may be used to cause selective damage at a depth of 1 to 3 mm, while the cooling protects the epidermis and top layer of the dermis. In one embodiment, the cooling can be achieved by using a cold window at the end of the delivery head. For example, the cold window can be a sapphire window. One advantage of sapphire material is that it can have a relatively high thermal conductivity and it can also be transparent in the mid-infrared wavelength range. Cooling can be achieved by flowing chilled water or other cooling fluid from a pumping system to the window at the end of the delivery head. As an example, the temperature at the head may be controlled by the flow rate or the temperature of the fluid bath at the pumping system. In yet another embodiment, a cryogenic spray system may be used to cool the tissue in the vicinity of the delivery head, and the timing of the sprays can be adjusted to achieve the desired cooling. In either case, there can be pre-cooling, simultaneous cooling, and/or post-cooling at the time of laser exposure to the tissue.

There may also be alternative designs for the laser beam delivery assembly for percutaneous or minimally invasive procedures, such as those used to reach an organ or artery in the body. The catheter or system for snaking into the body should be made relatively thin, and the flexible assembly should be capable of being manipulated by the medical professional external to the body to guide the catheter to the appropriate location. In one embodiment, there may be a radio opaque material at or near one end of the catheter, so the catheter can be guided using an x-ray or some other imaging system. The catheter may also comprise mirrors or lenses to collimate or focus the light either straight or at some desired angle. In some instances, it may also be desirable to have the catheter be rotatable over a range of angles. In another embodiment, the catheter may also have a camera or imaging system, so the medical professional can view on a monitor the image at the end of the catheter. In yet another embodiment, the catheter may also have a suction or removal system for removing debris or damaged tissue from in front of the catheter tip or surroundings. For example, it may be desirable to have a suction system to remove melted or damaged fat from around the catheter. This may be useful so the damaged adipose does not become self-limiting, in the sense that the fat in front of the laser beam can prevent the laser from further penetrating into the tissue. Although particular details of laser beam delivery have been discussed, additional elements or combinations can be used consistent with this disclosure.

For either the non-invasive or minimally invasive laser beam delivery system, other modifications may also be made, such as using a fractionated laser beam. In one embodiment, a fractional beam may thermally alter approximate microscopic treatment columns in the tissue, while leaving intervening areas of the tissue between the columns substantially undamaged. In this example, since only a fraction of the tissue can be modified, untreated areas may be able to repopulate the treatment columns, thereby reducing recovery time and avoiding adverse events. In one example, the fractionated laser beam can lead to beneficial procedures in dermatology. In one particular embodiment of skin tightening or rejuvenation, in the approximate columns where the laser beam is exposed, the exposed tissue may be in tension due to shrinkage of collagen by the heat generated by the laser beam. This tension then may close the voids, tightening the skin and reducing the wrinkles. Thus, in some embodiments the fractional laser beam treatment can shorten the wound healing process by allowing the tissue between the areas of the laser exposed to help in the recovery.

The fractionated laser beam may be added to the laser delivery assembly or delivery head in a number of ways. In one embodiment, a screen-like spatial filter may be placed in the pathway of the beam to be delivered to the biological tissue. The screen-like spatial filter can have opaque regions to block the light and holes or transparent regions, through which the laser beam may pass to the tissue sample. The ratio of opaque to transparent regions may be varied, depending on the application of the laser. In another embodiment, a lenslet array can be used at or near the output interface where the light emerges. In yet another embodiment, at least a part of the delivery fiber from the mid-infrared laser system to the delivery head may be a bundle of fibers, which may comprise a plurality of fiber cores surrounded by cladding regions. The fiber cores can then correspond to the exposed regions, and the cladding areas can approximate the opaque or areas not to be exposed to the laser light. As an example, a bundle of fibers may be excited by at least a part of the laser system output, and then the fiber bundle can be fused together and perhaps pulled down to a desired diameter to expose to the tissue sample near the delivery head. In yet another embodiment, a photonic crystal fiber may be used to create the fractionated laser beam. In one non-limiting example, the photonic crystal fiber can be coupled to at least a part of the laser system output at one end, and the other end can be coupled to the delivery head. In a further example, the fractionated laser beam may be generated by a heavily multi-mode fiber, where the speckle pattern at the output may create the high intensity and low intensity spatial pattern at the output. When referring to "coupling" in this disclosure, it is intended to cover both the cases of directly coupling and indirectly coupling (i.e., there can be additional intervening elements). Although several exemplary techniques are provided for creating a fractionated laser beam, other techniques that can be compatible with optical fibers are also intended to be included by this disclosure.

The discussion to this point in the disclosure has been more about the tissue properties, laser designs, laser output parameters, and delivery of the laser to a patient. In the following, applications of the laser to different medical fields and different tissue types will be described in more detail.

Collagen Shrinkage with Heating

Collagen connective tissue is ubiquitous in the human body and demonstrates several unique characteristics, including strength and resilience in various tissue types. It can provide the cohesiveness and tenacity of the musculoskeletal system, the structural integrity of the viscera, as well as the elasticity of the integument. Collagen fibers are composed of a triple helix of protein chains, with inter-chain bonds creating a crystalline structure for the collagen. When heated sufficiently, collagen can transform from the crystalline triple helical structure to an amorphous, random coil structure through the breakage of the hydrogen bonds linking the protein strands of the triple helix. This can create a thickening and shortening of the collagen fibers as the chains fold and assume a more stable configuration. Temperature elevation can result in contraction of the fiber to about two-thirds of their original lineal dimension (i.e., shrinkage by a third of the original dimension) without changing the structural integrity of the connective tissue. This collagen contraction can be used for a number of beneficial applications in vast areas including, but not limited to, ophthalmology and dermatology.

There is not necessarily a specific shrinkage temperature for collagen reaction. It is believed that the amount of collagen contraction could be related to a combination of the time and temperature. For example, for relatively long exposures of several seconds, the shrinkage temperature can be in the range of 60 to 70 degrees Celsius. It is believed that normal stabilized collagen fibers are stable up to a temperature of about 58 to 60 degrees Celsius. Also, normal tendon collagen can have a shrinkage temperature threshold which is about 2 to 4 degrees Celsius less than the corresponding threshold for skin collagen. Therefore, one aspect of this disclosure can be to raise the temperature of the collagen in the temperature range of approximately 60 to 70 C to create thermal shrinkage but not to raise the temperature too much higher, which could result in thermal damage to the collagen. Since the normal body temperature is about 37 C (98.6 F), this means the laser energy absorbed could raise the temperature between approximately 10 to 33 C, more preferably 23 to 33 C, or in one preferred embodiment between 23 to 28 C.

Application of Collagen Contraction to Ophthalmology

Figure 14:
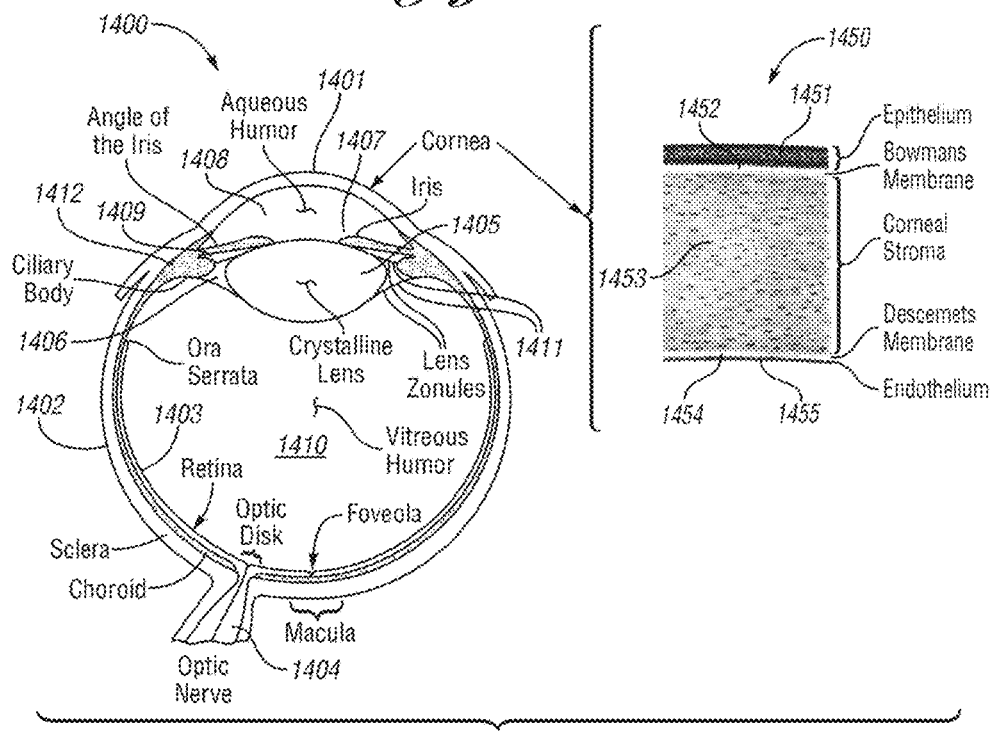
FIG. 14 illustrates a cross-sectional view of the human eye; the right side of the diagram is an enlarged view of the various layers comprising the cornea.

The cornea of the eye is a unique example of collagen connective tissue with the cornea stroma, which accounts for about 90% of the total thickness of the cornea, demonstrating a high transparency of cross-oriented sheets or lamellae of collagen (mostly type I collagen). To better understand this application, a review is first provided of the human eye structure. FIG. 14 (left side) is a horizontal section of an eye 1400 having a roughly spherical structure with a transparent cornea 1401 at the forward central portion, the remainder of the sphere of the "eyeball" being white and opaque sclera 1402 (often called the whites of the eye) that is attached to and blends in with the cornea periphery. The eye's light-sensitive retina 1403 extends along the rear and part of the forward inner surface of the sclera, and it is connected to an optical nerve 1404 that extends to the brain. The eye 1400 is disposed within any eye socket or orbit typically behind an eyelid.

Positioned behind the cornea is a crystalline lens 1405 supported by zonular ligaments 1406, and the lens is capable of shape changes that enable the eye to focus on objects at various ranges. The eye's iris 1407 is positioned between the cornea and lens to divide the space forward of the lens into an anterior chamber 1408 and posterior chamber 1409 that are filled with aqueous humor. The space behind the lens is filled with a clear gel-like body 1410 called the vitreous humor.

The right side 1450 of FIG. 14 is an enlargement of the corneal cross-section 1401 to show the various layers of the cornea. The outermost or anterior layer is the epithelium 1451 and its base membrane. The epithelium is typically about 50 microns thick and accounts for about ten percent of the total corneal thickness. The next layer is Bowman's membrane 1452, which is non-regenerative and which is about 10-13 microns thick in the human eye. The main body of the cornea is the stroma 1453, which accounts for about 90 percent of the total corneal thickness. The stroma is composed of clear sheets of collagenous material, and most of this is type I collagen. The stroma is backed by Descemet's membrane 1454, which is about 5-10 microns in thickness. Finally, the innermost or posterior layer of the cornea is the endothelium 1455, which is a single layer of non-reproducing flattened cells of about 4-5 microns thickness.

Although the geometry of the cornea is complex, it has surfaces that are approximately concentric and spherical, the radius of curvature of the outer or anterior surface typically being about 8 millimeters. The corneal diameter is about 11 mm, and the total thickness at the corneal center is about 0.55 mm (550 microns). Thus, the thickness of the stroma is in the range of 450 to 500 microns.

About three-fourths of the eye's refractive power can be determined by corneal curvature, and shape modification of this element of the eye's optical system thus provides a useful tool for correction of refractive errors. The change in shape can be provided by heating the collagen-rich stroma. However, a problem with heating the eye can arise in the possibility of damage to the epithelium and Bowman's membrane on the anterior side of the cornea, as well as Descemet's membrane and the endothelium on the corneal posterior. Therefore, it may be desirable to minimize the heating effects in these sensitive membranes while still obtaining the desired 60 C to 70 C temperature range in the stroma. Thus, it can be advantageous to have a laser wavelength that may be selectively absorbed in the collagen-rich stroma, such as mid-infrared wavelengths in the vicinity of 1720 nm. Other wavelengths can be used consistent with this disclosure as well, such as 1210 nm or around 2300 nm as non-limiting examples.

In one embodiment, an optional supplement to the mid-infrared laser exposure is to borrow on techniques similar to that used in Laser Assisted in-Situ Keratomileusis (LASIK) surgery. For example, in LASIK a corneal flap is created in some examples using a mechanical blade or a femto-second laser. In exemplary instances, the flap thickness may range between approximately 150 and 200 microns. Thus, the residual stroma left after the flap is of order of or greater than 250 microns. Then, in many cases an excimer laser is used to ablate at least a portion of the stroma to achieve the desired reshaping of the cornea.

Borrowing from these LASIK techniques, in one embodiment the corneal flap may be created, thus sparing the epithelium 1451 and vulnerable Bowman's membrane 1452 from the laser heating. With the flap lifted or put aside, the remaining corneal stroma 1453 may then be exposed to the mid-infrared radiation to achieve the desired collagen shrinkage to reshape the cornea. The selectivity can still be advantageous, so that the heating can be localized and damage to the Descemet's membrane 1454 and endothelium 1455 may be avoided.

Because of the selectivity in absorbing in the collagen-rich areas, one advantage of using mid-infrared wavelengths for light exposure could be that a flap-less LASIK type procedure could be performed, which would be relatively non-invasive. For example, most of the complications of LASIK surgery currently are associated with the cutting of the flap and healing of the flap after surgery. Also, infections of the eye can result from the cutting of the corneal flap. By exposing the corneal tissue and having absorption of the light energy directly in the cornea without cutting off the corneal flap, many of the complications of LASIK could be minimized. Although the amount of refractive index correction in the cornea may be more limited using the flap-less LASIK procedure, the non-invasive nature of the procedure should be attractive in many instances. Also, the flap-less LASIK procedure could benefit from top layer cooling using a cold window, as further described below.

Beyond using the selectivity of the mid-infrared wavelengths for ophthalmology procedures, it could also be beneficial to use surface cooling or a cold window to cool the surface of the eye before, during, and after exposing the laser light. This could still be a non-invasive procedure, since the cold window or surface cooling could be applied directly to the surface of the eye. As laser light is incident on the eye, the light energy may be highest near the outer surface, and then the light energy will decrease as the light penetrates further into the eye because of absorption and scattering. Hence, it is very likely that the outer layers of the eye are more vulnerable to heating damage. By surface cooling or placing a cold window next to the eye, the heat can be removed from the top layers, thereby lowering the possibility of thermal damage in the unwanted areas. This can enhance the collagen heating in the corneal stroma, while avoiding damage particularly in the epithelium and Bowman's membrane, as an example. Although surface cooling is described, many other embodiments to cool the top layers or conduct heat away could be used consistent with the disclosure. For example, a cryogenic spray could be used, where cold gases or emission is sprayed onto the surface of the eye.

Although several examples are provided for alternative techniques for mid-infrared laser usage in an ophthalmology procedure, there are numerous other techniques in ophthalmology that can benefit from using a mid-infrared laser for collagen shrinkage or localized, selective heating or damage. Another benefit of using mid-infrared laser light in ophthalmology applications, particularly at wavelengths near 1720 nm, can be that the wavelength lies in the eye safe wavelength range. For example, since the aqueous humor and vitreous humor do not transmit effectively wavelengths beyond approximately 1400 nm, using the mid-infrared light near 1720 nm can avoid or minimize risk of damage to the retina from residual radiation from the corneal reshaping procedure.

Also, other modifications to the laser exposure can be made and are included as parts of this disclosure. For example, the collagen shrinkage using mid-infrared light can be preceded by application of a reagent to the collagen tissue for reduction of the shrinkage threshold temperature. Examples of preferred reagents include hyaluronidase and lysozyme. It has been reported that with application of such reagents that the collagen shrinkage temperature can be lowered by 10 C to 12 C. This has advantages because it means less laser energy can be deposited in the stroma. Thus, there can be less chance of damage to the surrounding tissue. Moreover, the gap between collagen shrinkage energy and collagen damage energy can be enlarged. Although one example is shown of modifying the collagen shrinkage procedure, any number of improvements in terms of spatial focusing, additional chemical applications, or laser alternations can be made consistent with this disclosure and are intended to be covered by this disclosure.

In yet another embodiment, the mid-infrared light treatment may be accompanied by techniques to prevent or minimize regression of collagen shrinkage. If the collagen of the stroma or other sections of the eye are damaged sufficiently, then the body may react using, for example, its natural wound healing processes. Consequently, loss of the collagen shrinkage effect as a function of time, otherwise known as regression of the desired effect, can result from the wound repair process. Several techniques may be used to try to minimize the regression. In one example, by controlling the exposure time and power level or fluence of the mid-infrared appropriately, collagen shrinkage might be obtained without the damage that leads to the wound repair mechanisms. In this instance it may be advantageous that the light can be absorbed selectively in the collagen-rich stroma and that by being near the peak of the local absorption, the heating can be accomplished more efficiently. In addition, the cooling of the outer layers of the eye may also be advantageous, since damage in the outer layers may be avoided, thereby not leading to the body initiating a wound healing process. In a further embodiment, pre-heating or pre-cooling may lead to a shock response in the eye, which then increases the tolerance of the eye to laser treatment, thereby increasing the threshold for the wound healing processes. In yet another embodiment, chemicals may be applied to the eye that may counter-act or inhibit the wound healing mechanisms in the eye. The goals of such procedures may be to increase the time or permanence of the collagen shrinkage effect.

Treatment Examples in Ophthalmology

Keratoconus can be one example of applying the above concepts to the field of ophthalmology. Keratoconus is a degenerative disorder of the eye where structural changes within the cornea cause it thin and change to a more conical shape than its normal gradual curve. It is typically diagnosed in the patient's adolescent years and attains its most severe state in the twenties and thirties. Keratoconus is the most common dystrophy of the cornea, affecting around one person in a thousand. Also, between 10% and 25% of cases of Keratoconus will progress to a point where vision correction is no longer possible, thinning of the cornea becomes excessive, or scarring as a result of contact lens wear causes problems of its own.

Alternative laser-based procedures are needed because LASIK can be incompatible with Keratoconus and other corneal thinning conditions as removal of corneal stromal tissue will further damage an already thin and weak cornea. Contact lenses are the primary treatment for most patients with Keratoconus. Severe cases may require corneal transplantation. This is a surgical procedure that replaces the Keratoconus cornea with healthy donor tissue. In this process much of the central cornea of the Keratoconus patient is removed and is replaced with the cornea of a recently deceased person.

Some newer technologies may use high frequency radio energy, where the energy shrinks the edges of the cornea, which in turn pulls the central area back to a more normal shape. The procedure is known as Conductive Keratoplasty, which uses radiofrequency to strategically heat and shrink tiny parts of the collagen in the cornea. However, the radio frequency energy cannot be highly focused, and the radio frequency heating may heat anything with water content, which may not be selective to the stroma. Also, this is not a non-invasive procedure, since needles or antennas are inserted into the eye to localize the RF energy in certain regions.

An advantageous treatment for Keratoconus that may avoid the need for corneal transplantation could be to use the collagen shrinkage techniques described above. For example, the mid-infrared light can be focused using an appropriate lens system, and the beam waist could be tailored to lie around the middle of the stroma, in one embodiment in the range of 300 to 400 microns depth below the anterior corneal surface. Also, the mid-infrared light could be focused around the edges of the cornea in the stroma, collagen-rich areas, so that the collagen shrinkage may shrink the edges of the cornea and pull the cornea back to a more normal shape. In an alternate embodiment, the mid-infrared light could be focused closer to the center of the corneal stroma, thereby, for example, shrinking the center peak in the cornea. In one example, the stroma could be heated to a temperature in the range of 60 C to 70 C, while minimizing heating in the surrounding sensitive membranes, particularly in the endothelium.

The stroma can be selectively heated using a combination of two effects. First, selecting a wavelength corresponding to a collagen peak with less water absorption can cause more heating in the collagen-rich stroma. Second, by focusing the mid-infrared laser beam toward the center thickness of the stroma, the light intensity (power per unit area) can be higher in the stroma than in the surrounding membranes. In one preferred embodiment, the laser beam can have a beam waist that is approximately centered on the stroma central thickness, and the focal spot size can be adjusted so that the confocal parameter or Rayleigh range (i.e., the distance over which the beam diffracts to twice its smallest beam waist) is adjusted to be approximately less than the thickness of the corneal stroma, which is of order of 450 microns. Earlier reports claim that the collagen shrinkage appears to be permanent, with the potential of little or no lasting opacity of the treated site resulting from the mid-infrared light exposure. If the collagen shrinkage is not permanent, then the non-invasive procedure can be repeated after some length of time. For example, a Keratoconus patient may return for mid-infrared laser treatment every six months to touch-up any reshaping of the corneal layer. In yet another embodiment, some of the techniques described earlier for preventing regression can be used in conjunction with the collagen shrinkage procedure.

Although Keratoconus is described as one non-limiting example, there are many other ophthalmology procedures where the collagen shrinkage with laser exposure can be advantageously used. For example, in one embodiment the collagen shrinkage with heating could be useful for promoting collagen cross-linking. In the collagen cross-linking, new bonds can form across adjacent collagen strands in the stromal layer of the cornea, which recovers and preserves some of the cornea's mechanical strength. In one embodiment, the cross-linking could be used to attach cornea transplants or to join segments of cornea that are separated for any reason.

In yet another embodiment, different refractive index changes in the cornea or "refractive power correction" can be corrected by proper spatial placement of the laser beam exposed regions. For example, to correct for hyperopia (far-sightedness or long-sightedness), it may be advantageous to have the laser beam focused at locations on the side or periphery of the cornea. For example, in hyperopia it may be desirable to increase the steepness of the cornea to increase the refractive lens power. On the other hand, to correct for myopia (near-sightedness or short-sightedness) it may be advantages to have the laser beam focused closer to the center of the cornea. For instance, for myopia treatment it may be desirable to flatten the center of the cornea to decrease the refractive power of the cornea, and in one embodiment a diameter of approximately 6 mm may be used around the center of the cornea. Since myopia is among the most common eye ailments, treating myopia using mid-infrared light in an approximately non-invasive procedure may have a large impact. However, since the center of the cornea is more likely to be exposed to mid-infrared radiation in treating myopia, it may be important to control the laser exposure time, power level or fluence, so that damage and opacity can be avoided in the cornea and surrounding areas. As the collagen shrinkage is accomplished using the mid-infrared light, some of the issues to monitor include the clarity of the corneal layer after laser treatment and any damage to the outer layers, such as the epithelium or Bowman's membrane. Surface cooling or application of a cold window, for example, could also help in avoiding damage to the outer layers.

Although LASIK is a widely used procedure, it is contraindicated in any of the corneal thinning conditions, or conditions where the cornea is weakened. Consequently, one general area where collagen shrinkage with mid-infrared light exposure can be advantageously used is in procedures involving a thinned or weakened corneal layer. Also, since the mid-infrared light exposure can be non-invasive (e.g., it does not necessarily require the moving back of a corneal flap, such as in LASIK), the collagen shrinkage procedures can be performed on patients to trim or slightly modify the corneal shape. The non-invasive procedure may also be accompanied by surface cooling or a cold window to avoid damage to the eye. Also, some of the techniques for avoiding regression may also advantageously be used. One advantage of the collagen shrinkage technique may be the reversibility of the change, so long as the collagen shrinkage is achieved without damage. This may be valuable if, for example, proper refractive power correction is not achieved during the procedure.

It will be appreciated that there are many other corneal procedures that can benefit from this non-invasive technique. For example, astigmatism may be corrected by having laser light resonant with the collagen absorption. As one other non-limiting example, the collagen shrinkage may be beneficial in treating presbyopia. Presbyopia is often called "old eye" and is experienced in many people starting around the age of 40-50 years. With presbyopia, it often becomes harder to focus on small objects at close distance. As one ages, the lens 1405 can become less malleable or the capsule less elastic; consequently, the lens 1405 may not assume a greater curvature in spite of the reduced tension of the zonules 1411 upon the lens.

The ciliary muscle or body 1412 is a smooth muscle in the eye that controls the eye's accommodation for viewing objects at varying distances. The circular ciliary muscle fibers 1412 affect zonular fibers 1411 in the eye (fibers that suspend the lens in position during accommodation), thereby enabling changes in lens shape for light focusing. For example, when the ciliary muscle 1412 contracts, it pulls itself forward and can move the frontal region toward the axis of the eye. This can release the tension of on the lens by the zonular fibers 1411, thus causing the lens to become more spherical and able to adapt to shorter range focus. On the other hand, relaxation of the ciliary muscle 1412 can cause the zonular fibers 1411 to become taut, flattening the lens, and thus increasing the long range focus.

In one particular embodiment, an at least partial treatment for presbyopia can result by exposing at least parts of the ciliary muscle or body 1412 and/or the zonular fibers 1411 to mid-infrared light. By utilizing the shrinkage of collagen connective tissue at the site of the ciliary muscle 1411 and zonular fibers 1412, the ability to control the curvature of the lens 1405 or to accommodate an enlarged lens 1405 could be improved. For instance, by shortening or shrinking the tendinous portions of the ciliary musculature 1411 to increase its mechanical advantage, it may be possible to overcome the physiologic laxity in the accommodative function brought about by presbyopia. Moreover, the collagen shrinkage could also assist in more accommodating motion of the lens 1405 by tightening the trabecular meshwork of the aqueous filtration mechanisms in the region near the ciliary 1411. Note, however, that these regions of the eye lie below the sclera tissue 1402. One potential advantage of using mid-infrared light that may be selectively absorbed in collagen can be that the light can transmit through the sclera 1402 to the regions near or surrounding the collagen tissue in the ciliary muscle 1411 and zonular fibers 1412. Consequently, the procedure to treat presbyopia could be substantially non-invasive. The mid-infrared light treatment can be combined with any number of the techniques described in this specification. For example, it may be advantageous to also use surface cooling over the sclera 1402 to avoid thermal damage in this tissue layer. Also, chemicals, drugs or other techniques to avoid or minimize regression may be used advantageously with the mid-infrared light treatment.

Selective Damage in Dermatology

Figure 15:
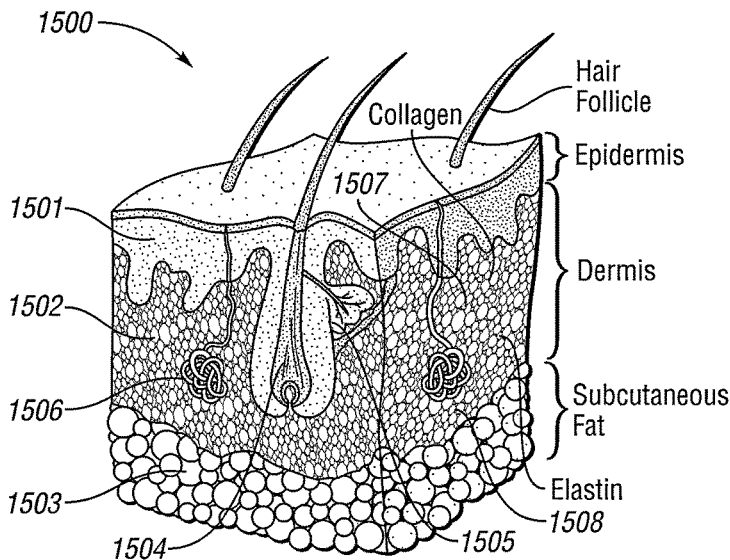
FIG. 15 is a schematic of some of the main layers of the human skin; for example, the dermis comprises collagen and elastin.

Another example of the application of mid-infrared lasers for selective damage to the human body is in dermatology. Before describing this application in more detail, a review is first provided of the skin, which is the largest organ in the body and comprises about 15 percent of the body weight. The skin 1500 is composed on three main layers: epidermis 1501, dermis 1502, and subcutaneous tissue 1503 (FIG. 15). The epidermis 1501 is the topmost layer of the skin, and it comprises three types of cells: keratinocytes, melanocytes and Langerhans cells. Keratinocytes, the cells that make the protein keratin, are the predominant type of cells in the epidermis. The total thickness of the epidermis is in the range of 0.1 to 1 mm, depending on the location on the body. At the lowermost portion of the epidermis are immature, rapidly dividing keratinocytes. As they mature, keratinocytes lose water, flatten out, and move upwards. At the end of their life cycle, they reach the uppermost layer of the epidermis call the stratum corneum. The stratum corneum is made up mostly of dead keratinocytes, hardened proteins (keratin) and lipids, thereby forming a protective crust. Dead cells from the stratum corneum continuously fall off and are replaced by new ones coming from below. In fact, the skin completely renews itself every three to five weeks.

Another group of cells in the epidermis 1501 are the melanocytes, which produce melanin, the pigment responsible for skin tone and color. Finally, Langerhans cells are part of the immune system of the epidermis, and they prevent unwanted foreign substances from penetrating the skin.

The dermis 1502 is the middle layer of the skin located between the epidermis and subcutaneous tissue. It is the thickest of the skin layers and comprises a tight, sturdy mesh of collagen 1507 and elastin fibers 1508. Both collagen 1507 (mostly Type I) and elastin 1508 play a big role in the skin function: collagen is responsible for the structural support and elastin for the resilience of the skin. The fibroblasts in the dermis synthesize collagen, elastin and other structural molecules.

The dermis also contains capillaries and lymph nodes. The former help to oxygenate and nourish the skin, while the latter help to protect the skin from invading microorganisms. In addition, the dermis contains sebaceous glands 1505, sweat glands 1506, hair follicles 1504, as well as a relatively small number of nerve and muscle cells. Sebaceous glands 1505 are lipid-rich glands, which are located around hair follicles 1504. The sebaceous glands 1505 produce sebum, which is an oily protective substance that lubricates and waterproofs the skin and hair. Overproduction of sebum can lead to skin ailments, such as oily skin or acne.

Subcutaneous tissue 1503 is the innermost layer of the skin located under the dermis 1502 and comprising mostly fat or adipose. The predominant type of cells in the subcutaneous tissue 1503 is adipocytes or fat cells. Subcutaneous fat 1503 acts as a shock absorber and heat insulator, protecting underlying tissues from cold and mechanical trauma.

Figure 16:
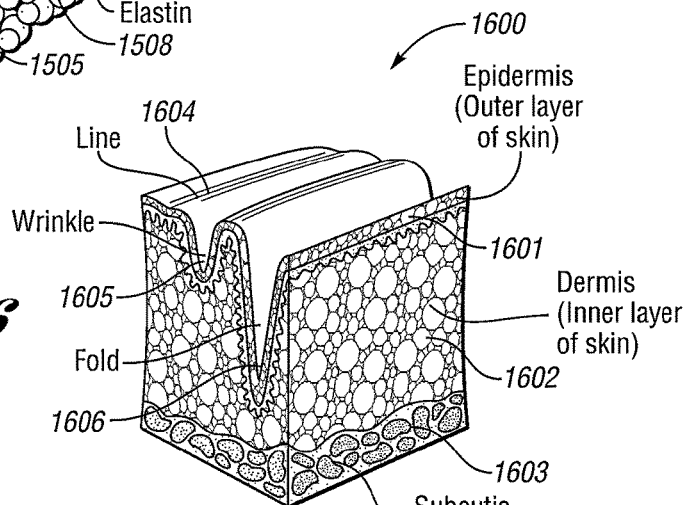
FIG. 16 shows an exemplary sketch of human skin and the definitions of a skin line, skin wrinkle and skin fold.

The dermis 1502, 1602 is the layer of the skin 1600 responsible for the skin's structural integrity, elasticity, and resilience. Wrinkles 1605 arise and develop in the dermis (FIG. 16). Wrinkles 1605 are mainly formed by the distortion of the dermis 1602 due to loss of elasticity induced by decrease of collagen and elastin fibers. Therefore, an anti-wrinkle treatment can be effective in one embodiment only if the treatment can reach as deep as the dermis. For example, light treatments that use a wavelength of light that do not penetrate down to the dermis will probably not be efficacious in treating wrinkles 1605. Also, typical collagen and elastin topical creams are not generally effective because collagen and elastin molecules are too large to penetrate the epidermis 1601.

Non-Ablative Skin Rejuvenation, Tightening, Wrinkle Removal

Non-ablative, non-invasive skin tightening, skin rejuvenation and wrinkle removal could be advantageously accomplished using mid-infrared light. The dermis 1501, 1602 is composed mainly of collagen 1507, elastin 1508 and sebum. Both collagen 1507 and elastin 1508 can be responsible for renewing skin cells and maintaining a youthful appearance of the skin. Skin tightening has been achieved in earlier systems, for example, using either radio frequency or flash lamp systems. In the radio frequency systems, the RF is absorbed in the subcutaneous fat layer 1503, and the heat generated from this transfers to the dermis 1502 and is used for stimulating collagen growth. On the other hand, flash lamp systems with light covering approximately 1100 to 1800 nm have been used for skin rejuvenation, but these systems try to trigger new collagen growth by using collagen contraction through heating of the surrounding water in the dermis 1502 and then transfer of this heat to the collagen. However, both of these systems can be inefficient and may deliver too much energy to the skin, leading to potential unnecessary harm to the epidermis 1501 or pain to the patients undergoing the treatment.

In one embodiment, a more efficient use of the laser light can be achieved by using wavelengths in the vicinity of local peaks in absorption of the constituents of interest in the dermis 1502, 1602. For example, as FIG. 7 illustrates, collagen 703 elastin 704 and adipose 702 all can have a local peak absorption near 1720 nm 706. This window also can correspond to a local minimum in water absorption 701, and the scattering can also be low at the longer wavelengths. Another exemplary wavelength window can be in the neighborhood of 1210 nm 705: however, the peaks may not be as precisely lined up, the absorption of collagen 703, elastin 704 and adipose 702 appears to be considerably weaker, the water 701 can have a local peak in absorption in this window, and the scattering through the tissue can be higher at this shorter wavelength.

In the embodiment using mid-infrared light near 1720 nm 706, the light can be preferentially absorbed in the collagen 703, elastin 704, and adipose or sebum/adipose 702, leading to the desired heat generation in the dermis. The heat generated can then lead to collagen contraction as well as rejuvenation of the collagen 1507 and elastin 1508 tissue. The heated collagen can transform from the crystalline triple helical structure to an amorphous, random-coil structure through the breakage of the hydrogen bonds linking the strands of the triple helix. Hence, non-ablative skin rejuvenation, skin tightening and/or wrinkle removal can be achieved with potential efficient use of the optical energy.

Another advantageous aspect of using mid-infrared light for skin treatment can be that a deeper penetration into the skin can be achieved. The epidermis 1501 may be of order 0.1 mm thick, while the dermis 1502, 1602 can be about 4 mm in thickness. For treatment of the dermis 1502, 1602, it may be desirable for the heat penetration depth to be about 1 to 2 mm, perhaps with some heating down as far as 4 or 5 mm. In one particular embodiment, penetration of laser light in the depth range of approximately 0.5 mm to 1.5 mm may be desirable. In another preferred embodiment, the heating can reach down to the middle or bottom of the dermis layer 1502, 1602. Based on the water absorption 402 and scattering 401 through skin tissue (FIG. 4), the penetration depth into the skin 1500 can be estimated. For example, as shown in FIG. 5, the total absorption and scattering coefficient 501 can be approximately 6.8 cm$^{-1}$ at 1210 nm, which corresponds to an absorption length (inverse of the coefficient) of about 1.47 mm. Thus, the light penetration at 1210 nm can be of order one to three absorption lengths, or approximately 1.5 mm to 4.5 mm in depth. On the other hand, the total absorption and scattering coefficient 501 can be approximately 8.25 cm$^{-1}$ at 1720 nm, which corresponds to an absorption length of about 1.2 mm. Thus, the light penetration at 1720 nm can be approximately 1.2 mm to 3.6 mm, which should be comfortably within the mid-range of the dermal layer 1502, 1602. As an example, one advantage of heating to a depth of 1 to 2 mm can be that the dermal collagen fibers 1507 can be targeted while allowing a cooling mechanism to protect the epidermis 1501.

The curves in FIG. 7 can lead to preferred embodiments for selective damage using mid-infrared lasers in the wavelength window near 1210 nm 705 or 1720 nm 706. Of these two window options, in some instances it may be advantageous to select the longer wavelength window near 1720 nm 706. For example, one reason for selecting this longer wavelength window may be to operate in the so-called "eye-safe" wavelength range, which can correspond to wavelengths longer than approximately 1400 nm. A second advantage of the longer wavelength window near 1720 nm 706 for dermatology applications can be that the peaks for the major constituents of dermis—namely, collagen, adipose and elastin—all approximately line up near 1720 nm 706. Therefore, the heat generation can be synergistic from optical absorption in all these constituents. Finally, for dermatology the efficiency of the optical energy delivery can be better at 1720 nm 706 than at 1210 nm 705. For example, the efficiency can be higher when the loss or absorption length (inverse of the absorption coefficient) is approximately matched for the propagation through skin tissue from water absorption and scattering 701 and, for example, the absorption length in adipose tissue 702. At 1720 nm 706, for instance, the absorption length from water absorption and scattering can be 1.2 mm (8.25 cm$^{-1}$ absorption coefficient), while the absorption length for adipose can be approximately 1.12 mm (8.5 cm$^{-1}$). On the other hand, at 1210 nm 705, the absorption length from water absorption and scattering can be 1.47 mm (6.8 cm$^{-1}$), while the absorption length for adipose can be approximately 5 mm (2 cm$^{-1}$). For light excitation of adipose, 1720 nm 706 can be more efficient than at 1210 nm 705. At 1210 nm the light can be lost more rapidly due to water absorption and scattering 701 in the tissue, and because of the weaker absorption in adipose more light energy will probably be required. To achieve the same results, a higher laser power exposure will probably be required at 1210 nm 705, which could also mean that the epidermis 1501 and upper dermis layers 1502 are more susceptible to damage or scarring.

Other Advantageous Dermatology Applications

Yet another embodiment of a procedure that could benefit from using a mid-infrared selective laser is stretch mark or striae removal. Stretch marks, also called striae, are a common problem affecting a majority of women who have had children. For example, during pregnancy the skin of the abdomen stretches to many times its normal size as the baby grows. After the baby is delivered, the skin's elasticity in the dermis contracts to bring the abdomen skin back to its normal shape. During skin stretching, if the dermis expands too much or too fast, the dermis can break, split or rupture. These breaks in the dermis of the skin cause a wide depressed scar, which is called a stretch mark or striae.

Also, in recent years, the use of steroids has caused stretch marks in many young men who have worked very hard at body building and fitness. The use of steroid medications also causes striae even without tension or pulling on the skin. The mechanism of the striae caused by steroids can be a direct damage or dissolving of collagen in the dermis by the steroid medication. In addition, rapid growth spurts during adolescence or even in adults who are weight lifting and have rapid muscle expansion, can also cause rupture of the dermis and striae.

In one embodiment, repairing stretch marks and striae can require building new collagen 1507 in the dermis 1502, 1602 of the skin to replace the lost collagen and tightening of the skin to bring the stretched skin back together. This may be accomplished by heating using a mid-infrared laser system. For example, when the collagen is heated to a temperature in the range of 60-70 C, the collagen can shrink and tighten, and the collagen can be stimulated to remodel and grow new collagen. It can also be advantageous to have a treatment where the laser heating penetrates sufficiently deep into the dermis 1502, 1602, for example in the range of 1 to 2 mm. The dermis layers 1502, 1602 are where the collagen regeneration and elasticity of the skin can be most effective to recover from the stretch marks or striae.

Another aspect of this disclosure is that the selective absorption in collagen, elastin and adipose can be advantageously used for laser skin resurfacing to treat various kinds of skin flaws, such as sunburns, wrinkles, acne and acne scar removal. Such skin flaws are often treated using dermabrasion, which entails removing the topmost layer of the skin via a sanding procedure. However, this procedure is quite painful, often requiring the use of local anesthesia while applying to a patient. After such a procedure the skin can be raw and painfully tender, and new skin could take months to grow back. An alternative procedure may be to use chemical peels, which can use chemicals that cause the skin to blister and finally peel off.

A non-ablative laser procedure could be less painful and more efficacious for patients with skin flaws. A mid-infrared, non-ablative, laser procedure could work beneath the skin 1500, 1600 surface, stimulating collagen production and tightening the overall tissue. Another advantage of a laser-based technique can be that the laser beam can be targeted or localized to the region of interest, for example on the face or body of the patient. Yet another advantage of a selective laser damage technique can be that the patient can have a faster recovery time and less redness of the treated region, since the selective laser can lead to less damage to vascular fibroblast.

In one non-limiting example, the selective laser procedure can be used with patients afflicted with acne and the resulting acne scar tissue. The root cause of acne can be excess sebum production in the lipid-rich sebaceous glands 1505, which lie near the side or bottom of a hair follicle 1504. The sebaceous glands 1505 that cause acne typically lie in the region about 0.25 to 1.5 mm below the skin surface. Incidentally, the excess sebum production can also lead to other skin ailments, such as oily skin. Unfortunately, acne can leave behind unsightly and even disfiguring scars. Patients afflicted with acne and the resulting scars may benefit from a mid-infrared skin treatment that can selectively target and comprise light absorbed in collagen, elastin and adipose. In one embodiment, mid-infrared light near 1720 nm can be advantageously used, since the penetration depth can be well matched to the depths of the sebaceous glands 1505. In one non-limiting example, the mid-infrared light can be selectively absorbed in the sebaceous glands 1505, thereby halting the excess sebum production. In addition, the selective absorption in the collagen 1507 and elastin 1508 of the dermis can be used to help repair the skin flaws. For example, with the collagen shrinkage and stimulating collagen production, the acne scar tissue can be replaced with new skin. Therefore, the selective absorption of the mid-infrared light in the dermis has the potential to treat the root cause of acne as well as repair the acne scar tissue.

Although a few dermatology applications have been described, there are many other applications of the mid-infrared light in dermatology that are intended to be covered by this disclosure. Therefore, the listed procedures are provided by way of example, but the disclosure could also cover many other dermatology applications. For example, yet another dermal application that can benefit from mid-infrared light resonant with the collagen, elastin and adipose is wound healing or dermal remodeling. For example, stimulation of collagen bio-synthesis is often desirable in the early stages of wound healing. The heating through selective absorption in the collagen, elastin and adipose near the wound region can lead to collagen contraction and skin rejuvenation.

Combining Mid-Infrared Light with Other Dermal Techniques

In describing the dermatology applications, the above description has just described using the mid-infrared laser light (exemplary near 1720 nm, possibly 1210 nm) directly to the skin to have selective absorption in the dermis in the collagen, elastin and adipose. However, this disclosure is intended to cover combining the mid-infrared laser treatment with any number of temporal, spatial or procedural techniques that are known to be used in dermatology. In one embodiment, it is contemplated that the laser treatment can be done at different time periods. For example, it can be likely that the non-invasive tissue mechanisms relate both to the immediate as well as delayed effects on collagen. Although initial research studies presumed the collagen shrinkage to be irreversible, newer evidence suggests that the melting temperature of collagen can be actually lower than 37 C, and that there may be a tendency for reversibility. Collagen melting occurs at body temperature but the time intervals are relatively long. Consequently, the collagen shrinkage effect may be reversed after several weeks or months. Therefore, it may be necessary to repeat the collagen shrinkage every several weeks or every several months, depending in part on the severity of the skin changes.

In yet another embodiment of combining different dermatological procedures, it is likely that the mid-infrared light exposure may have to be combined with protecting the epidermis 1501 and top layer of the dermis 1502 using external cooling, such as a cold window or cryospray. In most non-invasive, non-ablative laser dermatology procedures, external cooling is used to protect the epidermis 1501 and top layer of the dermis 1502. There can be pre-cooling, cooling in parallel with the laser exposure, and post-cooling. Therefore, the cooling of the skin top layer is contemplated as part of this disclosure of applying mid-infrared light to the skin to selectively absorb. One benefit of selective absorption in collagen, elastin and adipose can be that the procedure may result in less pain to the patient. For example, techniques that rely on absorption in water often require more energy and can also be more painful, since water is throughout the skin. With the selective absorption at the mid-infrared wavelengths, less collateral heating can occur, which can reduce the pain level experienced by the patient. Nonetheless, it still may be desirable to use a local anesthetic to lower the pain felt by a patient when exposing the laser light.

Another embodiment of using the mid-infrared laser treatment may also be to combine the selective absorption with a fractionated laser beam. The fractionated laser beam comprises an array of microscopic beams. With this array pattern for the beam, the laser can be adapted to make tiny wounds in the dermis layer to trigger the nature healing abilities of the body. Although several laser procedures may be required, it is believed that making the micro-laser damage spots may enhance the recovery of the skin because the undamaged skin surrounding the laser spots will aid in the recovery. It is contemplated that using a fractionated laser beam with the mid-infrared light near wavelengths such as 1210 nm or 1720 nm can be within the scope of this disclosure.

Yet another embodiment of using mid-infrared laser can be to combine the laser exposure with topical creams or other substances applied to the skin surface. For example, in some procedures it might be desirable to apply keratin or a related compound to the skin surface, which can also aid in the collagen or elastin rejuvenation. In another example, polypeptide growth factors may be applied to the skin, as they are believed to play a role in skin healing. In yet another example, local anesthetics may be applied to the skin or a cool pack to relieve pain associated with the light exposure.

In yet another embodiment, the time exposure of the mid-infrared laser may be varied to obtain different effects. For example, in some instances the pain felt by the patient can be reduced by using lower fluence (one example being in the range of less than 30 J/cm$^2$) but for longer periods of time, for example of order 10 seconds. If the time of exposure to the laser is very short compared to the time required for heat to diffuse out of the area exposed, namely the thermal relaxation time, then the temperature rise at any depth in the exposed tissue can probably be proportional to the energy absorbed at that depth. On the other hand, if the pulse width is comparable or longer to the thermal relaxation time of the exposed tissue, then the profile of temperature rise may not be as steep. Conduction of thermal energy can occur at a rate proportional to the temperature gradient in the exposed tissue. Consequently, lengthening the exposure time may reduce the maximum temperature rise in exposed tissue. Different temporal patterns for the mid-infrared light are intended to be covered in this disclosure.

Although several embodiments of combining the mid-infrared laser exposure with other dermatology techniques are described, other combinations are also intended to be covered by this disclosure. Also, combinations of these techniques can also be used consistent with this disclosure.

Adipose Tissue And Type 2 Diabetes

With the growing epidemic of obesity in much of the industrialized countries, a growing number of human ailments are associated with adipose tissue (i.e., fatty tissue) building up excessively both inside and outside organs, arteries, and other parts of the body. One alarming statistic is that the prevalence of obesity in children has increased fairly dramatically over the last 20 to 30 years. Moreover, the prevalence of type 2 diabetes has also increased rapidly over the last 20 years. For example, the incidence of type 2 diabetes in adolescents has been estimated to increase ten-fold from 1982 to 1994 in the greater Cincinnati area. In addition, a significant number of obese youth have abnormally severe insulin resistance with an attendant increased risk of developing type 2 diabetes mellitus. In fact, there is a growing recognition that visceral or intra-peritoneal fat can be strongly associated with insulin resistance and other factors. In one embodiment, the mid-infrared light could be used to melt or damage the visceral or intra-peritoneal fat, thereby potentially reducing the risks associated with and incidence of type 2 diabetes in children, adolescences and adults. The mid-infrared light could also be used to render the adipose tissue inactive, in the sense that cytokines are no longer generated by at least some of the adipose tissue.

In humans, adipose tissue is located beneath the skin (subcutaneous fat), around internal organs (visceral fat), and in the bone marrow (yellow bone marrow). Adipose tissue is found in specific locations, which are referred to as 'adipose depots.' Adipose tissue contains several cell types, with the highest percentage of cells being adipocytes, which contain fat droplets. In the integumentary system, which includes the skin, adipose accumulates in the deepest level, the subcutaneous layer, providing insulation from heat and cold. Around organs, it provides protective padding.

Visceral fat or abdominal fat, which is also known as organ fat or intra-abdominal fat, can be located inside the abdominal cavity, packed in between internal organs and torso. The visceral fat is composed of several adipose depots including mesenteric, perigonadal, epididymal white adipose tissue and perirenal depots. An excess of visceral fat is known as central obesity, or "belly fat", in which the abdomen protrudes excessively. There is a strong correlation between central obesity and cardiovascular disease. For example, adipose tissue secrete a type of cytokines (cell-to-cell signaling proteins) called adipokines or adipocytokines, which play a role in obesity-associated complications and cardiovascular diseases.

Central obesity is associated with a statistically higher risk of heart disease, hypertension, insulin resistance and type 2 diabetes mellitus. It is speculated that central obesity predisposes individuals to insulin resistance, and it may also be that the adipokines secreted by abdominal fat may impair glucose tolerance. Insulin resistance is a major feature of type 2 diabetes, and central obesity is correlated with both insulin resistance and type 2 diabetes. For example, increased obesity raises serum resistin levels, which in turn correlates with insulin resistance. Studies have also confirmed a correlation between resistin levels and type 2 diabetes.

In one embodiment, a mid-infrared fiber laser could be used to remove or damage at least some amount of visceral or abdominal fat, thereby reducing the probability of type 2 diabetes and insulin resistance. The removal or damage of the adipose can also reduce the cytokines and/or serum resistin secretion or generation, which can also potentially reduce some of the type 2 diabetes and cardiovascular complications. The selectivity of using mid-infrared wavelengths can be valuable, because the desire is to remove or damage the adipose without damaging the organs that are surrounded by the adipose or surrounding blood vessels. For example, it has been contemplated to use a liposuction type technique for removing visceral fat. In such a procedure, however, extreme care would be required to avoid damaging or accidentally removing parts of the organs below the adipose layers or damaging blood vessels. Moreover, most laser wavelengths used in medical procedures usually rely on water absorption, and then transferring the heat to the adipose tissue. Adipose tissue actually has very little water content. Therefore, use of these other laser wavelengths would heat the organ tissue or blood, which could lead to damaging the organ tissue or blood vessels while trying to remove the adipose surrounding the organ. Compared with using liposuction or other laser wavelengths relying in on water absorption, using lasers at wavelengths where the adipose tissue absorption exceeds water absorption (e.g., around 1210 nm, 1720 nm or 2300 nm) could be advantageous for removing adipose around organs while minimizing damage to the organs or blood vessels.

Figure 19:
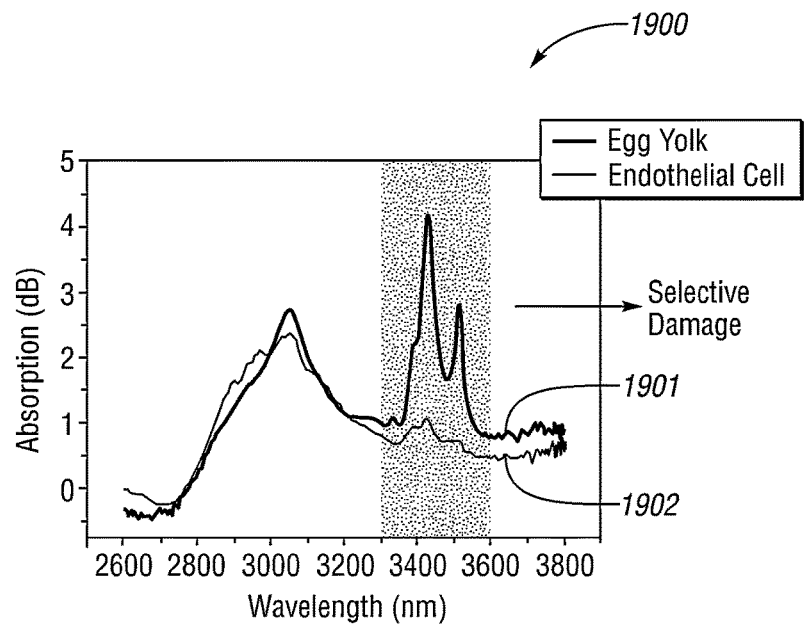
FIG. 19 illustrates the optical absorption of egg yolk and endothelial cells; for example, by using light in the wavelength range near 3300 to 3600 nm, the egg yolk can be selectively damaged compared with endothelial cells.

In one preferred embodiment, a cascaded Raman oscillator operating near 1720 nm may be used to the first overtone band of the fatty acid band (c.f. FIG. 19). In another embodiment, a cascaded oscillator operating near 1210 nm or 2300 nm could also be used to remove or damage the adipose tissue. A light source near 3400-3500 nm could also be used, although in this wavelength range has more water absorption, so care should be taken to avoid water between the laser emission point and the adipose tissue. Although cascaded Raman oscillators are mentioned, other lasers could also be used consistent with the disclosure. For example, laser diodes, fiber lasers, quantum cascade lasers, solid state lasers, or modelocked lasers could also be used in the therapeutic procedures.

Figure 20:
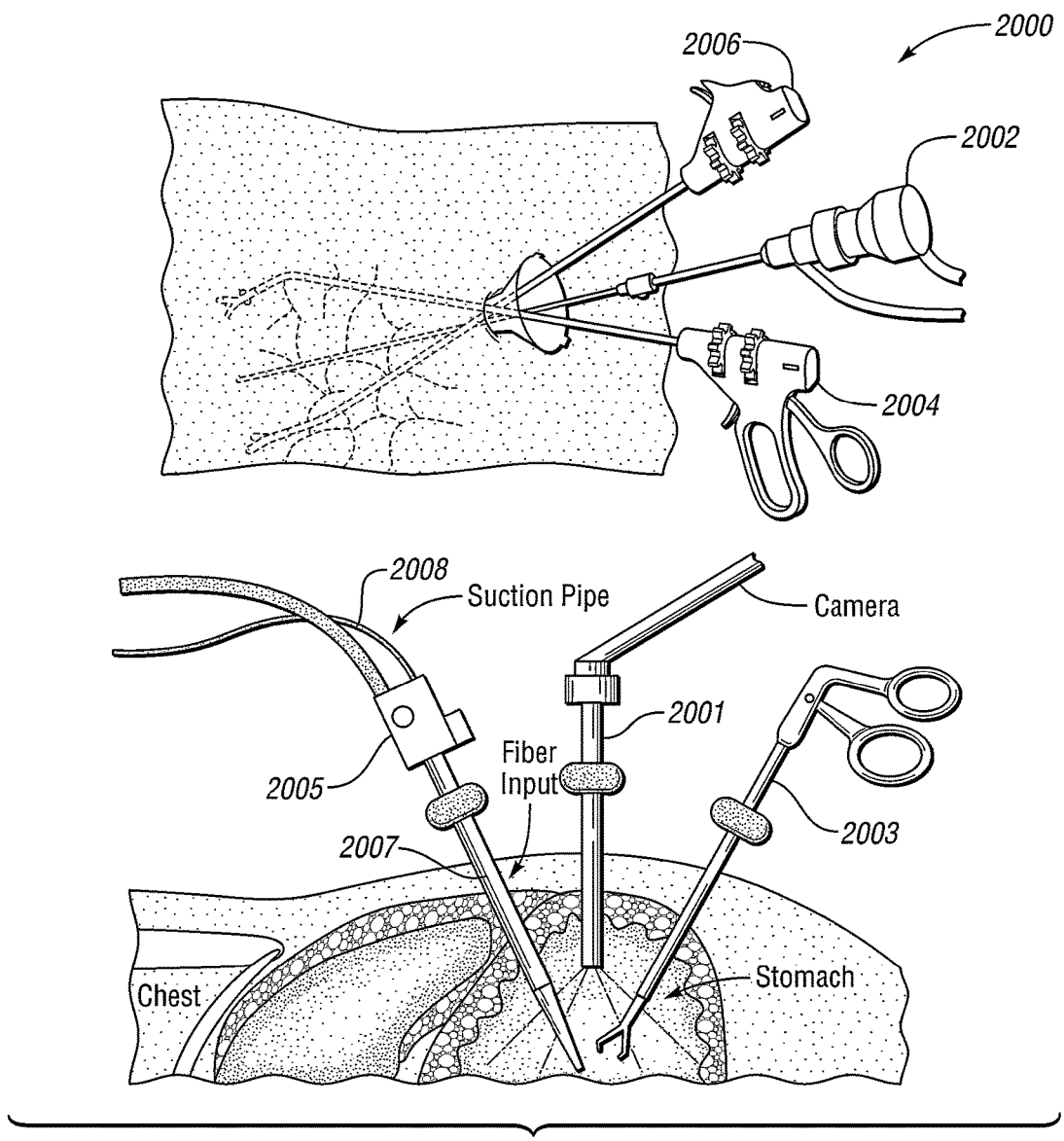
FIG. 20 illustrates an exemplary laparoscopic device for use for introducing light into the abdominal region; in one embodiment, such a laparoscopic device could be used to remove visceral adipose tissue.
Figure 21:
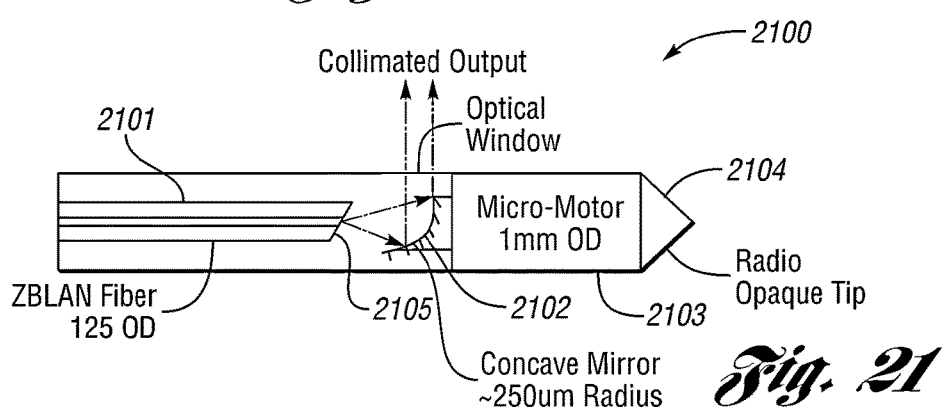
FIG. 21 shows a schematic for an exemplary probe or catheter that can be used for inserting into an artery.

In one preferred embodiment, the mid-infrared laser light can be injected into the adipose tissue around an organ through a catheter or laparoscopic device. For example, FIG. 20 illustrates a laparoscopic device 2000 that might be used to access the visceral fat depots. In this embodiment, three exemplary devices are used: a camera probe for visualization 2001, 2002, a tweezer system for grabbing or holding tissue 2003, 2004, and a catheter 2005, 2006 with a light source with a fiber 2007 and possibly a suction pipe 2008. The catheter 2005, 2006 can include a fiber optic cable to guide the mid-infrared light from the laser system to the end of the catheter probe, and this fiber should be able to transmit the laser wavelengths. There can also be a lens system at the end of the fiber optic cable 2007 to collimate or focus the light at a desired distance from the probe end. The catheter can be guided to the area of interest in the body using an imaging system, such as an x-ray system or a camera based system. In one embodiment, as shown in FIG. 21, the catheter probe can include a radio opaque tip to help identify the catheter location using x-rays. It may be advantageous to also have a camera system in the catheter, similar to what is usually used in endoscopes. That way the operator can watch on an external monitor as the fatty tissue is damaged or melted and as the interface with the organ surface is reached. In one embodiment where the catheter may be used with relatively large pockets of fatty tissue, it may also be advantageous to have a pipe and vacuum system (e.g., a liposuction apparatus) to remove the melted or damaged fat from in front of the catheter. For example, this can avoid the self-limiting of the damage or melting process, since the fat in front may block further penetration by the mid-infrared laser light.

Beyond using mid-infrared lasers for visceral fat, there are many examples of lipid, adipose, or fat accumulation or growth on the outside of organs that could also benefit from laser treatment. As another example, there is much clinical data that suggests that obese patients grow a layer of adipose tissue around the heart. This epicardial adipose tissue is believed to be responsible for many of the heart ailments associated with obese patients. It is also believed that the body may react to the additional adipose tissue or the adipose tissue itself may emit different chemicals, such as cytokines or macrophages. By using laser light near one of the absorption peaks in adipose tissue, the adipose tissue can be damaged or melted. One concern in such a procedure is that the fat is damaged with minimal damage to the heart muscle. Thus, a procedure is desired that melts the fat, but that can be reasonably halted before reaching the heart muscle.

Figure 22:
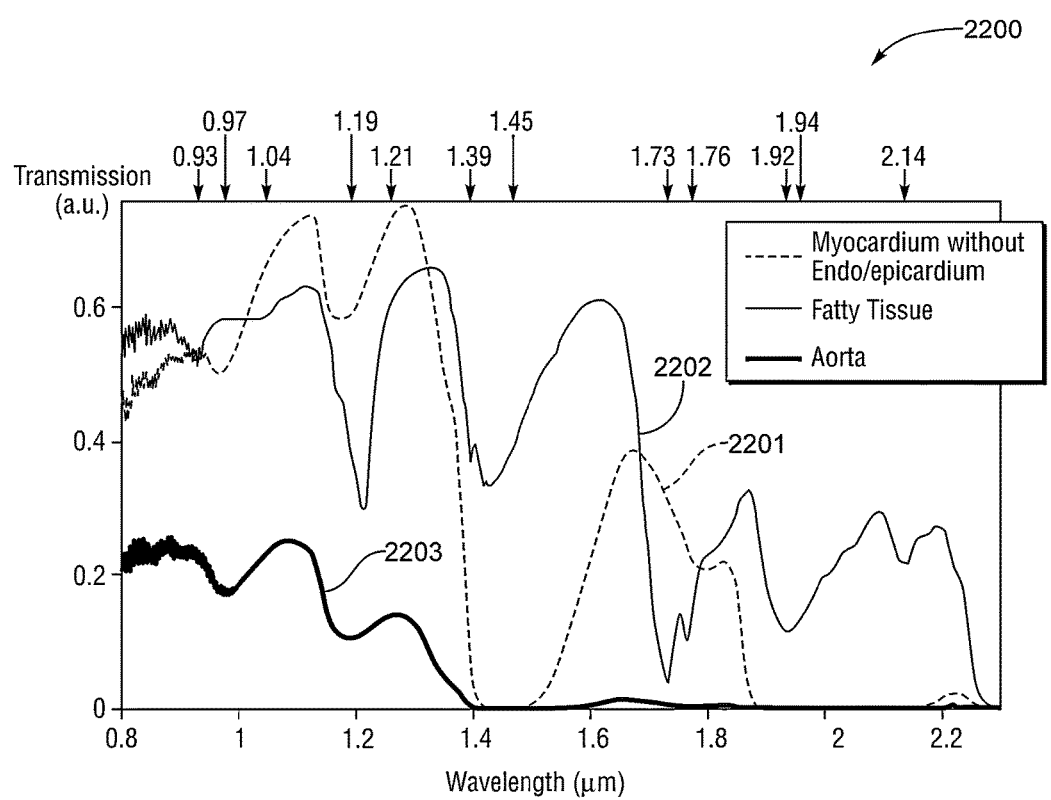
FIG. 22 illustrates the transmission (one minus the absorbance) through fatty tissue, aorta and heart muscle or myocardium without endo- or epi-cardium; the longer arrows indicate some of the water absorption bands, while the shorter arrows indicate some of the approximate absorption bands in fatty tissue.

In the case of melting or damaging adipose tissue around the heart, the selectivity of the laser and its wavelength is desirable to distinguish between the adipose tissue and the cardiac muscle. Cardiac muscle is a type of involuntary striated muscle found in the walls of the heart, specifically called the myocardium. As an example, the transmission (1 minus the absorption in the sample) 2200 through myocardium (heart muscle) 2201, fatty tissue (adipose) 2202 and aorta 2203 is shown in FIG. 22 (note that the scale is in arbitrary units). As shown in FIG. 7, the fatty tissue has an absorption peak around 1720 nm. FIG. 22 shows, however, that the myocardium 2201 has a local dip in absorption (i.e., local peak in transmission) between approximately 1600 nm and 1800 nm. Also, most of the dips in the transmission spectra from myocardium 2201 and aorta 2203 can be attributed to water absorption bands at 0.97, 1.19, 1.45 and 1.94 microns (pointed out by the longer arrows in FIG. 22). On the other hand, fatty tissue has different spectral signatures with dips near 0.93, 1.04, 1.21, 1.39, 1.72, 1.76, 1.92 and 2.14 microns, which are indicated by the shorter arrows in FIG. 22. Therefore, selective damage or ablation of fatty tissue 2202 can be done in the wavelength window near 1720 nm, since the myocardium 2201 has a local minimum in absorption around this range. In one embodiment, the laser power near 1720 nm can be reduced as the interface between the adipose and the heart muscle is approached. With the difference in absorption between the adipose and myocardium, the damage to the myocardium can be at least minimized. In another embodiment, it may also be desirable to introduce local cooling, so that the heat transfer into the myocardium tissue from the adipose is also reduced.

Applications in Cardiology for Diagnostics and Therapeutics

As another example, obesity and excess adipose tissue can also lead to may cardiovascular disorders. For example, atherosclerosis is one example of an ailment associated with plaque build-up in the arteries. In 2009, it is estimated that atherosclerosis causes 650,000 deaths in the US annually, and approximately 17 million deaths worldwide. Most existing techniques for examining plaque are based on morphology of plaques, such as the constriction of the arteries. However, it is estimated that only about 15% of the heart attacks result from plaque that grows to the point of constricting blood flow.

By using wavelengths in the mid-infrared, particularly wavelengths between about 1.5 microns and 4.5 microns, in one embodiment it may be possible to perform diagnostics of atherosclerosis by examining chemical signatures more so than morphology. To detect so-called vulnerable plaque, the chemical signatures could be used to distinguish normal aorta walls from plaque, even potentially distinguish stable from unstable plaque.

Figure 17:
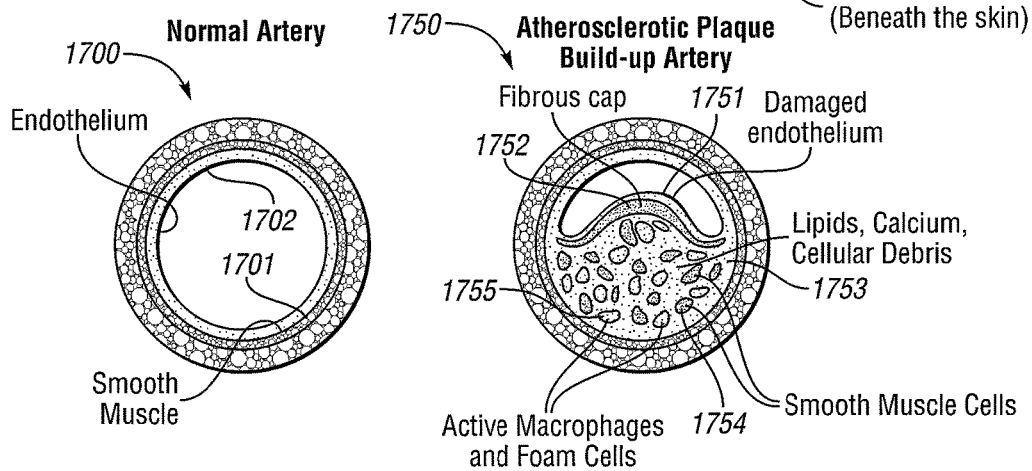
FIG. 17 provides a schematic of a normal artery (left) and an artery with atherosclerotic plaque build-up on the inside walls (right)

In one particular embodiment, a mid-infrared SC light source has been used to perform diagnostic spectroscopy of the constituents of atherosclerotic plaque. For example, FIG. 17 illustrates some of the differences between normal artery 1700 and atherosclerotic plaque build-up in an artery 1750. A normal tissue 1700 has smooth muscle cell 1701 with an endothelium layer 1702 on the inside of the artery 1700. In an artery with atherosclerotic plaque 1750, the endothelium layer 1751 may be damaged, and there can also be a thin layer of fibrous cap 1752 separating the endothelium 1751 from the plaque 1753. The atherosclerotic plaque 1753 comprises a number of constituents, including smooth muscle cells 1754, active macrophages and foam cells 1755 and lipids, calcium and cellular debris. Thus, a normal artery 1700 has a different composition than atherosclerotic artery 1750, and the two may be distinguished based on different optical absorption spectra. Moreover, light that is selectively absorbed in the lipid-rich plaque 1753 may be able to damage the plaque, or at least render it less active in creating bio-chemical reactions in the body.

Figure 18:
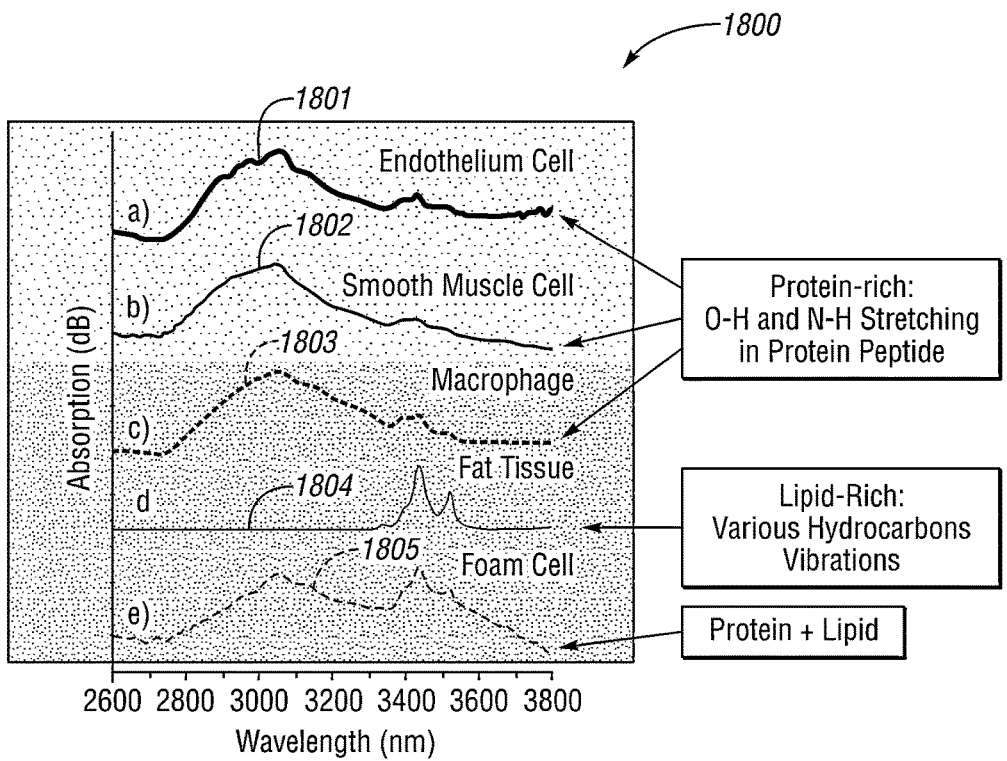
FIG. 18 illustrates exemplary measured optical spectra of constituents in atherosclerotic plaque and normal artery walls between the wavelengths of approximately 2600 nm and 3800 nm; some of the constituents of normal artery include: (a) endothelium cell and (b) smooth muscle cell; some of the constituents of atherosclerotic plaque include: (c) macrophage, (d) fat tissue, and (e) foam cells.

In one non-limiting example, mid-IR absorption spectra of the components of normal artery, which includes endothelial cells 1801 and smooth muscle cells 1802, are illustrated in FIGS. 18 ($a$) and ($b$). As the compositional elements of the normal artery, endothelial cells 1801 and smooth muscle cells 1802 exhibit similar absorption features in the 2.6-3.8 μm wavelength range. A broad absorption feature ranging from 2.8-3.2 μm and peaking at ~3050 nm is observed, and this can be attributed to the vibrational bands of O—H stretching in the hydroxyl group and N—H stretching present in the protein amino acids.

The absorption spectra for some of the constituents of plaque, including macrophages 1803, adipose tissue 1804, and foam cells 1805 are illustrated in FIGS. 18 ($c$), ($d$) and ($e$). In the lipid-rich samples, including adipose tissue 1804 and foam cells 1805, the individual absorption lines can be distinguished in the 3.2-3.6 μm windows, e.g. =CH stretching vibration at ~3330 nm, $CH_3$ stretching vibration at ~3390 nm, and $CH_2$ stretching vibration at ~3420 nm and ~3510 nm. In addition, while the macrophages 1803 exhibit a similar absorption spectrum as compared to the normal artery cells 1801 and 1802, prominent spectral characters between ~3.2 to 3.6 μm with two absorption peaks at ~3420 nm and ~3510 nm are observed in the macrophages-transformed foam cells 1805 and adipose tissue 1804 absorption spectra. Such spectral pattern may arise from the absorptions of hydrocarbon chains, e.g. $CH_2$ and $CH_3$ bonds, present in both the fatty acids and cholesterol esters, both of which fall in the adipose tissue category. Therefore, the spectral difference between the macrophages 1803 and foam cells 1805 is consistent with the pathological relationship between these two cell types, i.e. macrophages engulf lipid-rich substances to become foam cells.

To further investigate the composition properties of the constituents of plaque, the absorption spectrum has been measured of egg yolk 1901, which is considered to be a conventional composite model of atherogenic lipoprotein. The spectral character of egg yolk 1901 (FIG. 19), shares many similarities with that of foam cells 1805 (see FIG. 18(e)). Compared to endothelial cells 1902 and smooth muscle cells 1802, which form the normal artery, egg yolk 1901 shows distinct lipid-rich absorption features in 3.2-3.6 µm wavelength range while having comparable absorptions in the 2.8-3.2 µm O—H and N—H vibrational bands.

Although the example of FIGS. 18 and 19 show that a large absorption peak can be observable from adipose tissue between approximately 3400 to 3500 nm, one problem with performing diagnostic in this wavelength range is that the water and blood absorption can be very strong (in this wavelength range, the absorption for blood and water are approximately equal). For instance, at 3400 nm the water absorption is approximately 700 cm$^{-1}$, and even at 3500 nm the water absorption is about 334 cm$^{-1}$. Therefore, it might be difficult to perform spectroscopy of the atherosclerotic plaque without either putting the probe directly in contact with the endothelium layer or pausing the blood and water flow through the artery.

In a preferred embodiment, the diagnostics or spectroscopy of the plaque can be performed in the first overtone wavelength range, for example in the wavelength range between 1300 and 1900 nm, more preferably in the wavelength range between 1700 nm and 1750 nm. Similar to FIGS. 18 and 19, spectral features will be observable in this first overtone window, but one advantage can be that the water and blood absorption may be considerably weaker. For example, the water absorption coefficient at 1700 nm is about 5.15 cm$^{-1}$, while at 1750 nm the absorption coefficient is approximately 6.4 cm$^{-1}$. The lower water and blood absorption can make it more likely to perform spectroscopy in this wavelength range.

As another embodiment of diagnostics or spectroscopy in cardiovascular medicine, broadband sources in the mid-IR can also be used with abdominal aortic aneurysms (AAA). An abdominal aortic aneurysm is exemplary when the large blood vessel that supplies blood to the abdomen, pelvis and legs becomes abnormally large or balloons outward. The type of plaque considered most vulnerable to disruption is a thin-capped fibroatheroma with increased inflammatory cell content. A thin-capped fibroatheroma typically has a cap thickness of less than 100 microns and a lipid core accounting for greater than 40% of the plaque's total volume. Plaque rupture is among the most frequent type of plaque complication, accounting for an excess of 70% of fatal acute myocardial infarctions and sudden coronary deaths.

Collagen and elastin are major structural components of vessel walls that have been widely implicated in aneurysm formation, progression and rupture. For example, the most prevalent structural modification associated with human AAA's that has been reported is a reduction in elastin concentration in the aortic wall. Also, increased collagen concentration is another matrix modification that has been widely observed in human AAA's. It can be noted that Collagens I and III are the principal collagen components of the aorta. The mid-infrared spectra for collagens and elastins are illustrated in FIG. 7, and changes in the optical spectra could be used to potentially diagnose the presence of plaque and changes associated with AAA in the aorta walls. For example, as the ratio of collagen to elastin changes, the optical spectrum in the wavelength range above 1000 nm will also change. In a preferred embodiment, the optical spectrum between 1400 nm and 1800 nm can be measured, and changes in the spectral shapes can be correlated with the ratio of collagen to elastin. For example, spectral fingerprinting or some sort of principal component analysis can be performed on absorption, transmission or reflection data to distinguish between different ratios of collagen and elastin.

As yet another example of using light from SC sources for diagnostics, SC light in the near-infrared can be used to screen for or diagnose colorectal cancer or pancreatic cancer. Colorectal cancer is the fourth most common form of cancer in the U.S. and the third leading cause of cancer-related death in the Western world. One area in need of improvement is accuracy in detection of flat polyps, or fat dysplasia that does not necessarily protrude out of the mucosa. Whereas adenomatous polyps can readily be detected visually using the fiber optic and CCD cameras in endoscopes, flat polyps can be missed, thus increasing the risk of colorectal cancer despite early screening. Moreover, there are diseases such as ulcerative colitis, which is a form of inflammatory bowel disease that do not lead to the outgrowth of polyps. If this disease is suspected, the only diagnostic is to acquire many biopsy samples. Therefore, a technique is required for detecting flat polyps based on their chemical or compositional signatures to distinguish normal mucosa from cancerous tissue.

Colorectal cancer can be distinguished from the normal mucosa by examining the chemical differences in tissue composition using reflection spectroscopy in the near-infrared wavelength range. The differences in tissue composition between colorectal cancer and normal tissues have been extensively analyzed using chemical, histochemical, biochemical and immunohistochemical studies. It has been shown that adenoma and carcinoma of colorectal tissues have altered compositions in fatty acids, carbohydrates, glycosaminoglycans, glycoproteins and glycolipids. In particular, the lipid near-infrared absorption bands provide diagnostic markers useful for colorectal and pancreatic cancer diagnosis. More specifically, due to the rapid proliferation of cancerous cells, there is reduced lipid content in adenoma and carcinoma colorectal tissues.

Prior studies have looked for the missing lipid lines through spectroscopy either in the mid-infrared (e.g., 2000 to 5000 nm) or near-infrared (e.g., 1600 to 1800 nm). The mid-infrared light shows strong signals at the fundamental absorption bands, but the water absorption is much stronger and prevents imaging in a realistic endoscopic setting. In contrast, although absorption changes are smaller in the near-infrared wavelength range, the near-infrared light can transmit through water. Moreover, near-infrared spectroscopy can use standard glass fiber used in the telecommunications industry, which makes it much simpler to transport through the endoscope by addition of a fiber or a bundle of fibers.

In one embodiment, a screen for colorectal cancer may be achieved by adding to an endoscope or a colonoscopy device fibers for reflection spectroscopy in the near-infrared wavelength range. In one embodiment, one or more fibers may be used for illuminating the sample, and then one or more fibers may be used for capturing the reflected signal and bringing back through the endoscope. At the end of the illumination fiber, mirrors or lens may be used to focus or collimate light onto the walls of the colon or large intestines. In a particular example, the illumination and return fibers may form a fiber bundle. In another example, the same fiber may be used for illumination and return of the signal. Once the reflected signal is transported back through the endoscope, the signal can be analyzed using a series of detectors or a spectrometer followed by one or more detectors. For example, an optical spectrum analyzer might be used to look at the signal strength as a function of wavelength.

In a particular embodiment, the spectroscopy can be conveniently performed using a near-infrared SC laser such as in FIG. 12 that can generate light between 1600 and 1800 nm, a wavelength window with multiple C—H first overtone absorption lines and a minimum in water absorption and scattering. With the broadband light, spectral fingerprinting can be performed for inspection of the lipid lines, and the sensitivity can be improved by taking the derivative of the reflected light as a function of wavelength. For example, the SC laser can be coupled to a transmission or illumination fiber, which is used to transport the light from the SC laser to the end of the endoscope for sample inspection. The output from the fiber-based SC laser can be conveniently coupled to a fiber, and a separate fiber is used for illumination any contamination from the endoscope or sample does not affect the SC laser. This permits, for example, the illumination and reflected sample fibers to be used on a patient and then discarded.

Figure 23:
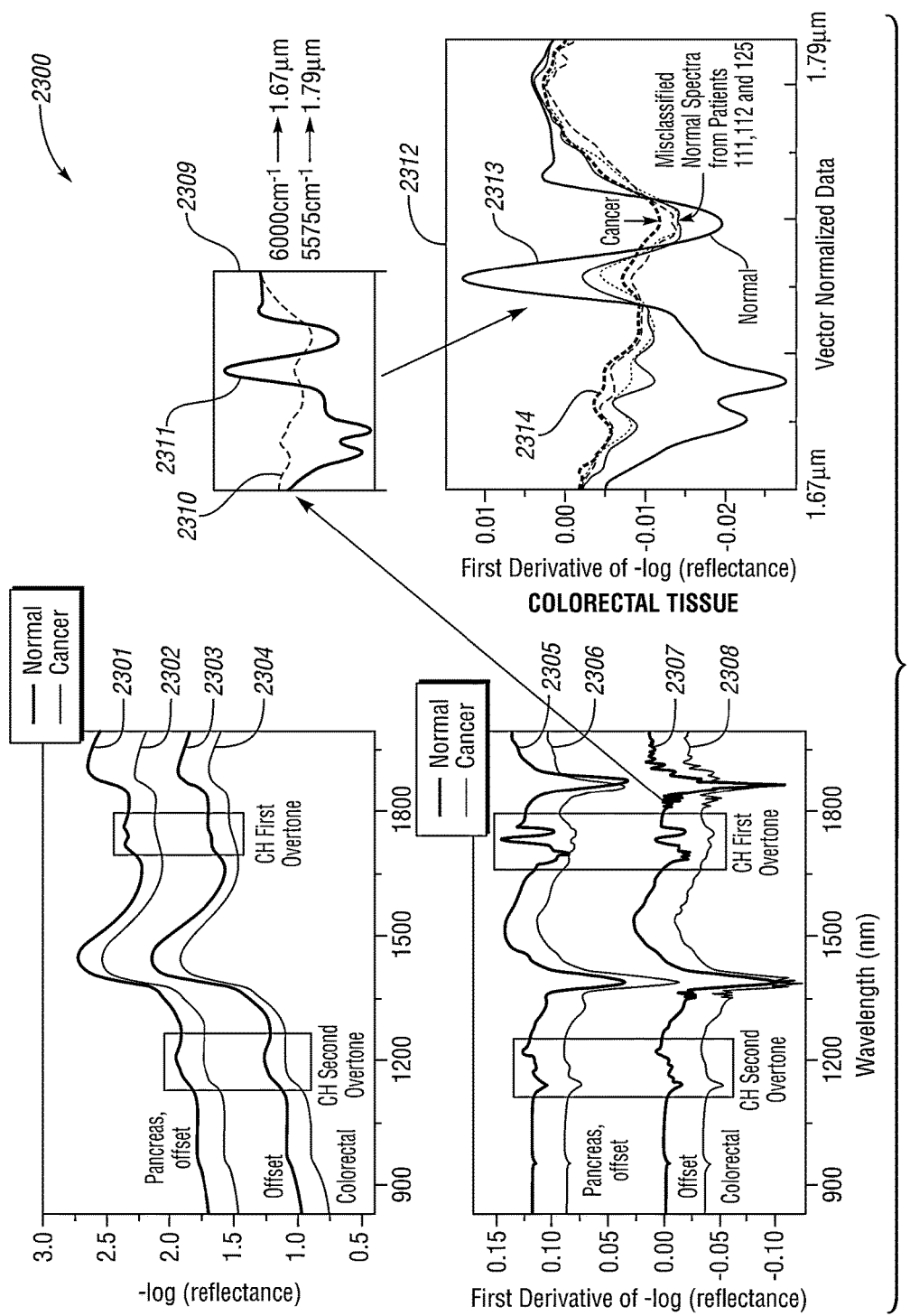
FIG. 23 illustrates near-infrared spectroscopy data for diagnosing colorectal or pancreatic cancer; the top left hand side shows near-infrared spectra for normal and cancerous pancreas and colorectal tissue, while the bottom left hand side enhances the changes by differentiating the reflectance to show the missing lipid lines; the right hand side enlarges the data in the wavelength range between approximately 1670 and 1790 nm, which illustrates the contrast between normal and cancerous colorectal tissue.

As an example, the first overtone of the lipid absorption lines fall in the near-infrared, and vibrational spectroscopy shows weaker but distinct changes between 1670 and 1790 nm. In particular, normal tissue can show distinct lipid lines, but the lines reduce in strength for cancerous tissue. For instance, FIG. 23 illustrates the changes in the near-infrared reflection data between normal 2301 and cancerous 2302 pancreatic tissue, and between normal 2303 and cancerous 2304 colorectal tissue. The differences can be further enhanced by taking a derivative of the data. For instance, for pancreatic tissue the derivatives for normal 2305 and cancerous 2306 tissue are shown, while for colorectal tissue the derivatives for normal 2307 and cancerous 2308 tissue are show. In one embodiment for colorectal cancer, the inset 2309 overlays the derivative data between approximately 1670 nm and 1790 nm for normal 2311 and cancerous tissue 2310. Moreover, the inset 2302 shows derivative spectra for colorectal cancer for different degrees of progress toward cancer. In this example, the normal tissue spectrum is 2313, the cancerous tissue spectrum is 2314, and different curves in between represent different degrees of progress toward a cancerous state. Thus, for the case of colorectal or pancreatic cancer in this example, the spectral signature falls within a minimum in water scattering and absorption from FIG. 6 or 7, so the spectral data should be observable through a colonoscopy procedure.

Spectroscopy, similar to that of FIGS. 18 and 19 in either the fundamental wavelength window between 2600 nm and 3800 nm or the first overtone can be performed using supercontinuum lasers based on fibers. For spectroscopy in the fundamental range around 2600-3800 nm, a ZBLAN-fiber based SC source can be used. On the other hand, for spectroscopy in the first overtone window between approximately 1400 and 1800 nm, a fused-silica or high-nonlinearity fiber based SC source can be used. Alternatively, other broadband lasers with the appropriate wavelength ranges can also be used. In one embodiment, the SC laser light can be coupled to a catheter, which can then be inserted into the artery to perform the diagnostic spectroscopy. In one preferred embodiment, to inspect for plaque inside an artery, a periscope-type catheter that can be rotated approximately 360 degrees may be required.

In one preferred embodiment, absorption or reflection spectroscopy could be performed by coupling the SC light into a catheter 2100 designed using primarily reflective optics. One advantage of using reflective optics is that it can be broadband, and, therefore, be compatible with SC light. As an example, FIG. 21 illustrates a single-mode ZBLAN fiber 2101 based endoscopic catheter 2100 that uses achromatic reflective optics 2102 and allows noncontact measurement. If wavelengths beyond 2.5 microns are used, then mid-infrared fibers, such as ZBLAN, tellurite, fluorides or chalcogenides, can be used advantageously in the probe. If wavelengths shorter than 2.5 microns are used, then the single-mode fiber can be made out of more standard material, such as fused silica. In addition, a radio opaque tip 2104 could be installed in the front end of the catheter 2100 for the position guidance. For instance, x-ray or some other type of imaging system could be used to monitor the position of the catheter tip 2104 and to guide it to the desired location in the body.

The catheter of FIG. 21 comprises at least three main components, i.e. a single mode fiber 2101, a 90 degree off-axis micro concave mirror 2102, and a rotational micro-motor 2103. In this embodiment, the mid-IR light emitting from the angle-cleaved fiber tip 2105 can be first re-directed by 90 degrees and collimated by the concave mirror 2102. If it is desired to confine the collimated beam diameter to the order of ~100-200 µm, the radius curvature of the micro concave mirror could be ~250 µm. In one embodiment, the micro-mirrors could be fabricated and implemented by MEMS techniques on silicon substrate with gold coating. The concave mirror 2102 could be mounted onto a 1 mm diameter rotational micro-motor to enable the 360-degree peripheral optical scan. As an example, the miniature catheter of FIG. 21, which could also be disposable, with an outer diameter of ~1 mm could be mechanically coupled to the output pigtail of a SC laser to construct an integrated, minimally invasive in vivo reflective absorption spectroscopy and laser ablation system. Although one example is provided of a catheter probe 2100, other designs could be used consistent with the elements of this disclosure. For example, other mid-IR catheters include hollow glass waveguide catheters, germanium oxide fiber catheters, or catheters employing large core multimode fibers.

Beyond reflection or absorption spectroscopy, other types of optical measurements can also be used. In one non-limiting example, an interferometric system can be used to measure thickness of various elements, thereby providing morphological information in addition to chemical composition information. For instance, an optical coherence tomography system, which is basically a Michelson interferometer, can be used with the SC light source to measure the thickness of the fibrous cap. As described above, when the fibrous cap becomes thinner than about 100 microns, there is an increased risk of rupture. More particularly, a fibrous cap thickness of order of 65 microns is considered to be of high risk, potentially being in the category of so-called vulnerable plaque.

To perform therapeutic procedures, it may be more desirable to use narrower-band, higher power (or higher spectral density) lasers. For example, to perform the diagnostics or spectroscopy, a broadband laser is advantageous, and a supercontinuum light source is one example of a convenient light source. On the other hand, for therapeutics, where the desire may be to damage selectively on or more compositional elements, it may be more desirable to use a narrower band, higher power light source such as a cascaded Raman oscillator. As an illustration, one therapeutic procedure may be to damage selectively the lipid-rich plaque core lying under the endothelium and fibrous cap (FIG. 17). In one preferred embodiment, a cascaded Raman oscillator operating near 1720 nm may be used to the first overtone band of the fatty acid band (c.f. FIG. 19). A light source near 3400-3500 nm could also be used, although in this wavelength range has more water absorption, so care should be taken to avoid water between the laser emission point and the plaque. Although cascaded Raman oscillators are mentioned, other lasers could also be used consistent with the disclosure. For example, laser diodes, fiber lasers, thulium-doped fiber lasers, quantum cascade lasers, solid state lasers, or mode locked lasers could also be used in the therapeutic procedures.

Although the above discussion has described one example of using the mid-infrared laser light in cardiovascular organs, there are many other situations where the laser procedure can be beneficial by selectively absorbing in adipose, collagen or elastin. In yet another embodiment, there is a growing need for percutaneous valve replacement, for example with the aortic or pulmonary valves. When an artificial stent or valve is placed in the body, it may also be desirable for the collagen to cross-link and secure the stent or valve in place. By using mid-infrared light near the stent or valve, collagen contraction can occur locally, and the heat generated in the collagen can also promote collagen cross-linking. There may be a further advantage of also heating the elastin locally in the vicinity of the stent or valve.

In yet another embodiment, the mid-infrared laser light could be used to minimize collateral damage for procedures in the brain. For example, mid-infrared laser light could be used for selective laser ablation for removing tissue obstructions in shunt catheters used in hydrocephalus. Hydrocephalus is defined as an excessive accumulation of cerebrospinal fluid (CSF) within the cavities of the brain known as ventricles. Hydrocephalus is one of the more common childhood brain disorders, with an incidence as high as 1/500 births. Hydrocephalus is usually a lifelong condition, and the standard treatment involves diverting ventricular CSF through a surgically implanted silicone catheter with a pressure-controlled valve (shunt) into the abdominal cavity, where it is reabsorbed along the belly wall. The number one problem of the shunt is blockage due to tissue growing into the drainage holes, which line the side of the silicone tube. Because of the side placement of the drainage holes, it is virtually impossible to clear the blockage mechanically. Moreover, the same blockage problem is common to any catheter implanted in the body, such as those also used to deliver drugs along the spinal cord or drain abscesses.

As an example, using the mid-infrared light a fiber-based "rotor-rooter" can be implemented to clear the blockage in the shunts by using the selective absorption in the blockage material versus silicone rubber shunts. In fact, silicone rubber can be fairly transparent out to wavelengths longer than 8.58 microns. Standard fiber with 125 micron cladding and 250 micron diameter with coating should easily fit within most of the shunts, which are typically 1-2 mm inner diameter. Moreover, the end of the fiber can be etched or cleaved to emit light at 45 degrees, enabling light delivery to the drainage holes. In one embodiment, a tip design similar to FIG. 21 could be used. By selectively ablating the tissue blocking the shunt drainage holes, the blockage can be removed without requiring surgical removal of the shunt and without damaging the walls of the shunt. It is desirable also not to damage brain tissue just outside the drainage holes.

As yet another example, the mid-infrared light could be used to detect cancerous tumors in the brain. In particular, brain tissue is characterized by high lipid content. The amount of lipids decreases, and its composition changes in the most frequent primary brain tumor, the glioma. For example, spectroscopy of brain tissue has shown that gliomas are characterized by increased water content and decreased lipid content. Based on the different spectra from lipids and water, such as shown in FIGS. 6 and 7, spectral changes should be present for gliomas versus normal brain tissue. In one embodiment, a fiber probe could be inserted into suspect areas of the brain, and light from the brain tissue could be reflected (potentially transmitted, if, for example, two probes are used) to perform reflection spectroscopy. The light could be from a super-continuum fiber laser operating in the range of approximately 1600 to 1800 nm, and the reflected light could be analyzed using a spectrometer. The changes in spectra could also be enhanced by taking a derivative of the reflection data as a function of wavelength. Reflection data from different parts of the brain tissue could be compared. As an example, the normal brain tissue should have lipid lines in the spectra, while the glioma regions should have reduced lipid lines and enhanced water lines. By performing such differential spectroscopy, the boundary between normal and tumor brain tissue could be better demarcated.

Beyond detecting cancerous regions in the brain or central nervous system, mid-infrared light could also be used to cut brain or central nervous system tissue with minimal collateral damage. The precise cuts could be achieved by tuning into lipid lines, and then cutting tissue that is lipid rich. In contrast, many laser cutting procedures rely on absorption in water. First, relying on water can be non-selective, since most tissue has significant water content. Second, as the water in cells is heated, the water in the cells expands as it turns to vapor, causing the cells to rupture. Consequently, water-based heating can lead to significant collateral damage in the surrounding tissue, which would be particularly undesirable for operation in brain tissue or nervous system tissue.

In one embodiment, more precise cuts for tissue of the central nervous system or brain tissue could be accomplished by using a laser tuned near 1720 nm or one of the other wavelength peaks in adipose absorption. As an example, myelin is a dielectric material that forms a layer, the so-called myelin sheath, usually around the axon of a neuron. Myelin made by different cell types varies in chemical composition and configuration, but it still performs the same kind of insulating function. Myelinated axons are white in appearance, hence the term "white matter" of the brain. In particular, myelin is composed of about 80% lipid and about 20% protein. As a consequence, a laser tuned to one of the lipid absorption peaks (FIGS. 6 and 7) could be used to cut myelin regions of the brain or central nervous system with higher precision than a laser tuned to a water line. For example, a fiber could be directed to the region of interest for performing the cut in the tissue. Then, using a cascaded Raman wavelength shifter that emits light near 1720 nm, the light could be used to heat the adipose-rich tissue and provide a clean cut. There should result less damage to the surrounding tissue with less lipid content, resulting in less collateral damage. As an alternative, it may also be desirable to use another wavelength tuned to adipose, such as wavelengths near 2300 nm (c.f. FIG. 7). Because of the higher absorption near the 2300 nm wavelength, the penetration depth can be less, leading again to a more precise cut. This is just one example of accomplishing a clean cut based on tuning to one of the absorption resonances of particular tissue types, such as adipose, collagen or elastin. There are many other parts of the body which can benefit from the precise cuts beyond the brain.

Described herein are just some examples of the beneficial use of mid-infrared laser treatment based on the selective absorption in adipose, collagen and elastin. However, many other medical procedures can use the mid-infrared light consistent with this disclosure and are intended to be covered by the disclosure.

Some features of at least some examples of embodiments of the invention are as follows:

1. catheter based procedure for treatment of obesity related ailments
   a. laser light selectively absorbed in adipose tissue surrounding internal organs, wherein the wavelength of the laser light coincides approximately with a local maximum in absorption in adipose
   b. local minimum in loss from water absorption and scattering in tissue
   c. operate at eye safe wavelengths, operate at wavelength near 1720 nm
   d. light is generated by a fiber laser pumped by laser diodes
   e. catheter includes fiber optic cable capable of transmitting the light and piping to remove adipose damaged in procedure
2. fiber laser is a thulium-doped fiber laser or an erbium-doped fiber laser followed by a cascaded Raman wavelength shifter
3. remove or damage adipose without substantially damaging tissue of organ
4. visceral fat, intra-peritoneal fat, and abdominal fat
5. fat associated with ailments associated with type 2 diabetes or cardiovascular ailments or diseases
6. local cooling to localize damage
7. damage to adipose tissue results in reduction or stopping of cytokines and other chemicals being emitted by adipose tissue
8. catheter also includes lens system, imaging system, camera system
9. light based procedure for treatment of obesity related ailments
   a. laser light selectively absorbed in adipose tissue surrounding internal organs, wherein the wavelength of the laser light coincides approximately with a local maximum in absorption in adipose
   b. local minimum in loss from water absorption and scattering in tissue
   c. remove or damage adipose without substantially damaging tissue of organ
   d. damage to adipose tissue results in reduction or stopping of cytokines and other chemicals being emitted by adipose tissue
10. visceral fat, intra-peritoneal fat, and abdominal fat, fat associated with ailments associated with type 2 diabetes or cardiovascular ailments or diseases
11. organ is heart, and adipose tissue is damaged without substantial damage to myocardium and smooth muscle cells
12. laser wavelength is approximately 1720 nm in the eye safe zone
13. light is generated by a fiber laser pumped by laser diodes
14. (13+) fiber laser is a thulium-doped fiber laser or an erbium-doped fiber laser followed by a cascaded Raman wavelength shifter
15. catheter used for percutaneous procedure, catheter includes fiber optic for delivering mid-infrared light, imaging or camera system, and suction means for removing damaged adipose tissue
16. catheter based procedure for treatment of obesity related ailments
   a. laser light selectively absorbed in adipose tissue surrounding internal organs, wherein the wavelength of the laser light coincides approximately with a local maximum in absorption in adipose as well as approximately local maximum in absorption for collagen and elastin
   b. local minimum in loss from water absorption and scattering in tissue
   c. operate at eye safe wavelengths, operate at wavelength near 1720 nm
   d. remove or damage adipose without substantially damaging tissue of organ
   e. catheter includes fiber optic cable capable of transmitting the light and piping to remove adipose damaged in procedure
17. light is generated by a fiber laser pumped by laser diodes, fiber laser is a thulium-doped fiber laser or an erbium-doped fiber laser followed by a cascaded Raman wavelength shifter
18. damage to adipose tissue results in reduction or stopping of cytokines and other chemicals being emitted by adipose tissue
19. visceral fat, intra-peritoneal fat, and abdominal fat, fat associated with ailments associated with type 2 diabetes or cardiovascular ailments or diseases
20. organ is heart, and adipose tissue is damaged without substantial damage to myocardium and smooth muscle cells.

There are preferred embodiments in which the mid-infrared laser light may need to be delivered within a patient to perform a therapeutic or diagnostic procedure. For example, the mid-infrared laser light can be delivered with a fiber or light-pipe that is housed within a catheter or laparoscopic device. In one non-limiting example, consider the mid-infrared light being directed into an artery using a catheter device. In a preferred embodiment, the catheter may comprise a fiber to deliver or guide the light to its intended destination. The catheter fiber can be coupled using a coupler or a mechanical splice to the output of the mid-infrared laser. Having a separate fiber in the catheter that can be connected or dis-connected from the mid-infrared laser has a number of benefits. For instance, the mid-infrared laser can avoid any damage incurred when the catheter flexes as it passes through the patient. Also, the fiber in the catheter could be disposable, thereby avoiding contamination from one patient to another. Finally, there is an economic benefit to the catheter and laser maker, who can sell a separate catheter fiber per procedure used.

The fiber used within the catheter should transmit a significant fraction of the laser energy at the laser wavelength of the mid-infrared light of interest. As an example, if the mid-infrared wavelength of interest is at or near 1720 nm, then the catheter fiber can be made from fused silica. More generally, for wavelengths shorter than ~2.5 microns, a fused-silica based single-mode, multi-mode, photonic crystal fiber, or light guide can be used. For longer wavelengths, other mid-infrared fibers may be used, such as fibers made from various fluoride, chalcogenide, or tellurite compositions.

In addition to the fiber, the catheter may also comprise collimating or focusing optical elements. For wavelengths shorter than ~2.5 microns, quartz or fused silica lenses may be used. For longer wavelengths, it may be advantageous to have lenses made from other material, such as calcium fluoride, zinc sulfide, chalcogenide, etc. Alternatively, curved mirrors may be used that have a reflective metal coating or dielectric coating that substantially reflects the wavelengths of interest.

In one embodiment, the catheter comprising the fiber can be adapted to be inserted into a patient's body through the femoral artery in a patient's leg or thigh. As in a catheterization laboratory procedure, the catheter may be inserted into a larger artery, and various wires, light pipes or fibers, and other devices can be inserted through the body via the catheter that is inside the artery. Then, the catheter can be guided through the aorta to different parts of the cardiovascular system, including for instance the heart, the renal arteries, or the right atrium (through the inferior vena cava).

As illustrated in FIG. 21, the catheter 2100 may have a radio opaque tip 2104, which permits a physician to guide the catheter 2100 through the body using an x-ray imaging system. Alternately, dyes, fluorescent materials, or other imaging systems can be used to track the location of the catheter as it is inserted into the body. Moreover, dyes, fluorescent materials and/or other imaging systems can also be used to estimate or measure the dimension of the artery or other blood vessel. Alternately, an ultrasound or laser radar type system (e.g., an echo system) may be used to estimate or measure the inner and/or outer dimension of the artery or other blood vessel. For the catheter to safely travel through the arteries, the outer dimensions of the catheter may in one instance be less than 2 to 2.5 mm outside diameter (e.g., 6 or 7 French gauge). In other applications, catheters smaller than about 1-1.5 mm may be desirable; e.g., when the catheters are to be fed through arteries in the arm or wrist. On the other hand, for applications in the main aorta or leg or thigh arteries, larger catheters with outer diameters ranging from approximately 2.5 to 10 mm may be used. Any of the catheter designs in this disclosure may be used with the catheters of smaller or larger dimensions.

In a preferred embodiment, the catheter such as the catheter 2100 may be guided along the length of an artery, and the mid-infrared light may be collimated or focused onto the artery walls to perform a therapeutic or diagnostic procedure. In one embodiment, the laser light from the fiber 2101 may be turned by approximately 90 degrees to collimate or focus onto the artery walls. For instance, FIG. 21 illustrates that a curved mirror 2102 after the fiber output 2105 may be used in the catheter 2100 to turn the light and collimate or focus the light. Therefore, the catheter not only comprises the fiber optic cable or light pipe 2101, but it may in addition comprise optical element 2102 for turning the light and collimating or focusing the light.

Figure 24:
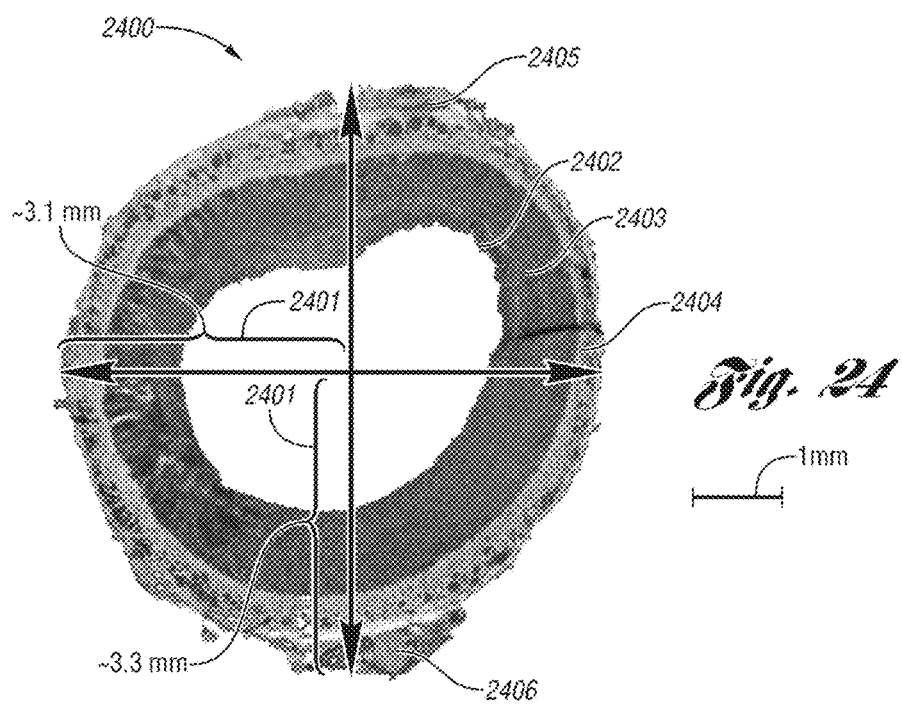
FIG. 24 is a sectional view of a renal artery.

As an example, FIG. 24 illustrates the cross-section of a renal artery 2400 (off-shoot artery from the aorta, leading to the kidneys). In this example, the radius 2401 from the center of the artery to the outside of the artery wall is approximately 3 to 3.5 mm. In this figure, the artery wall comprises (from inside to outside) layers of endothelium 2402, media 2403 comprising mostly smooth muscle cells, adventitia 2404, and a fat or lipid layer 2405. Within the adventitia 2404 and fat 2405 layer are also contained renal nerves 2406. The thickness of the wall of the artery 2400 is this instance is about 1 to 1.5 mm. To avoid damage to the artery 2400 when inserting a catheter, as mentioned earlier, the catheter size should be less than approximately 2 to 2.5 mm outer diameter. Although one embodiment of a renal artery is shown in FIG. 24, it should be understood that the diameter of the artery varies between different locations in the body as well as between different patients.

As a consequence of the different sizes of arteries and wall thicknesses, it is advantageous if the catheter containing the fiber can be adjusted to focus the light to different levels of depth. Then, the physician or medical professional can adjust the focal distance to accommodate different patients and different parts of the body. As will be described below, there are at least three ways to accomplish an adjustable focal distance. First, the distance from the fiber to the curved mirror or lens can be varied to change the focal distance. This can be accomplished in one embodiment by moving the fiber end back and forth along the length of the catheter. Second, the radius of curvature of the curved mirror can be varied to change the focal distance. This can be accomplished in a preferred embodiment if the curved mirror is made of micro-electro-mechanical system (MEMS) mirrors or if the curved mirror is a deformable reflective surface. Third, in another embodiment of a multi-element focusing system, the distance between different focusing optical elements can be varied to change the focal distance. These adjustments can be done manually via a manual actuator or an automatic actuator under control of a computer, an electrical system, or a controller. In one embodiment, the distance of the fiber to the turning mirror can be adjusted using a micrometer-type screw, an inch-worm turning motor or a stepping motor. In another embodiment, there can be an electrical control voltage applied to MEMS or deformable curved mirrors.

In one embodiment, the adjustability of the focal distance and the focal spot size can be illustrated using the design shown in FIG. 21 using a curved mirror 2102 to collimate or focus the light at 90 degrees to the fiber end 2105. FIG. 21 illustrates that the end of the fiber 2105 can be cut angle cleaved to prevent feedback into the mid-infrared laser from the fiber end. Alternatively, the end of the fiber 2105 can be anti-reflection coated. Neither may be necessary if the laser is insensitive to a few percent reflections, or if an isolator is used after the mid-infrared laser. It may be advantageous to also have a camera system in the catheter 2100, similar to what is usually used in endoscopes. In one non-limiting example, the same fiber 2101 can be used to carry the camera signal as the mid-infrared light. Alternatively, one or more separate fibers can be used for the camera and illumination system separate from the fiber or light pipe 2101 delivering the mid-infrared light. In a preferred embodiment shown in FIG. 21, a micro-motor 2103 may be used to rotate the mirror 2102, so that the light can hit different circumferentially spaced positions on the artery walls. Alternatively, the operator or physician can rotate the overall catheter 2100 to change its location or angle. Moreover, the catheter 2100 outer diameter can be less than 2 to 2.5 mm, and a window can be used after the curved mirror to transmit the light to the appropriate location on the artery wall. Finally, as previously described, a radio opaque tip 2104 may be used to monitor the location of the catheter, particularly as it is inserted or drawn back out.

A curved mirror 2102, such as a parabolic or spherical mirror, can be used to turn the light by 90 degrees as well as to collimate or focus the light. In some embodiments, a turn mirror or prism can be used in addition to a lens to focus or collimate the light. One advantage of the curved mirror 2102 is that a single element may be used to turn the light and collimate it and focus it, instead of the two elements used when using a lens. Another advantage of a curved mirror 2102 is that it can accommodate a wide range of wavelengths, since reflective optics (i.e., mirrors) are less susceptible to chromatic changes than refractive optics (i.e., lenses). For example, chromatic aberrations can arise when using broadband light with refractive optics because the index-of-refraction (and, hence, focus length) changes with wavelength. On the other hand, a curved mirror may introduce beam distortions such as coma onto the beam.

Figure 25:
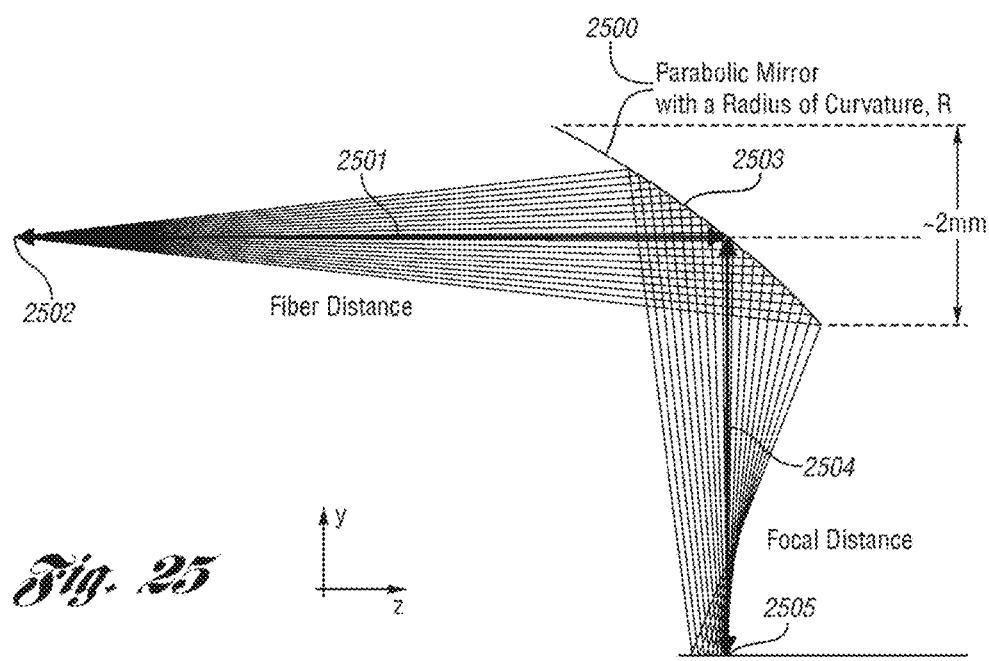
FIG. 25 is a schematic view of a parabolic mirror with a reflective surface having a radius of curvature.

To illustrate the properties of a curved mirror embodiment, a ZEMAX simulation program has been used to calculate the adjustability of the focal length in the curved mirror case. In the simulations provided in the remainder of the disclosure I assume that the fiber is a standard single-mode fiber with a numerical aperture of 0.14 and a core size ranging from 8-10 microns. Although these parameters are selected for the simulations, single mode fibers may have a numerical aperture between about 0.05 and 0.2 and core diameters ranging in size from about 2 to 25 microns or more. For this set of simulations, it is assumed that a 90 degree parabolic mirror is used, and that a focused beam is desired about 1 to 1.5 mm or more depth into the artery wall. FIG. 25 illustrates the simulation conditions, where the fiber distance 2501 is defined from the end of the fiber core 2502 to the center of the curved mirror 2503, and the focal distance 2504 is defined from the center of the mirror 2503 to the location of the focus 2505. The fiber distance 2501 can be varied exemplary by moving the fiber back and forth with respect to the curved mirror, either manually, using inch worms or micrometers, or stepper motors.

Figure 26A:
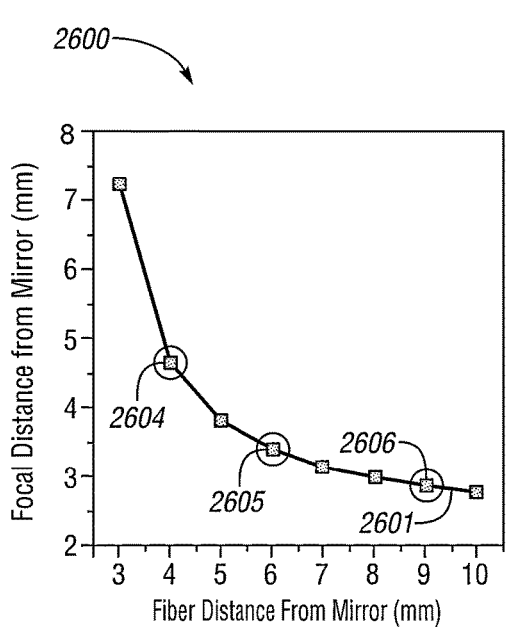
FIG. 26a is a graph of focal distance versus fiber distance for a particular radius of mirror curvature.
Figure 26B:
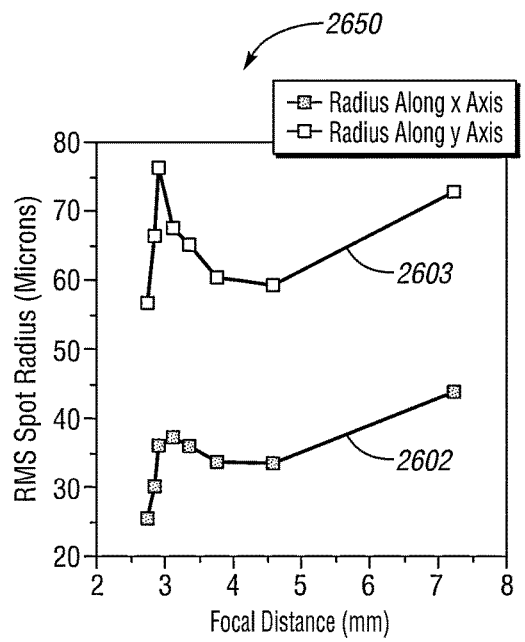
FIG. 26b is a graph of RMS spot radius versus focal distance for the curved mirror.
Figure 27:
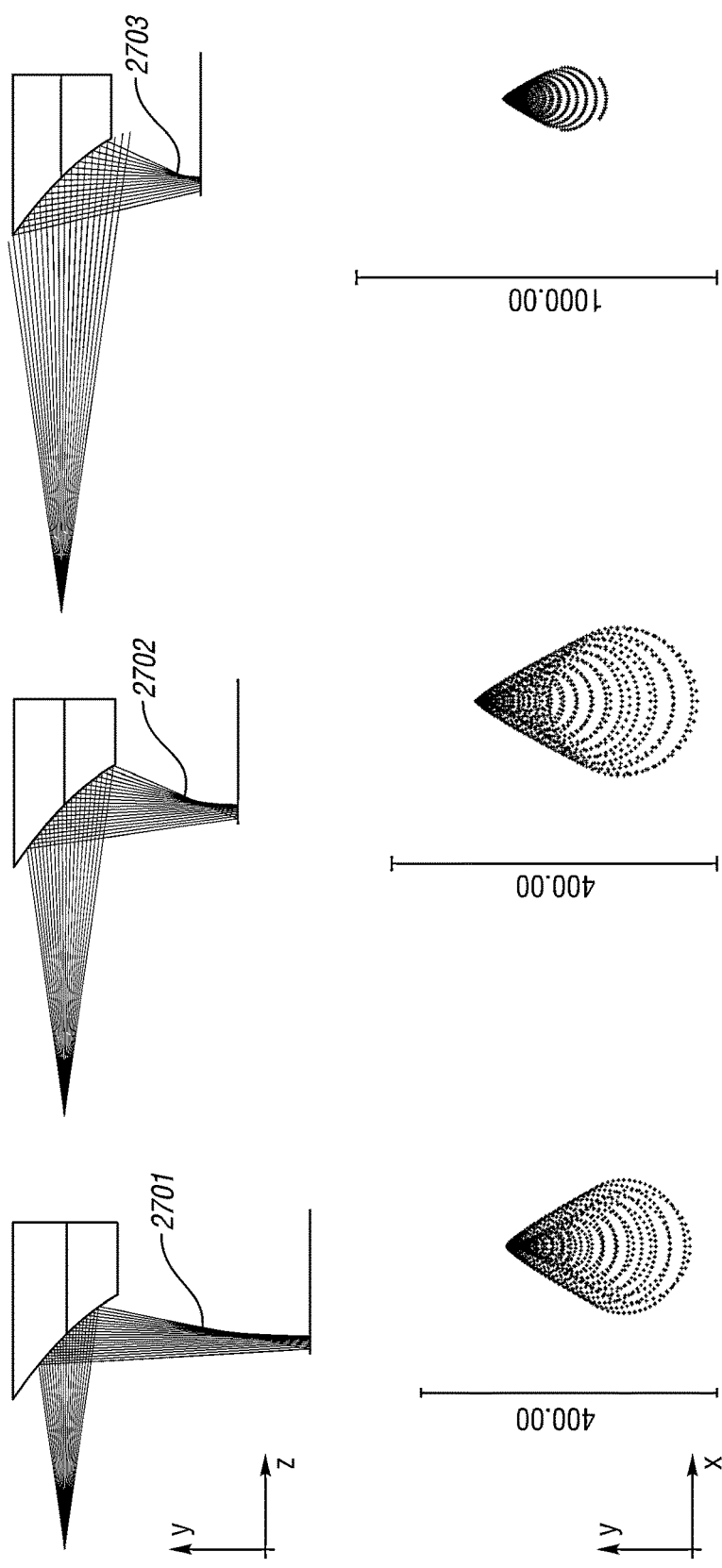

For this embodiment, the calculated results are shown in FIG. 26a, which plots 2601 the focal distance from the mirror versus the fiber distance from the mirror for an assumed radius of curvature of 2.2 mm. As shown, the focal distance can be varied from about 2 mm to greater than 7 mm by changing the fiber distance from 10 mm down to about 3 mm. For the single parabolic curved mirror and 90 degree turn, FIG. 26b plots the focal distance versus root mean square, RMS, spot radius along the x-axis 2602 and the y-axis 2603. In this case, the x- and y-axis results are different, indicating a potential aberration such as coma. To further illustrate the beam shape, FIG. 27 provides spot diagrams at different focal distances for the cases circled in FIG. 26a (2701 corresponds to 2604, 2702 corresponds to 2605, and 2703 corresponds to 2606).

In the configuration similar to FIG. 21 or FIG. 25, an alternative embodiment provides a way to vary the focal distance 2504 by varying the radius of curvature of the curved mirror 2102 or 2503. FIG. 28 shows two particular embodiments of adaptive optics techniques in which the radius of curvature can be adjustable. In FIG. 28a, the curved mirror can be made of a series or three dimensional array of MEMS micro-mirrors 2801, each of which could be rotated and/or moved up and down, preferably in an analog fashion. The plurality of MEMS mirrors are reflective and may also be coupled to a conductive element, and the MEMS mirrors can be fabricated on one or more semiconductor substrates 2802. Above the one or more substrates and below the plurality of mirrors can be one or more electrodes 2803. Thus, the micro-mirrors can be adjusted by changing the voltage between the conductor coupled to the mirrors and the electrodes. By using the series or array of MEMS mirrors, different radius of curvature mirrors can be piecewise constructed.

In an alternative embodiment, the radius of curvature can be adjusted by using a deformable mirror reflective surface 2850 (FIG. 28b). The deformable mirror surface 2851 may also have a conductive layer 2852. The deformable mirror 2851 may be supported above one or more semiconductor substrates, and on the substrates may be grown or attached a plurality of electrodes 2853. By varying the voltage applied to the plurality of electrodes 2853, the shape or radius of curvature of the deformable mirror may be adjusted. Although FIG. 28 illustrates two ways of altering the radius of curvature, other methods may also be used and are intended to be covered by this disclosure.

Figure 29A:
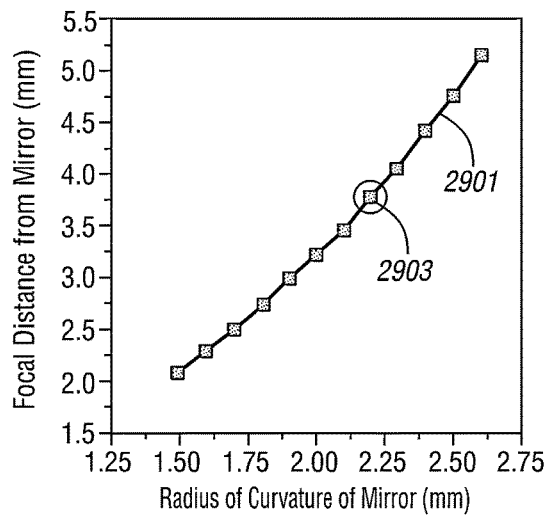
FIG. 29a is a graph of focal distance versus radius of mirror curvature.
Figure 29B:
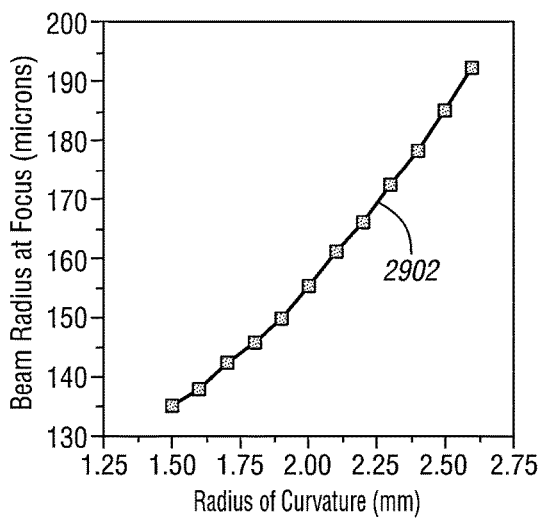
FIG. 29b is a graph of geometric beam radius versus focal distance.

ZEMAX simulations were also conducted for the different radius of curvature mirrors in the configuration of FIG. 25. For example, the results are shown in FIG. 29 assuming that the fiber end is kept 5 mm from the mirror center. FIG. 29a shows how the focal distance from the mirror varies 2901 with different radius of curvature for the mirror. For instance, changing the radius from 1.5 mm to 2.75 mm changes the focal distance from 2 mm to about 5 mm. The circled point 2903 corresponds to the condition used in FIGS. 26 and 27. As the radius of curvature and the focal distance is changed, the beam radius at the focus 2902 also changes (FIG. 29b). The geometric beam radius is plotted in FIG. 29b, which corresponds to the distance of the farthest ray from a reference point. Although these simulations are performed assuming a parabolic mirror shape, other curved mirror shapes can be used and are also intended to be covered by this disclosure.

Despite the simplicity of the single curved mirror configuration of FIG. 21 or 25, beam distortion between one axis and the other may be a limitation. If a symmetric beam is desired, then an alternate embodiment may be used with a flat turn mirror followed by a lens. Although this would appear to have two optical elements, the lens could also serve as a window for the catheter housing. As an illustration, this configuration 3000 is simulated using ZEMAX for the parameters defined in FIG. 30. The fiber end 3005 is a distance 3003 from the center of a flat mirror 3001, which serves to turn the beam by 90 degrees. Then, a lens is placed at the catheter wall, so it can also serve as the window for the light beam to emerge. The focal distance 3004 is defined as the distance from the center of the flat mirror 3001 to the minimum beam waist location 3006. The lens 3002 has a radius of curvature R, where for a lens the radius of curvature is equal to twice the focal length of the lens (R=2f).

Figure 31A:
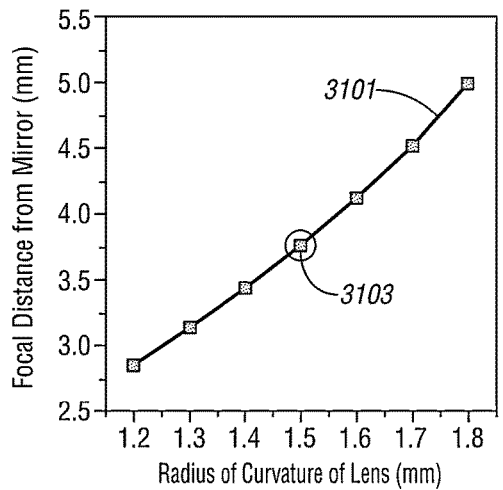
FIG. 31a is a graph of focal distance versus radius of lens curvature.
Figure 31B:
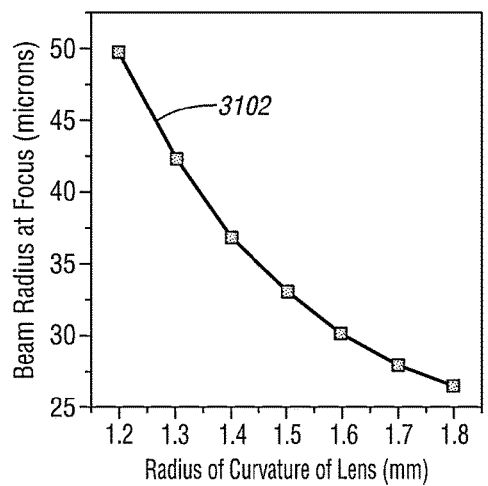
FIG. 31b is a graph of beam radius at focus versus radius of lens curvature.

To select the appropriate radius of curvature or focal length of the lens, FIG. 31 plots the focal distance from the mirror 3101 and geometric beam radius at the focus 3102 versus the radius of curvature of the lens, assuming that the fiber is kept 2.5 mm from the mirror center. In one embodiment, 3103 corresponds to a focal distance of ~3.8 mm at a radius of curvature of 1.5 mm. It should be noted that the lens can in another embodiment be made to be adjustable in radius of curvature. In one embodiment, a liquid filled lens can be used, and the radius can be changed by changing the amount of liquid or the liquid pressure. Alternately, if the lens is a multi-element lens, the spacing between lens elements can be varied to change the effective radius of curvature. Because of the improved beam quality with a spherical lens, the beam radius 3102 with the lens in FIG. 31b is tighter than the beam radius using a comparable curved mirror configuration, such as 2902 in FIG. 29b.

Figure 32:
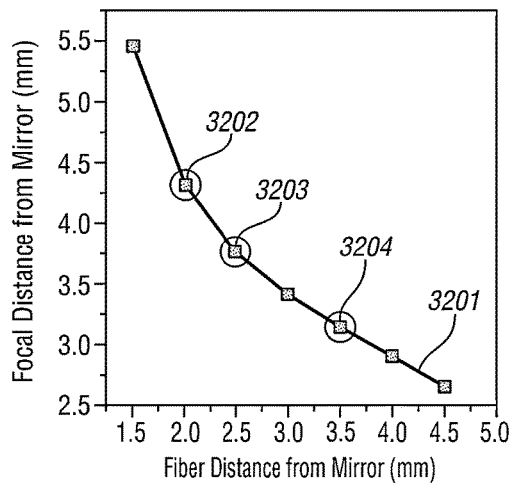
FIG. 32 is a graph of focal distance versus fiber distance from a bending mirror.

Next for the lens system, the focal distance from the mirror versus fiber distance from the mirror 3201 is plotted in FIG. 32, assuming a radius of curvature for the lens of 1.5 mm. By varying the fiber distance from ~1.5 mm to 4.5 mm, the focal distance decreases from ~5.5 mm down to above 2.5 mm. Once again, moving the fiber with respect to the turning mirror leads to a method of adjusting the focal distance. Moreover, for certain focal distances of FIG. 32 (circled points), FIG. 33 provide diagrams for the radius of curvature of 1.5 mm. In particular, curve 3301 corresponds to 3202, curve 3302 corresponds to 3203, and curve 3303 corresponds to 3204. As can be seen, using the lens system leads to a much more symmetric beam along the x- and y-axes. This is also the reason that a tighter focus beam waist is possible using the lens system.

Although two examples have been provided for turning and focusing the light delivered by a catheter, there are many other embodiments that can also be used and are intended to be covered by this disclosure. As an example, an alternative embodiment may be to use a lens tipped fiber with or without a turning mirror. For instance, lens-tipped fibers may be fabricated by using a laser to shape the end of the fiber, or by using mechanical polishing to create a lens at the end of a fiber. The light emerging from the fiber may then be converging, collimated, or diverging, depending in part on the radius of curvature at the end of the fiber. In some cases, the lens tipped fiber may also be coated, such as when an anti-reflection coating is desired. In one particular embodiment, a lens tipped fiber may be inserted into a catheter and used to focus light near the end face of the catheter. In this case, the focal plane may be adjusted by adjusting the lens tipped fiber location with respect to the end of the catheter face. In an alternative embodiment, by moving a lens-tipped fiber with respect to a flat turning mirror, the focal distance can be varied. A lens tipped fiber may be combined with any of the designs for catheters described in this specification.

Figure 34:
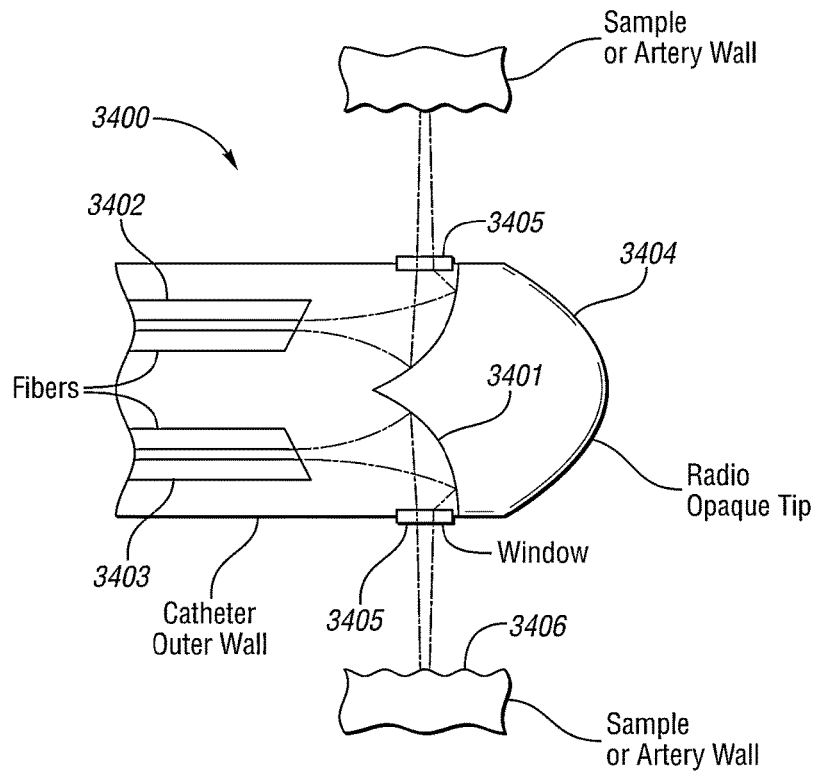
FIG. 34 is a side schematic view, partially broken away, of a cylindrically symmetric catheter probe between the side walls of a sample or artery.

In the design of FIG. 21, to perform therapeutic or diagnostic procedures on multiple angles requires either rotation of the tip using a micro-motor 2103 or manual rotation of the catheter. As an alternative, a conical shaped reflective surface can be used to turn and focus multiple spots in an artery. In one embodiment, FIG. 34 shows the cross-section of a cylindrically symmetric catheter probe 3400. The curved mirror can be rotated about the cylindrical surface to create a pointy conical surface 3401. Then, multiple fiber outputs can be focused into different directions. In a particular embodiment, FIG. 34 illustrates two fibers 3402 and 3403, although any number of fibers could be used. In one preferred embodiment to hit four spots on an artery at 90 degree intervals, four fibers could be used placed symmetrically around the cylinder axis. With these multiple spots, a procedure at a location in the artery could be performed in the four orthogonal directions approximately simultaneously. The fibers could be individual fibers, or they could in a preferred embodiment be a fiber bundle with multiple cores. For individual fibers, the catheter might have four holes in a solid cylindrical insert in the catheter to hold the fibers in place. The catheter can also have a radio opaque tip 3404 for guiding into the patient, and windows 3405 could be used for permitting the light to be passed to the artery wall. One challenge of such a design might be that all the fibers and the conical tip may have to still fit within a ~2 to 2.5 mm catheter outer diameter.

Figure 35:
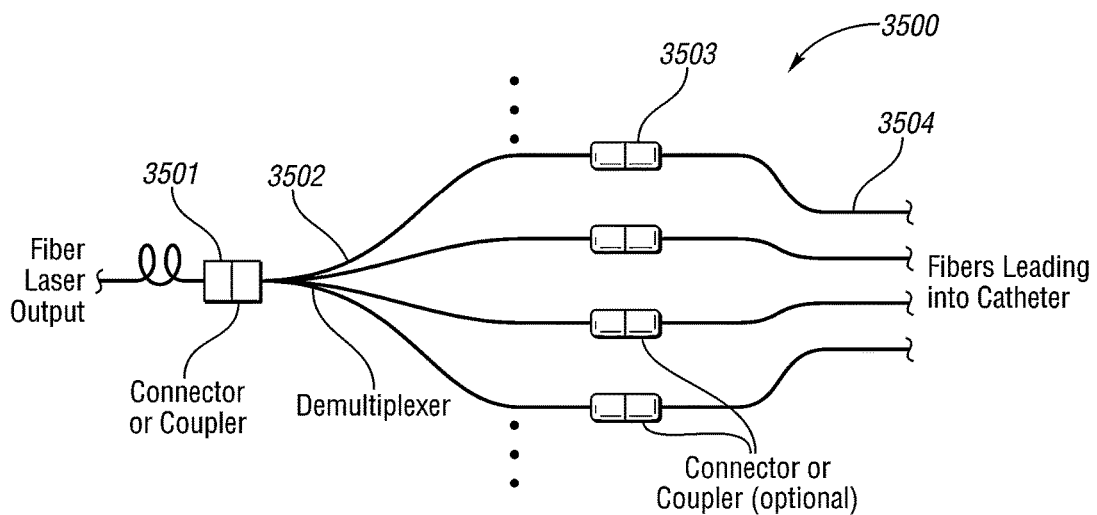
FIG. 35 is a side schematic view, partially broken away, of a single laser output coupled to four fibers which are fed into a catheter.

In the case of multiple fibers used in the catheter such as in FIG. 34, one or more mid-infrared laser outputs can be used. FIG. 35 illustrates one embodiment where a single mid-infrared laser output is coupled to four fibers to be fed into the catheter. First, the output of the mid-infrared laser may be coupled to a connecter or coupler 3501. The connector 3501 may then connect to a demultiplexer 3502 to divide the laser output into four beams. The demultiplexer 3502 could be a power divider, a polarization divider, or a wavelength division demultiplexer, although a power divider would be more appropriate if the same light is to be fed into the four fibers. The output of the demultiplexer 3502 is then coupled to the fibers to be inserted into the catheter 3504. In one preferred embodiment, there may be connector or couplers 3503 to connect the demultiplexer to the catheter fibers, so that the demultiplexer 3502 does not have to be replaced each time even if the catheter fibers are replaced after each use.

Figure 36:
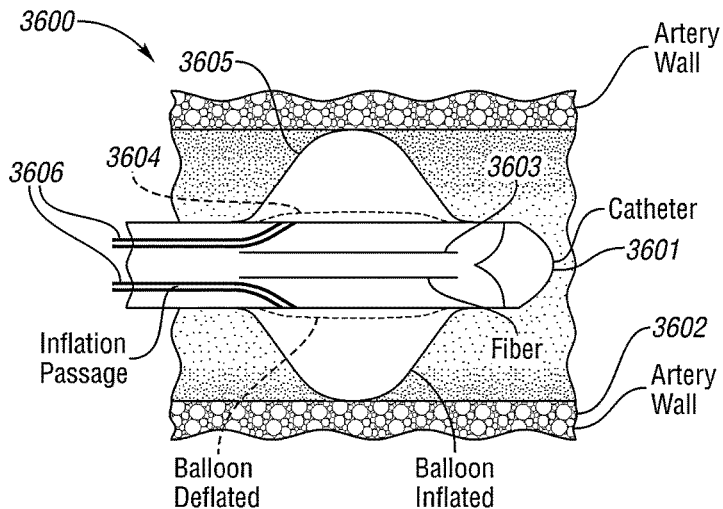
FIG. 36 is a side schematic view, partially broken away and in cross-section, of a catheter device having an inflated balloon which engages the side walls of an artery.

In some applications, it may be desirable to have the catheter positioned approximately near the center of an artery. In addition, it may be desirable to stop or slow the flow of blood and other fluids through the artery temporarily during the procedure. FIG. 36 shows one embodiment of a device 3600 for positioning in the center and impeding blood and fluid flow. In this embodiment a balloon 3604, 3605 is placed around the catheter center 3601, where the balloon can be deflated 3604 while passing through the artery, and the balloon can be inflated 3605 after the catheter reaches near the location desired in the artery. As the expanded balloon 3605 can contact the artery wall 3602, the blood and fluid flow around the catheter can be impeded. It may be acceptable to impede blood flow for short periods of time during a medical procedure. In the example of FIG. 36 the catheter 3601 shown is similar to the design of FIG. 34. One modification may be the addition of a passage 3606 through the catheter, which may have air of fluid for inflating the balloon 3605. Although a particular catheter design with a balloon is shown in FIG. 36, any of the other catheter designs described in this disclosure may be used as the core region of the catheter.

Figure 37A:
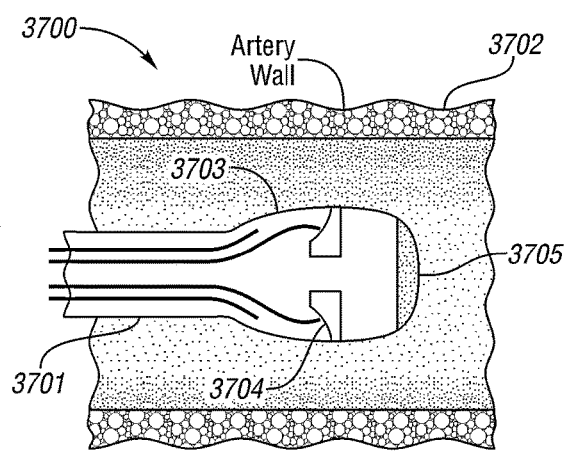
FIG. 37a is a view similar to the view of FIG. 36 with a balloon head of the device deflated.
Figure 37B:
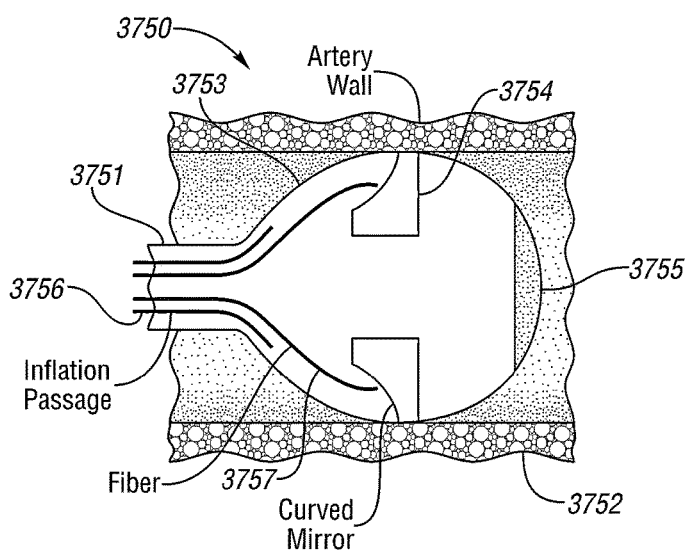
FIG. 37b is a view similar to the view of FIG. 37a with the balloon head inflated.
Figure 38:
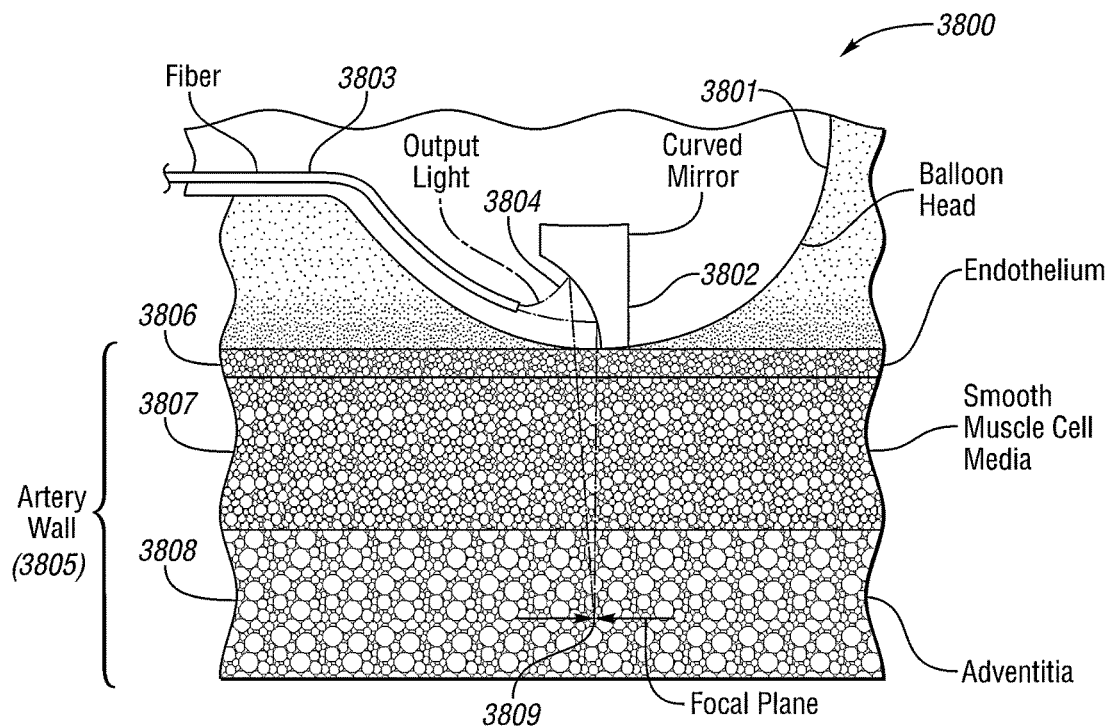
FIG. 38 is a side schematic view, partially broken away and in cross-section, of another balloon-type catheter.

One limitation of the design in FIG. 36 is that the light from the end of the catheter 3601 has to travel through the radius of the artery, and then pass through the artery wall, if necessary. The focal length has to be adjusted for the additional distance, and there may also be additional loss for the laser light as the beam passes through the radius of the catheter. Another embodiment of a balloon-type catheter that may overcome this limitation is illustrated in FIGS. 37 and 38. In this embodiment 3700, the turn mirror and lens or curved mirror 3704 is separated into two or more segments, and each segment may be attached or coupled to the wall of the balloon 3703. As an example, FIG. 37a shows the catheter 3701 within the artery wall 3702 when the balloon 3703 is deflated. This would be the state while the catheter is being inserted into the patient. As with the other designs, there can be a radio opaque tip 3705 to help guide the catheter into the body using an imaging system.

After the catheter is located near the desired location 3750 in the artery wall 3752, then the balloon 3753 may be inflated or expanded. In one embodiment, air or fluid may be passed through an inflation passage 3756 in the catheter. It may be desirable to have the balloon 3753 in contact with the artery wall 3752 to expel blood or fluid between the curved mirror 3754 and the artery wall 3752. Another advantage of the balloon catheter may be that the catheter end is softer and more flexible, so the catheter may approach parts of the body or artery with a cushioned contact. The radio opaque tip 3755 may help identify the location of the catheter head 3700. For the purpose of illustration, FIG. 37b uses the curved mirror catheter design. However, any of the catheter and focusing optics designs described in this specification can be used within the expanding balloon. The catheter tube 3751 may feed in the one or more fibers 3757 in addition to possibly the inflation passage 3756. The curved mirror segments 3754 may be attached to the balloon wall 3753, and as the balloon 3753 is inflated, the curved mirror segments 3754 expand out like petals on a flower. Although two curved mirror segments 3754 are illustrated, any number of segments can be used in such a design. The curved mirror segments 3754 are fed by fibers 3757 that also follow the segments 3754, so that the light can be emitted near the artery wall 3752 at the location of the curved mirrors 3754.

A more detailed diagram 3800 of a particular embodiment with the balloon 3801 in approximate contact with the artery wall 3805 is shown in FIG. 38. The balloon 3801 may be expanded to expel blood or other fluids from the interface with the artery wall. As an example, mid-infrared light may be coupled through the fiber 3803, and the output light 3804 from the fiber may be turned and focused using a curved mirror 3802 that is attached or coupled to the balloon head or wall 3801. The artery wall 3805, for instance, may be composed of an endothelium layer 3806, a smooth muscle cell media 3807, and an adventitia layer 3808. In one preferred embodiment, it may be advantageous to have the focal spot or focal plane 3809 fall within the adventitia 3808 or even beyond the adventitia. For example, damage to the endothelium 3806 or smooth muscle cell media 3807 may be minimized in such a focusing arrangement for a therapeutic procedure. In one embodiment, the damage to the endothelium 3806 and at least the top part (closer to the endothelium) of the smooth muscle cell media 3807 may be reduced or partially minimized because the beam light intensity is lower in these sections as compared with the deeper layers such as the adventitia 3808 where the focal spot lies. In other words, as the beam approaches the focus, the light intensity increases. As described in other embodiments, the focal distance may be adjusted by changing the curvature of the mirror 3802 or by changing the spacing between the end of the fiber 3803 and the curved mirror 3802. Although illustrated in one particular catheter embodiment, any of the other embodiments described in this specification may also be used with the petal expansion of the mirrors or lenses within the balloon 3801.

Figure 39A:
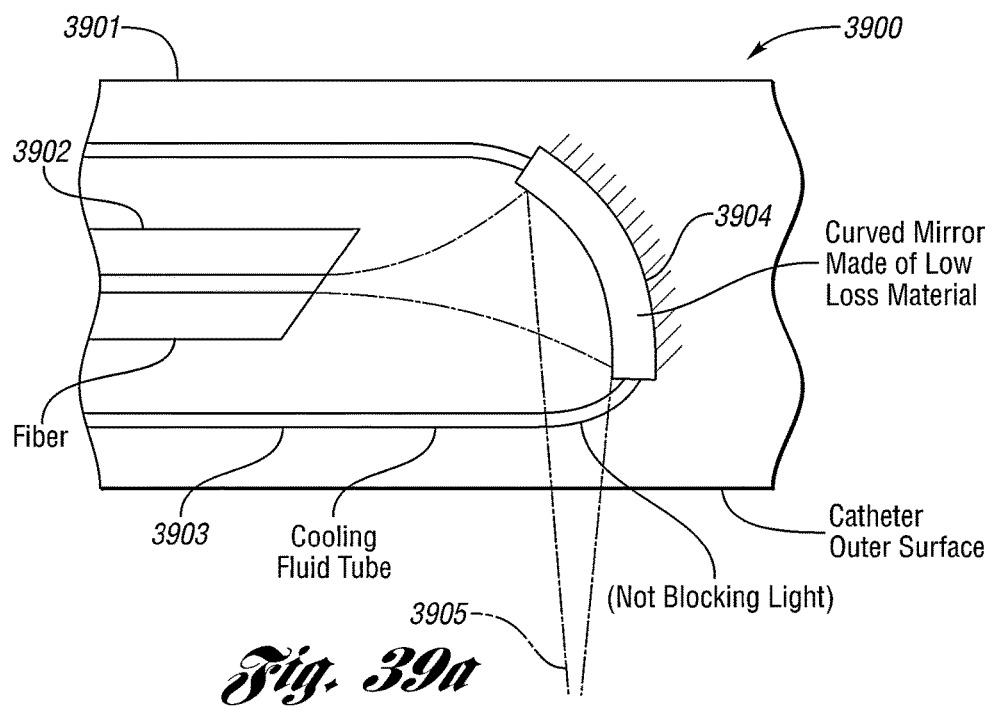
FIG. 39a is a side schematic view, partially broken away, of a catheter having fluid cooling for a curved mirror.

Although particular embodiments for a catheter comprising a fiber or light pipe have been described, any combination of the elements may be used along with other improvements. As an example of other improvements, it may be desirable to cool the light turning mirrors, or it may be desirable to use multiple optical elements. For example, in some particularly therapeutic applications, a significant amount of light may be incident on the catheter focusing element. Therefore, it may be advantageous to cool the optics to avoid thermal damage or significant heat generation in the small area. Although air cooling could be used, air cooling may not be as effective if the catheter outer diameter is only ~2-2.5 mm. FIG. 39 illustrates several embodiments that may be used to reduce the heating within the catheter optics. In FIG. 39*a*, a catheter 3900 is illustrated with fluid cooling for the curved mirror structure. The outer diameter of the catheter is 3901, which also comprises a fiber 3902. The curved mirror surface 3904 of this embodiment has one or more cooling fluid tubes 3903 feeding cooling fluid to and around the mirror 3904 to aid in removing some of the heat. The beam may be focused 3905 outside the catheter, and the cooling fluid tubes 3903 may be positioned to avoid blocking or cutting the light beam. In a further embodiment, it may also be desirable to reduce the heating at the curved mirror 3904 by using a metal or dielectric coating that substantially minimizes absorption at the light wavelengths. For example, if a metal coating is used, then the metal should be selected to have a high reflectivity at the desired light wavelengths. For visible light, the metal coating could be silver, and for infrared light the coating could be gold. Alternatively, a single- or multi-layered dielectric coating could be used to substantially minimize absorption and heating at the mirror 3904.

In an alternate embodiment, the beam size at the catheter optics can be made larger, for example, to reduce the light intensity and heat density on the optics. In one example, FIG. 39*b* shows a catheter 3930 with a tapered fiber 3933 that could be used to expand the beam near the end of the catheter fiber 3932. The outer catheter surface is 3931, and the fiber 3932 is pulled to taper out further 3933 before the light exits. This could be accomplished through the fiber fabrication process, post processing of the fiber by heating it up and reshaping the fiber, or perhaps by splicing on a multi-mode fiber, grin lens, or just a tube of glass at the end of the fiber. The beam size on the turning mirror 3934 would then be larger, still permitting focusing of the light outside the catheter outer surface 3931. The end of the tapered fiber 3933 may be angle cleaved or anti-reflection coated to avoid reflection back into the light source.

In yet another embodiment for reducing the light intensity in the catheter optics, a large mode area fiber or a multi-mode fiber could be used to deliver the light within the catheter. In the example of FIG. 39*c*, the catheter 3960 has an outer surface 3961, and the fiber fed through the catheter 3962 is a larger core size fiber. As an illustration, it may be advantageous to use the larger core size fiber 3962 with an optical design such as described in FIG. 34 with a conical symmetry 3963. The multi-mode fiber might have a core diameter of 50, 65, 100 or even larger microns, for instance. The higher light density could be used to illuminate omni-directionally around the catheter outer surface 3961. The end of the large core area fiber 3964 could also be angle cleaved or anti-reflection coated to minimize retro-reflection into the fiber 3962. Although particular examples for cooling the optics in the catheter have been described for particular types of collimating or focusing optics, these cooling or expanding techniques could be used with any of the optical designs described within this specification.

Many of the examples described thus far involve a single optical element, such as a lens or a curved mirror, for collimating or focusing the light outside the catheter. To provide more flexibility and to reduce the amount of curvature required at the mirror or lens as well as any aberration or distortion penalty, other embodiments may use multiple optical elements for collimating or focusing the light. In one particular embodiment, FIG. 40 illustrates a catheter design 4000 that uses of a grin (graded index) lens 4003 at the end of the fiber 4002 within the catheter outer surface 4001. The grin lens or other refractive element may be used to collimate the fiber output or make a slightly diverging beam 4006 onto the curved mirror surface 4004. The light output can then pass through a window 4005 on the catheter outer surface 4001 to focus the light at an external focal plane 4007. For the example of a slightly diverging or focusing beam 4006 after the grin lens 4003, the distance 4008 between the grin lens 4003 and curved mirror 4004 may be varied to change the distance to the focal plane 4007. Although a grin lens 4003 is shown in FIG. 40, a lens, a lens-tipped fiber, or any other refractive element may be used.

To illustrate the flexibility gained using multiple optical elements, ZEMAX simulations were also performed for different embodiments using multiple elements. In a particular embodiment simulated in FIG. 41, a multi-element optical system 4100 comprises a curved parabolic mirror 4102 followed by a lens 4104 of radius of curvature R. For this particular simulation it is assumed that the mirror 4102 radius of curvature is 2.2 mm. The fiber end 4101 is a distance 4103 away from the center of the mirror 4102, and this distance 4103 may be adjustable. The lens 4104 helps to focus the light in this embodiment to a focal spot 4105 that is a distance 4106 from the center of the mirror 4102. The entire assembly 4100 may advantageously reside within a catheter that may have an outer diameter of ~2-2.5 mm, or any of the other catheter dimensions in this disclosure.

Figure 42:
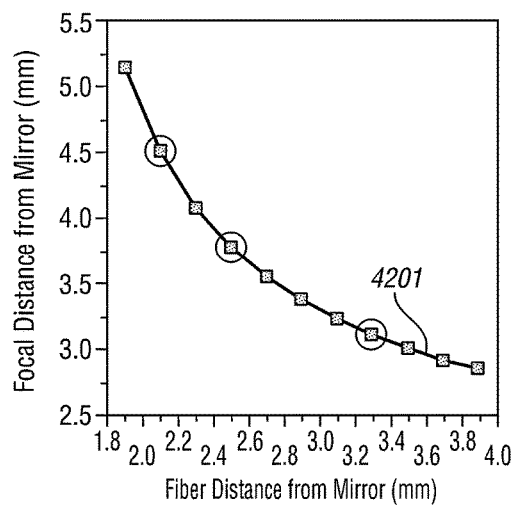
FIG. 42 is a graph of focal distance versus fiber distance for the configuration of FIG. 41.
Figure 41:
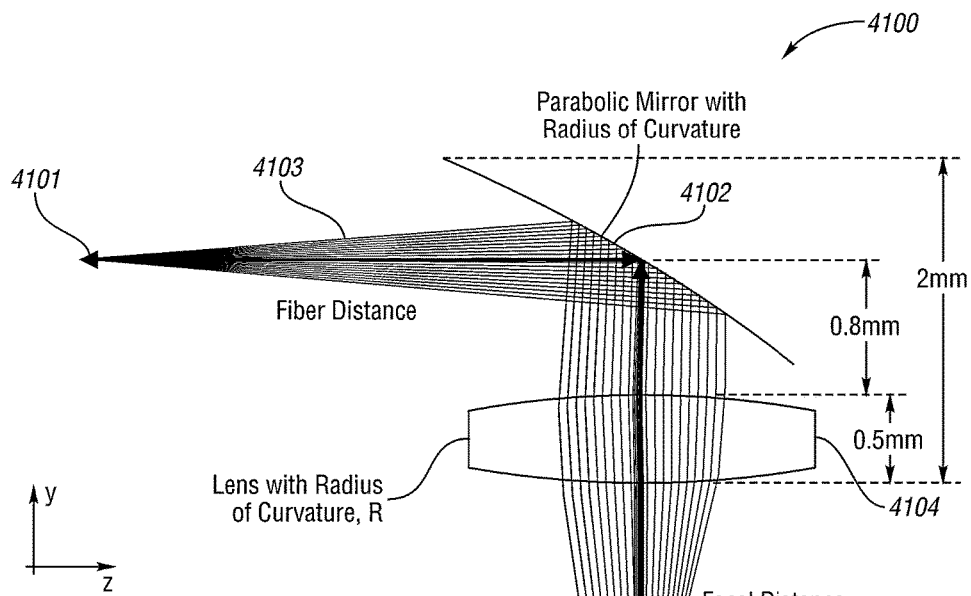
FIG. 41 is a side schematic view of a parabolic mirror with an associated focusing mirror of a multi-element optical subsystem.

The configuration 4100 of FIG. 41 permits flexibility in adjusting the focal distance from the center of the mirror 4102 to the focal spot 4105 in a number of ways. In one preferred embodiment, the distance 4103 of the fiber end 4101 from the curved mirror center 4102 can be varied to change the focal distance 4106. For example, FIG. 42 illustrates a calculation 4201 of the focal distance from the mirror 4106 versus the fiber distance from the mirror 4103 assuming a radius of curvature of the lens R of 3.2 mm (R=2f). In this example the focal distance can be varied from about 5 mm down to more than 2.5 mm by adjusting the fiber distance from approximately 1.8 to 3.9 mm. In another embodiment, the focal distance 4106 can be varied by either changing the radius of curvature of the parabolic mirror 4102 or the radius of curvature or focal length of the lens 4104. The curved mirror 4102 could, in one example, be varied by using a MEMS mirror or a deformable reflective surface. The lens 4104 may be varied by using a fluid filled lens or a multi-element lens with adjustable spacing between the lens.

Figure 43:
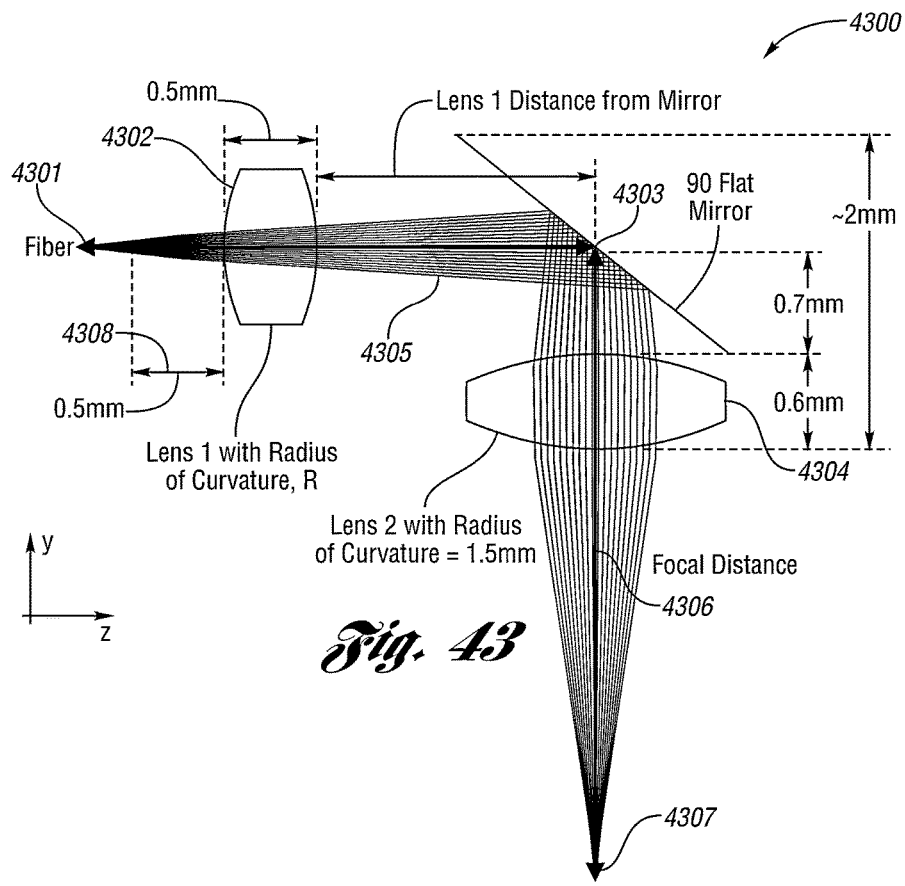
FIG. 43 is a side schematic view of a flat mirror with a pair of lenses of a multi-element optical subsystem.

In yet another embodiment, a multi-element optical catheter design 4300 illustrated in FIG. 43 uses two lenses and a flat mirror to turn the beam by 90 degrees. The fiber end 4301 is assumed for these simulations to be a distance 4308 of 0.5 mm from the first lens 4302. This first lens 4302 is a distance 4305 from the center of the flat mirror 4303, and the beam is focused using a second lens 4304 to a focal spot 4307 that is a distance 4306 from the center of the flat mirror 4303. Although held fixed here, the distance of the fiber to the first lens 4308 could be varied, if desired. Also, although two lenses are illustrated in 4300, any number of lenses could be used and are intended to be covered by this disclosure.

Figure 44B:
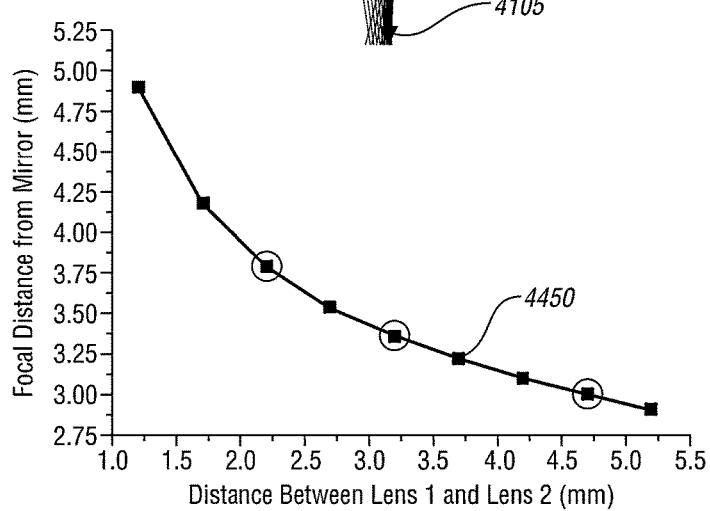
FIG. 44b is a graph of focal distance versus distance between the pair of lenses of FIG. 43.
Figure 44A:
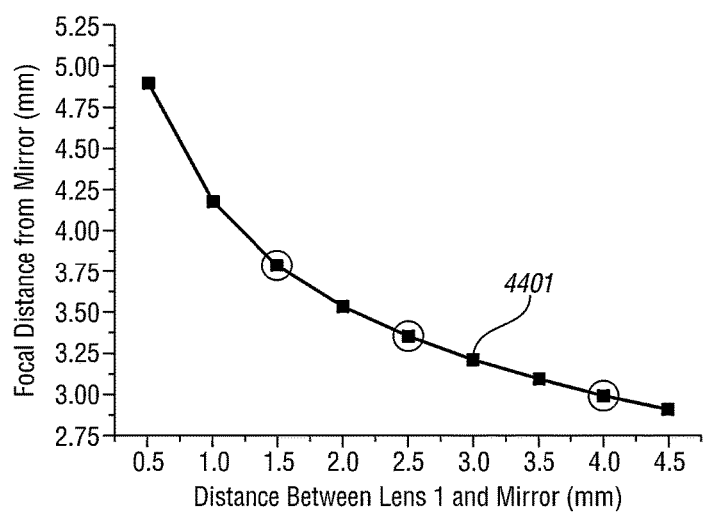
FIG. 44a is a graph of focal distance versus distance between a first lens and mirror of FIG. 43.

There are a number of methods of adjusting the focal distance 4306 in the configuration 4300. For example, FIG. 44a shows a calculation 4401 of the focal distance from the mirror 4306 versus the distance between the first lens and the flat mirror 4305. The focal distance 4306 can be varied from approximately 5 mm down to 2.8 mm by varying the distance between the first lens and the flat mirror 4305 between about 0.5 mm and 4.5 mm. In another preferred embodiment, the focal distance 4306 may also be varied by changing the distance between the first lens 4302 and the second lens 4304. For example, FIG. 44b illustrates a calculation 4450 of the change in focal distance from the mirror 4306 versus the distance between the two lenses. The focal distance can be varied from about 5 mm down to 2.8 mm by varying the distance between the two lenses between approximately 1.1 mm and 5.25 mm. For both of these simulations the fiber is placed 0.5 mm from the first lens, the radius of curvature of the first lens is assumed to be 1.5 mm, and the radius of curvature of the second lens is assumed to be 1.6 mm. These values are exemplary, and other values are also intended to be covered by this disclosure.

Different designs of catheters and optical system have been described in this disclosure. Although particular embodiments are illustrated, the features or parts from different embodiments can be combined or modified. Also, the output laser light has been illustrated to exit orthogonal to the axis of the catheter and fiber, but any angle of exit of light can be used consistent with the disclosure. The light beam could be focused, collimated, or even made divergent exiting from the catheter. Different methods of varying the focal distance to the tissue have been described including moving the fiber end, changing the radius of curvature of the mirror or lens, or varying the spacing between different optical elements. Any combination of these methods could also be used to vary the distance from the catheter to the focal spot. The light beam coupled to the catheter can be from a light source including lasers, lamps, light emitting diodes, or another fiber coming from a different system. The bandwidth of the light could be narrow or wide, and different wavelength of the light could be in the visible, near-infrared, mid-infrared, or even shorter wavelengths. In one preferred embodiment, the wavelength of light could be near 1720 nm, so that the penetration depth into the sample can be about 1 to 1.5 mm or more because of the local minimum in water absorption and scattering. Also, the 1720 nm window may coincide with absorption peaks in different tissue, such as lipids, collagen or elastin. Moreover, the catheter optics can emit the collimated or focused light in one direction, and then the light can be rotated manually or with a motor, or the light might exit in multiple directions using a conical structure with cylindrical symmetry.

Although the present invention has been described in several embodiments, a myriad of changes, variations, alterations, transformations, and modifications may be suggested to one skilled in the art, and it is intended that the present disclosure encompass such changes, variations, alterations, transformations, and modifications as falling within the spirit and scope of the appended claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for selectively processing target tissue material in a patient, the system comprising:
   a laser subsystem for generating an output laser beam, wherein the laser subsystem comprises a plurality of semiconductor lasers multiplexed together into a laser subsystem output fiber; and
   a laparoscopic or catheter assembly including an optical fiber having a proximal end coupled to the laser subsystem output fiber for guiding the output laser beam along a propagation path, the beam having optical and temporal properties and a predetermined selected wavelength, the laparoscopic or catheter assembly sized to extend through an opening in a first part of the patient and to a tissue material processing site within the patient, the laparoscopic or catheter assembly further including a beam delivery and focusing subsystem having a focal distance and disposed in the propagation path and that accepts the output laser beam and positions the beam into at least one focused spot on the target tissue material disposed within a second part of the patient at the site based on distance to the target tissue material from a predetermined point on the propagation path at the site for a duration sufficient to allow laser energy to be absorbed by the target tissue material and converted to heat to product a desired physical change in the target tissue material without causing undesirable changes to adjacent non-target material disposed within the second part of the patient wherein the target tissue material comprises adipose, elastin, or hydrocarbon chains and is characterized by an absorptive coefficient, and wherein the laparoscopic or catheter assembly further comprises a camera probe for visualization, and wherein the laparoscopic or catheter assembly further includes a tweezer system for grabbing and holding tissue, and a suction pipe.

2. The system as claimed in claim 1, wherein the predetermined wavelength is selected to achieve a penetration depth into the second part of the patient of one millimeter or more, wherein the penetration depth is three times the inverse of the absorptive coefficient, and wherein at least a portion of the output fiver comprises a doped fiber.

3. The system as claimed in claim 2, wherein the doped fiber comprises erbium ytterbium, or thulium doping, and at least some of the plurality of semiconductor lasers excite the doped fiber to provide gain to at least a portion of the output laser beam.

4. The system as claimed in claim 1, wherein the predetermined selected wavelength is based on the absorptive coefficient of the target tissue material, wherein the adjacent non-target material has an absorptive coefficient different from the absorptive coefficient of the target tissue material at the predetermined wavelength.

5. The system as claimed in claim 1, wherein the laparoscopic or catheter assembly includes a plurality of optical components disposed along the propagation path.

6. The system as claimed in claim 5, further comprising an actuator for varying distance between a pair of the optical components along the propagation path to change the focal distance.

7. The system as claimed in claim 1, wherein the laparoscopic or catheter assembly further comprises a radio opaque section.

8. The system as claimed in claim 1, wherein the system further comprises a cooling mechanism disposed at the beam delivery and focusing subsystem.

9. The system as claimed in claim 1, wherein the laser beam is a pulsed laser beam, and the pulsed laser beam has a pulse width shorter than several milliseconds.

10. A laparoscopic or catheter assembly for use in a system for selectively processing target tissue material in a patient, the assembly comprising:
a laser subsystem for generating an output laser beam, wherein the laser subsystem comprises a plurality of semiconductor lasers multiplexed together into a laser subsystem output fiber;
an elongated flexible housing;
an optical fiber disposed in the housing coupled to the laser subsystem output fiber for guiding an output laser beam from the output fiber along a propagation path, the beam having optical and temporal properties and a predetermined selected wavelength, the housing sized to extend through an opening in a first part of the patient and to a tissue material processing site within the patient; and
a beam delivery and focusing subsystem having a focal distance disposed in the propagation path and that accepts the output laser beam and positions the beam into at least one focused spot on the target tissue material disposed within a second part of the patient at the site based on distance to the target tissue material from a predetermined point on the propagation path at the site for a duration sufficient to allow laser energy to be absorbed by the target tissue material and converted to heat to produce a desired physical change in the target tissue material without causing undesirable changes to adjacent non-target material disposed within the second part of the patient wherein the target tissue material comprises adipose, elastin, or hydrocarbon chains and is characterized by an absorptive coefficient, the predetermined wavelength being based on the absorptive coefficient of the target tissue material; and
wherein the laparoscopic or catheter assembly further comprises a camera probe for visualization, and wherein the laparoscopic or catheter assembly further includes a tweezer system for grabbing and holding tissue, and a suction pipe.

11. The assembly as claimed in claim 10, wherein the adjacent non-target material has an absorptive coefficient different from the absorptive coefficient of the target tissue material at the predetermined wavelength, wherein the absorptive coefficient of the target tissue material is 0.25 inverse centimeters ($cm^{-1}$) or more different than the absorption coefficient of the non-target material, and wherein at least a portion of the output fiber comprises a doped fiber.

12. The assembly as claimed in claim 11, wherein the doped fiber comprises erbium, ytterbium, or thulium doping, and at least some of the plurality of semiconductor lasers excite the doped fiber to provide gain to at least a portion of the output laser beam.

13. The assembly as claimed in claim 10, wherein the predetermined selected wavelength is selected to achieve a penetration depth into the second part of the patient of one millimeter or more.

14. The assembly as claimed in claim 10, wherein the laparoscopic or catheter assembly includes a plurality of optical components disposed along the propagation path.

15. The assembly as claimed in claim 14, further comprising an actuator for varying distance between a pair of the optical components along the propagation path to change the focal distance.

16. The assembly as claimed in claim 10, wherein the laparoscopic or catheter assembly further comprises a radio opaque section.

17. The assembly as claimed in claim 10, wherein the system further comprises a cooling mechanism disposed at the beam delivery and focusing subsystem.

18. The assembly as claimed in claim 10, wherein the laser beam is a pulsed laser beam, and the pulsed laser beam has a pulse width shorter than several milliseconds.

19. A laparoscopic or catheter assembly for use in a system for selectively processing target tissue material in a patient, the assembly comprising:
a laser subsystem for generating an output laser beam, wherein the laser subsystem comprises a plurality of semiconductor lasers multiplexed together into a laser subsystem output fiber;
an elongated flexible housing;
an optical fiber disposed in the housing coupled to the laser subsystem output fiber for guiding an output laser beam form the output fiber along a propagation path, the beam having optical and temporal properties and a predetermined selected wavelength, the housing sized to extend through an opening in a first part of the patient and to a tissue material processing site within the patient; and
a beam delivery and focusing subsystem having a focal distance disposed in the propagation path ad that accepts the output laser beam and positions the beam into at least one focused spot on the target tissue material disposed within a second part of the patient at the site based on distance to the target tissue material from a predetermined point on the propagation path at the site for a duration sufficient to allow laser energy to be absorbed by the target tissue material and converted to heat to produce a desired physical change in the target tissue material without causing undesirable changes to adjacent non-target material disposed within the second part of the patient wherein the target tissue material comprises adipose, elastin, or hydrocarbon chains and is characterized by an absorptive coefficient, the predetermined wavelength being based on the absorptive coefficient of the target tissue material; and wherein the laparoscopic or catheter assembly further comprises a camera probe for visualization, and wherein the system further comprises a cooling mechanism disposed at the beam delivery and focusing subsystem.

20. The assembly as claim in claim 19, wherein the adjacent non-target material has an absorptive coefficient different from the absorptive coefficient of the target tissue material at the predetermined wavelength, wherein the absorptive coefficient of the target tissue material is 0.25 inverse centimeters ($cm^{-1}$) or more different than the absorption coefficient of the non-target material, and wherein at least a portion of the output fiber comprises a doped fiber.

* * * * *

UNITED STATES PATENT AND TRADEMARK OFFICE
CERTIFICATE OF CORRECTION

PATENT NO.         : 10,271,904 B2
APPLICATION NO.    : 14/719262
DATED              : April 30, 2019
INVENTOR(S)        : Mohammed N. Islam Page 1 of 1

It is certified that error appears in the above-identified patent and that said Letters Patent is hereby corrected as shown below:

In the Claims

Column 58, Line 64, Claim 1:
After "and converted to heat to"
Delete "product" and
Insert -- produce --.

Column 60, Line 62, Claim 19:
After "in the propagation path"
Delete "ad" and
Insert -- and --.

Signed and Sealed this
Twenty-second Day of October, 2019

Andrei Iancu
*Director of the United States Patent and Trademark Office*